US012797476B2

(12) United States Patent
Liu et al.

(10) Patent No.: US 12,797,476 B2
(45) Date of Patent: *Nov. 17, 2026

(54) METHOD OF DELIVERING NUCLEIC ACIDS INTO CELLS

(71) Applicant: GUANGZHOU LIDE BIOMEDICINE TECHNOLOGY CO., LTD., Guangzhou (CN)

(72) Inventors: Zhijia Liu, Guangzhou (CN); Zhicheng Le, Guangzhou (CN); Yongming Chen, Guangzhou (CN)

(73) Assignee: GUANGZHOU LIDE BIOMEDICINE TECHNOLOGY CO., LTD., Guangzhou (CN)

( * ) Notice: Subject to any disclaimer, the term of this patent is extended or adjusted under 35 U.S.C. 154(b) by 478 days.

This patent is subject to a terminal disclaimer.

(21) Appl. No.: 18/232,351

(22) Filed: Aug. 9, 2023

(65) Prior Publication Data

US 2024/0252651 A1 Aug. 1, 2024

Related U.S. Application Data

(63) Continuation of application No. PCT/CN2021/136192, filed on Dec. 7, 2021.

(30) Foreign Application Priority Data

Feb. 9, 2021 (CN) ........................ 202110183415.7

(51) Int. Cl.
*A61K 47/54* (2017.01)
*A61K 9/16* (2006.01)

(52) U.S. Cl.
CPC .......... *A61K 47/544* (2017.08); *A61K 9/1617* (2013.01)

(58) Field of Classification Search
CPC .................................................... A61K 47/544
See application file for complete search history.

(56) References Cited

U.S. PATENT DOCUMENTS

2009/0099118 A1* 4/2009 McSwiggen .......... C12N 15/111
536/24.5

FOREIGN PATENT DOCUMENTS

CN 102231950 A * 11/2011 .............. A61P 31/12

* cited by examiner

*Primary Examiner* — Benjamin J Packard

(57) ABSTRACT

The present application discloses a method of delivering nucleic acids into a cell, including utilization of a cationic lipid analog material. The cationic lipid analog material of the present application can efficiently bind to plasmid DNA, mRNA, siRNA and other nucleic acid molecules, and deliver nucleic acid molecules, achieving efficient gene transfection or gene silencing. Moreover, the cationic lipid analog material has low cytotoxicity. The cationic lipid analog material of the present application can be used as a safe and efficient intracellular delivery carrier of nucleic acid drugs or transfection reagents, and has practical biomedical application value.

16 Claims, 10 Drawing Sheets

METHOD OF DELIVERING NUCLEIC ACIDS INTO CELLS

CROSS-REFERENCE TO RELATED APPLICATIONS

The present application is a continuation application of PCT application No. PCT/CN2021/136192 filed on Dec. 7, 2021, which claims the benefit of Chinese Patent Application No. 202110183415.7 filed on Feb. 9, 2021. The contents of all of the aforementioned applications are incorporated by reference herein in their entirety.

TECHNICAL FIELD

The present application relates to the technical field of biomedicine, and in particular to a method for delivering nucleic acid drugs into cells using an ionizable cationic lipid analog material.

BACKGROUND

Nucleic acid drugs are DNA or RNA with therapeutic functions for diseases, which have the advantages of strong design and good specificity, and are less likely to develop drug resistance. At present, nucleic acid drugs are widely used in protein replacement therapy, gene editing, nucleic acid vaccines, etc. Nucleic acid drugs are unstable and are rapidly degraded by nucleases in the blood or cleared by kidneys. Moreover, the non-specific distribution of nucleic acid drugs reduces the local concentration of the target tissue, and the nucleic acids entering the cell must also successfully avoid and/or escape endosomes and enter the cytoplasm in order to function. Therefore, nucleic acid drugs need to use various carriers to achieve drug delivery. Viral vectors have the advantages of short action time and high transfection efficiency, and are relatively mature delivery vectors of nucleic acid drugs. Although the viruses used for transfection has been specially treated so that their genomes will theoretically not be copied and inserted into the host genome, the viruses are prone to genetic mutation, and the treated viruses may still recover to the wild type with the ability to copy their own genes. In addition, viruses are immunogenic and easily lead to an immune response. Therefore, there are certain safety risks in the preparation and use of viral vectors, which greatly limit their application, and it is necessary to further develop non-viral vectors for efficient and safe delivery of nucleic acid drugs.

SUMMARY

An objective of the present application is to overcome the shortcomings of the prior art and provide a method for delivering nucleic acid drugs into cells using an ionizable cationic lipid analog material.

To achieve the above objective, the present application adopts the following technical solutions:

A method of delivering nucleic acids into a cell, comprising utilization of a cationic lipid analog material, wherein the cationic lipid analog material is an ionizable cationic lipid analog material with a structure shown in formula (I):

I

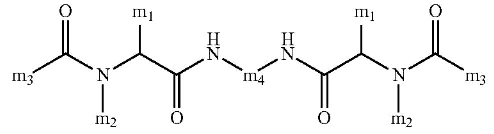

in formula (I), $m_1$ is independently selected from the group consisting of a branched alkyl, phenyl, or a heteroatom-containing aryl;

$m_2$ is

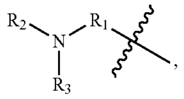

$R_1$ is an alkyl, $R_2$ is an alkyl, $R_3$ is an alkyl or phenyl, or $R_2$ and $R_3$ are connected as a cyclic group or a heterocyclic group;

$m_3$ is independently selected from the group consisting of a linear alkyl, a linear alkenyl, or

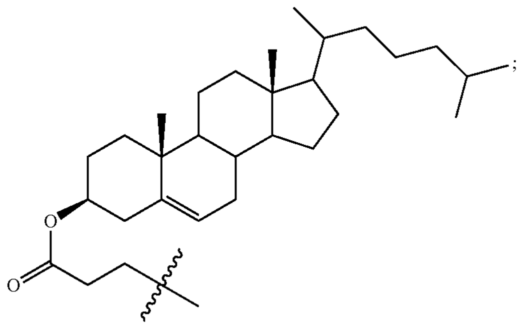 [SMILES: *CCC(=O)O[C@H]1CC[C@@]2(C)C(=CCC3C4CCC(C(C)CCCC(C)C)[C@@]4(C)CCC32)C1]

and $m_4$ is independently selected from the group consisting of a linear alkyl, an ether bond-containing linear alkyl, or an N-heterocycle-containing alkyl.

In the present application, the wavy line in the structural formula represents different configurations, which may be trans, cis, or a mixture of trans and cis.

Whether it is plasmid DNA, mRNA or siRNA, the cationic lipid analog material of the present application can be complexed with it to form a stable complex for efficient intracellular delivery. Moreover, the nucleic acids delivered into the cell can be released from the complex to achieve expression of the transferred gene or silencing of the target gene. The cationic lipid analog material designed in this application can be used as delivery carriers of nucleic acid reagents/drugs or transfection reagents, and can be used to develop universal, efficient, and low-toxicity delivery systems for nucleic acid drugs, which have practical biomedical application value.

It should be noted that the term "delivery" or "intracellular delivery" as used herein refers to the movement of nucleic acids from the outside of the cell to the inside of the cell such that they are confined to the cytosol or within the organelles of the cell.

In addition, in formula (I), $m_1$ is selected from the group consisting of an alkyl, phenyl, and a heteroatom-containing aryl substituted by a substituent a, and the substituent includes methyl; and preferably, $m_1$ is selected from the group consisting of

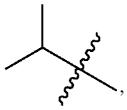

,

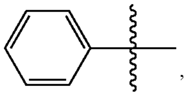

, or

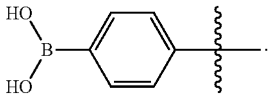

.

In addition, in formula (I), $m_2$ is selected from the group consisting of

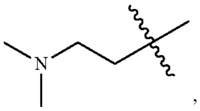

,

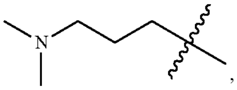

,

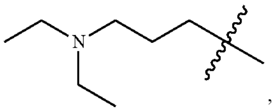

,

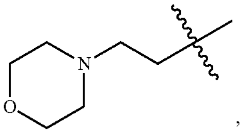

,

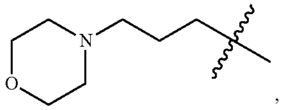

,

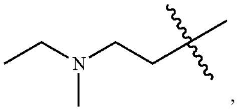

,

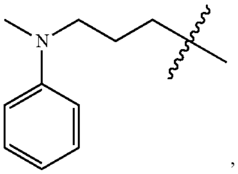

,

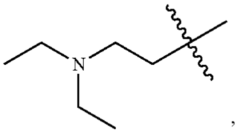

,

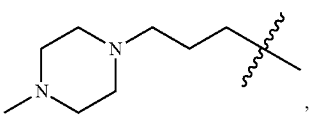

,

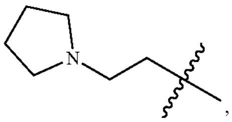

, or

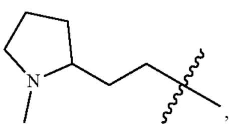

, and the cationic lipid analog material obtained has high transfection efficiency.

In addition, in formula (I), $m_3$ is selected from the group consisting of a linear alkyl with 7 to 19 carbon atoms, a linear alkenyl with 17 carbon atoms, or

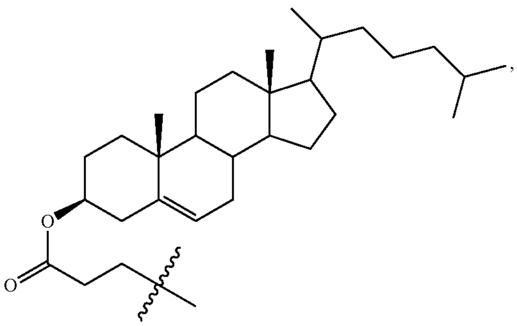 [SMILES: *CCC(=O)O[C@H]1CC[C@@]2(C)C(=CCC3C4CCC(C(C)CCCC(C)C)[C@@]4(C)CCC32)C1]

, and preferably, $m_3$ is selected from the group consisting of

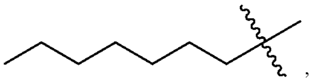

,

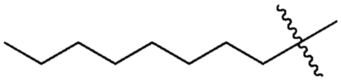

,

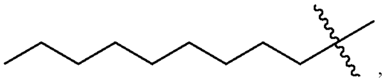

,

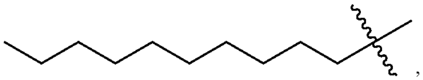

,

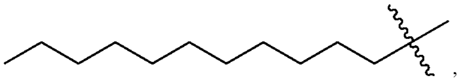

,

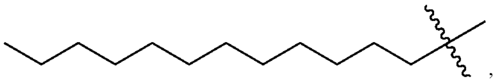

,

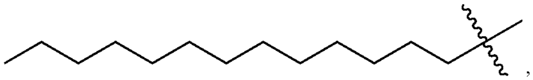

,

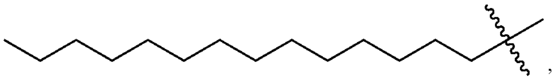

,

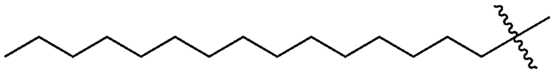

,

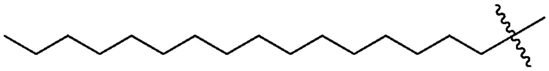

,

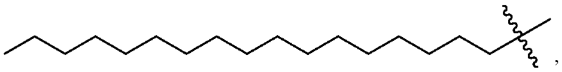

,

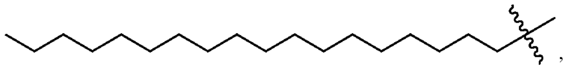

,

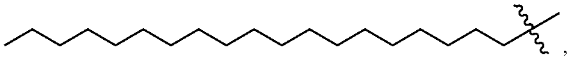

,

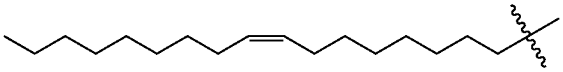

,

-continued

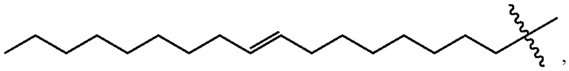
,

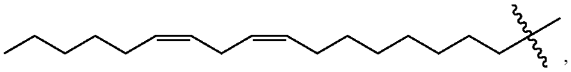
,

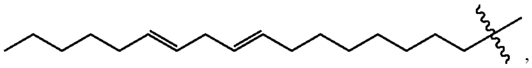
, or

-continued

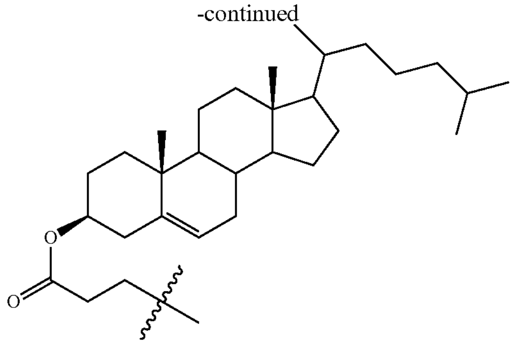
.

In addition, in formula (I), ma is selected from the group consisting of a linear alkyl with 6 carbon atoms, an ether bond-containing linear alkyl with 4 to 8 carbon atoms, or an N-heterocycle-containing alkyl.

In addition, the cationic lipid analog material has a structure selected from the group consisting of the following 72 structures:

I1R1C12A1

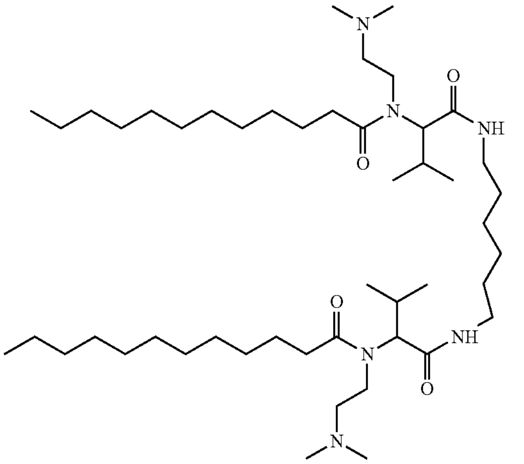

I1R1C14A1

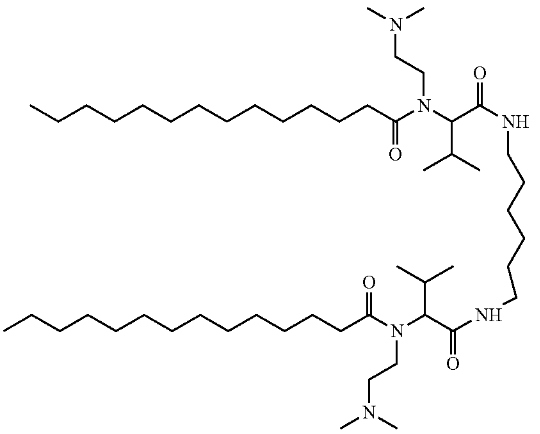

I1R1C16A1

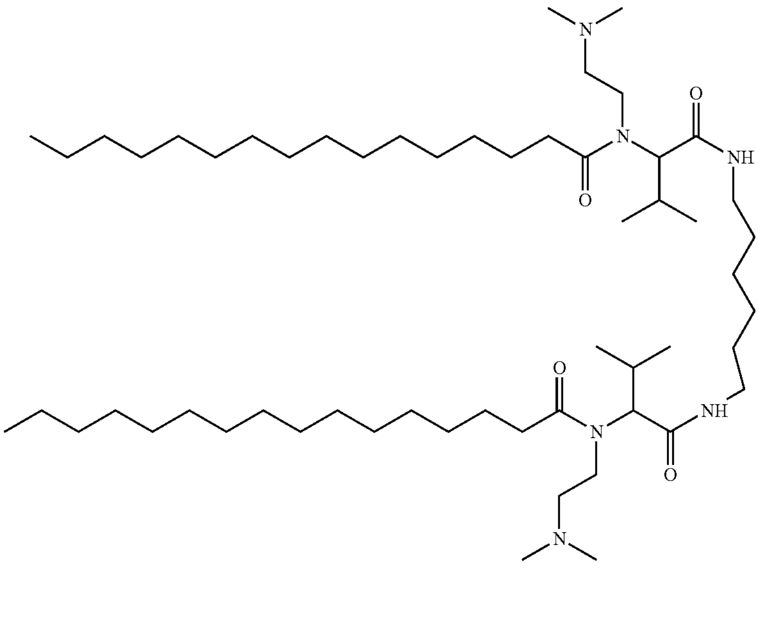

-continued
I1R1C18A1
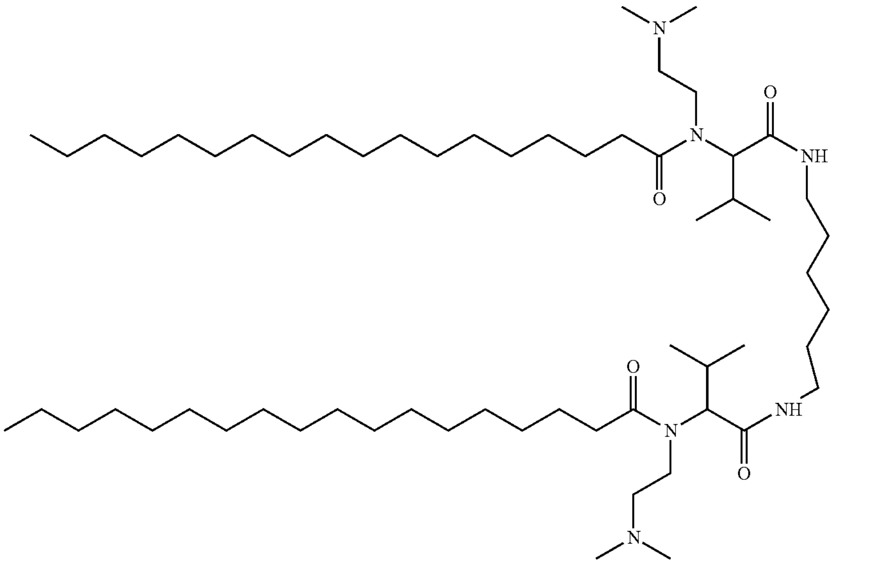
I1R1C20A1
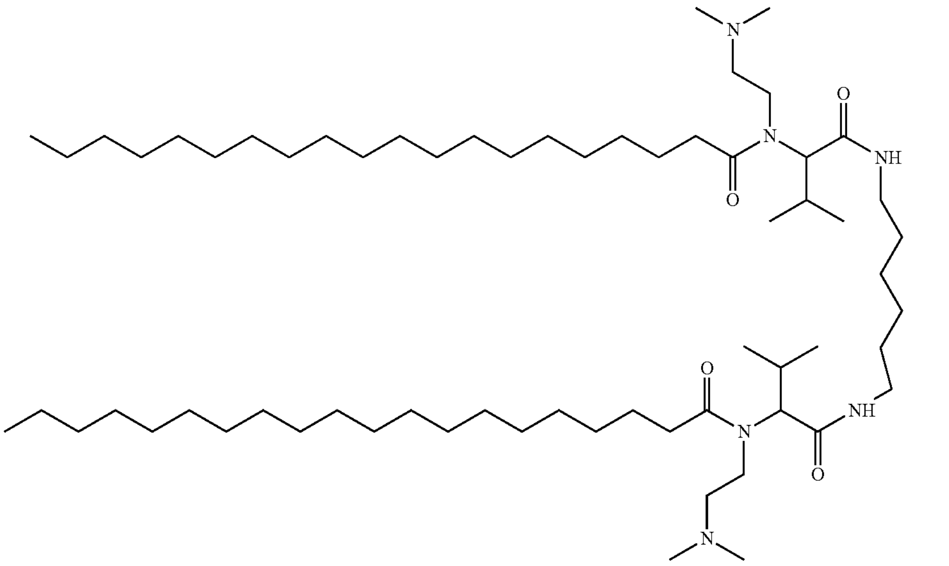

-continued
I1R1C18-1A1
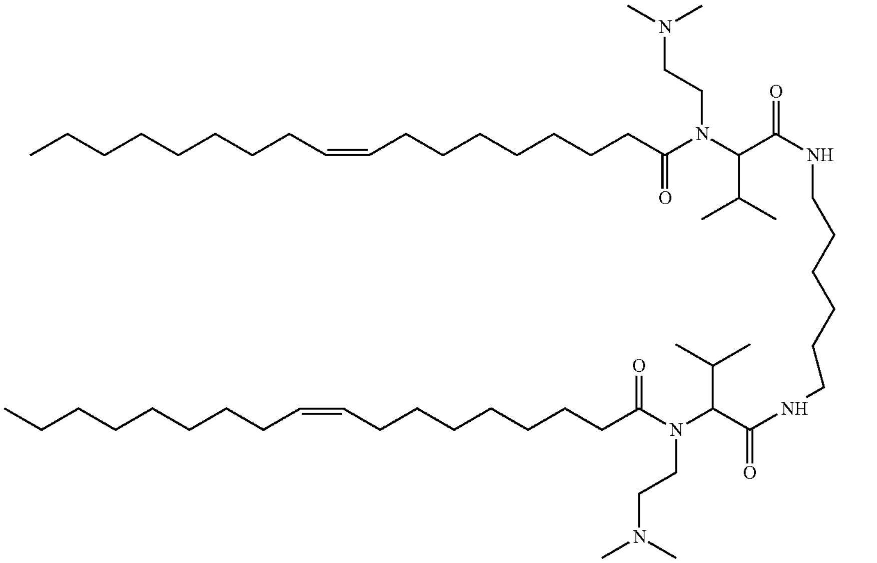
I1R3C14A1
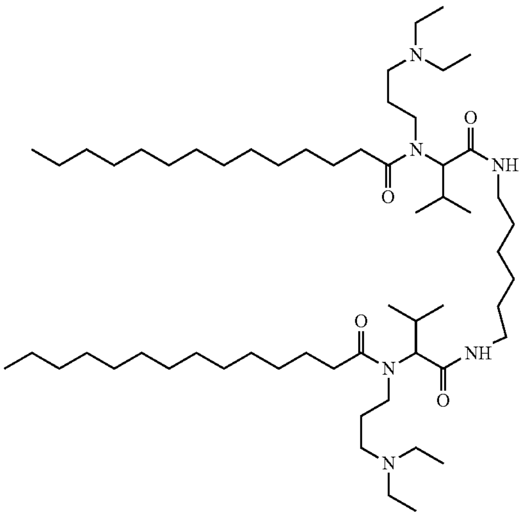
I1R1C18-2A1
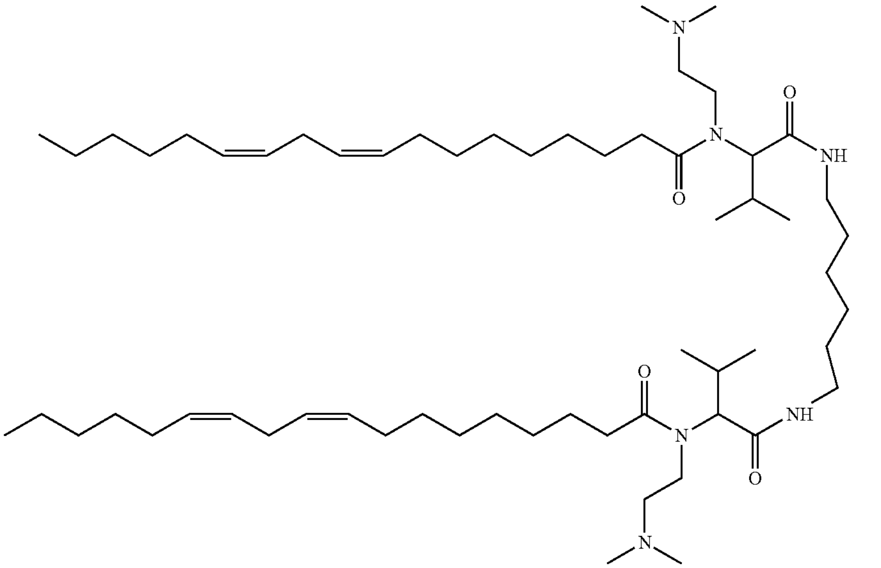

-continued
I1R2C12A1
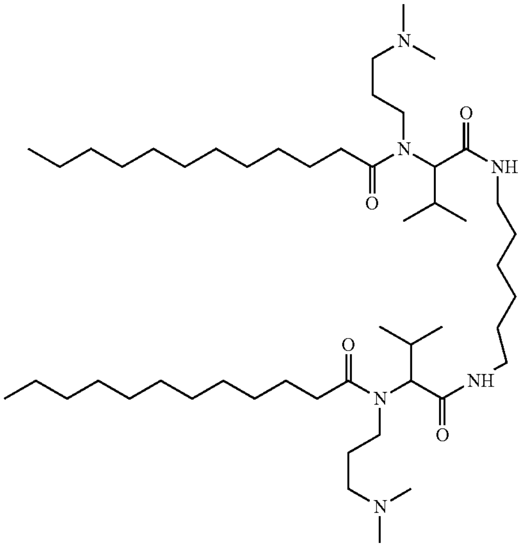
I1R2C14A1
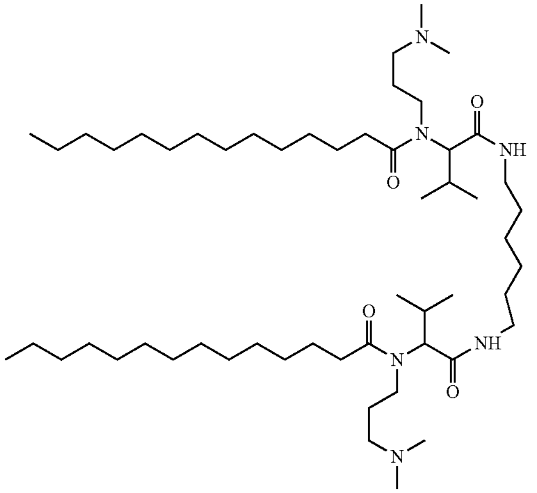
I1R2C16A1
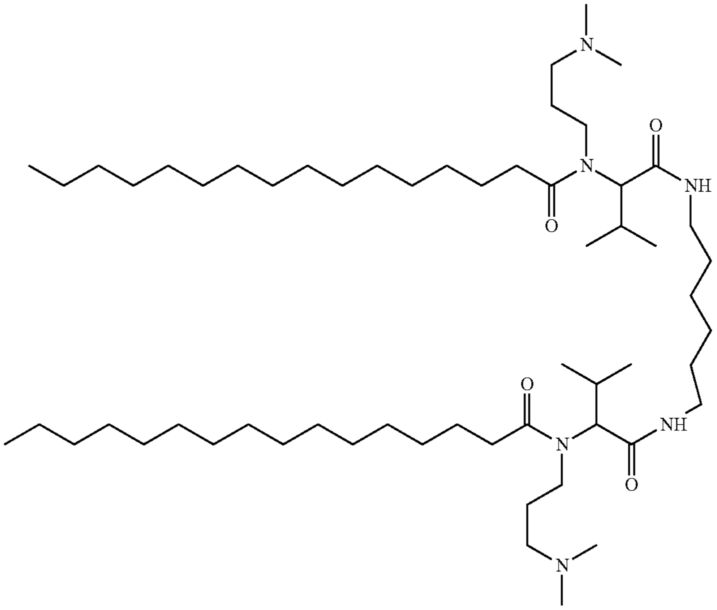

-continued
I1R2C18A1
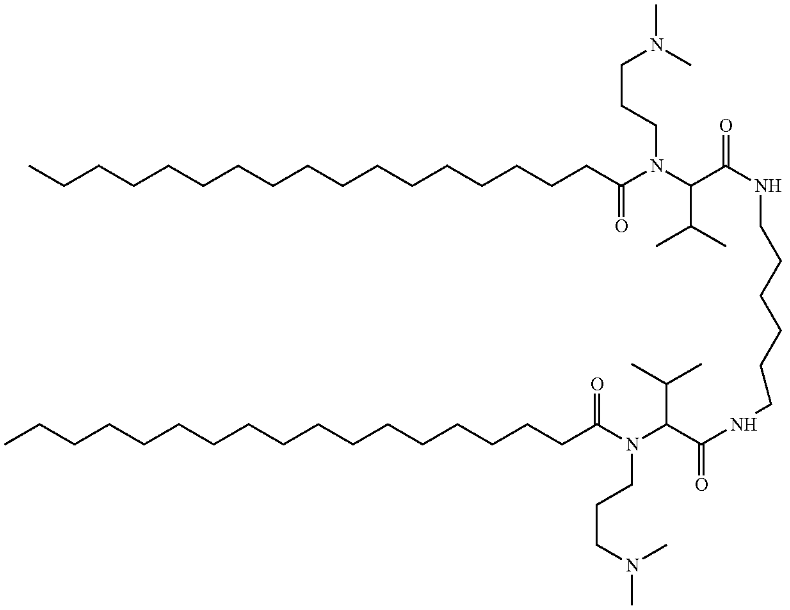
I1R2C20A1
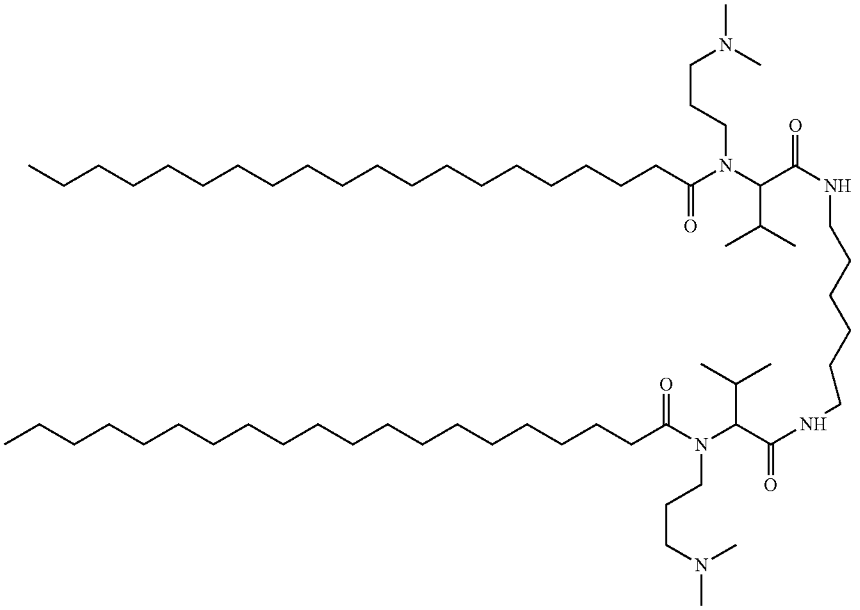

-continued
I1R2C18-1A1
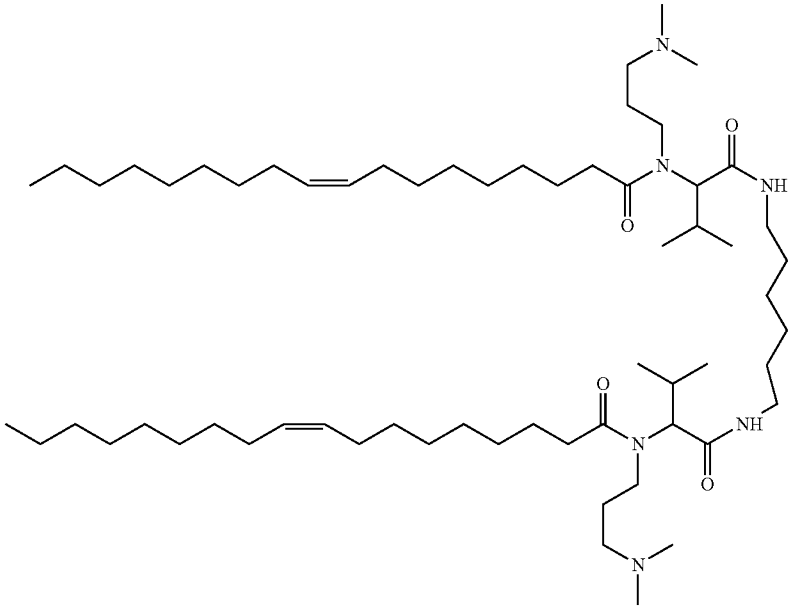
I1R2C18-2A1
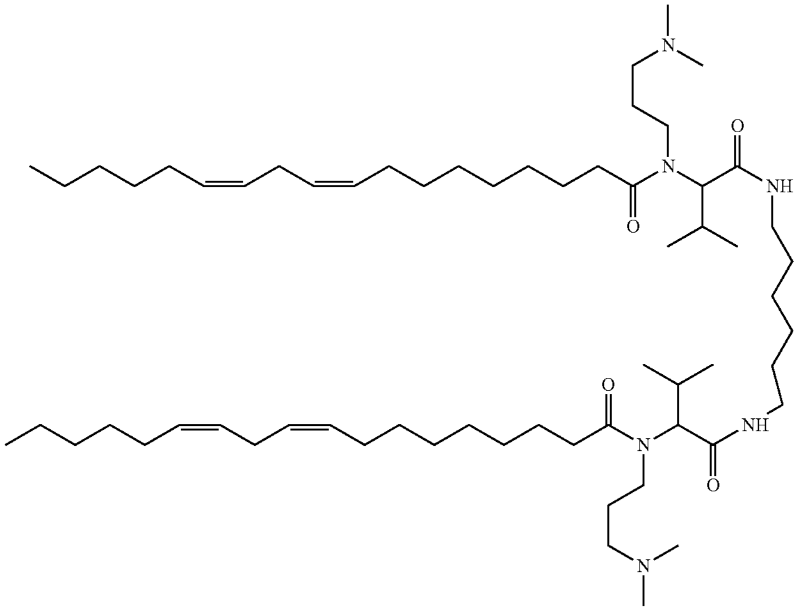

-continued
I1R3C12A1
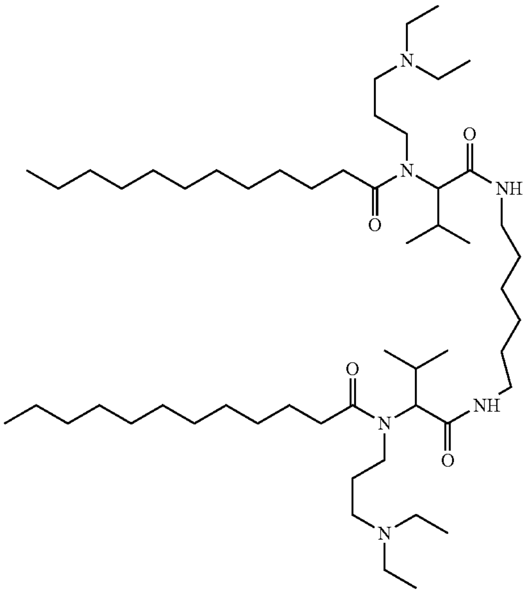
I1R3C16A1
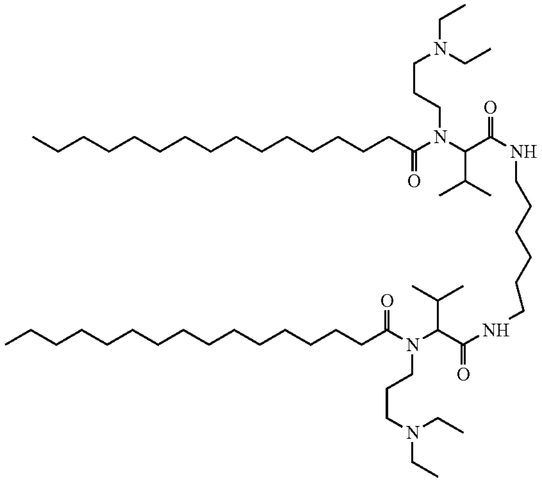
I1R3C18A1
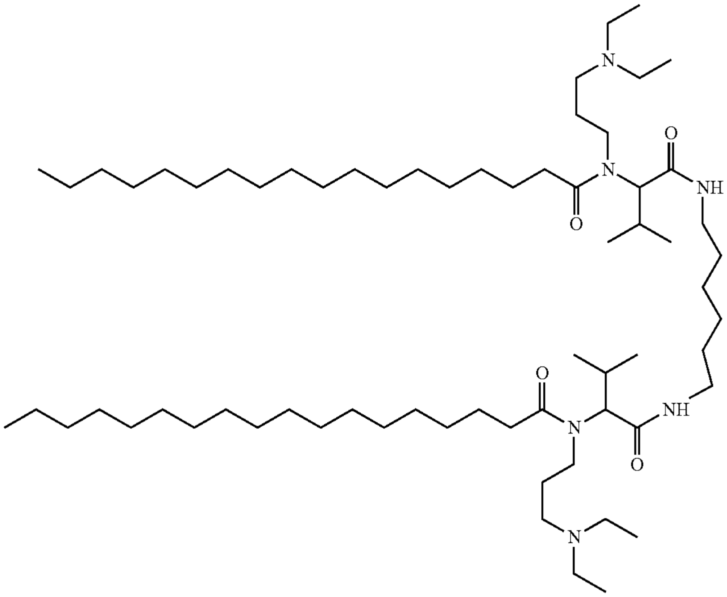

-continued
I1R3C20A1
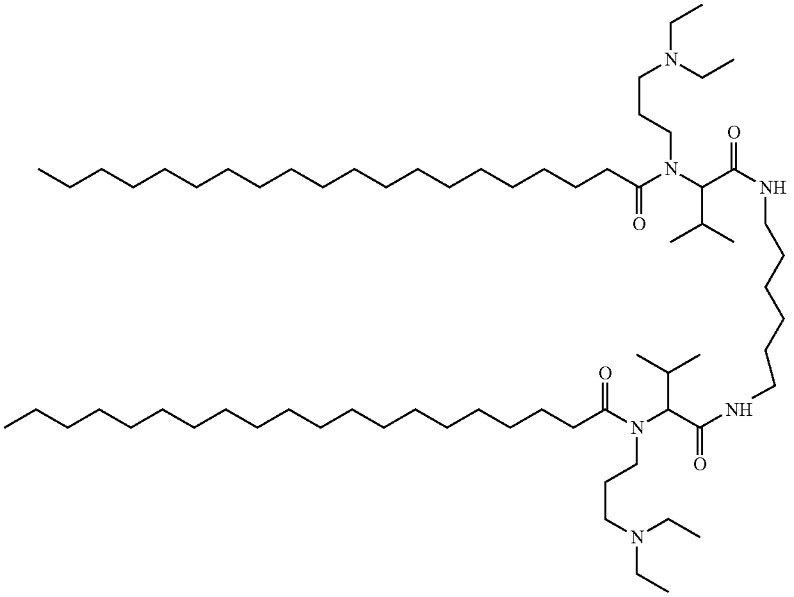
I1R3C18-1A1
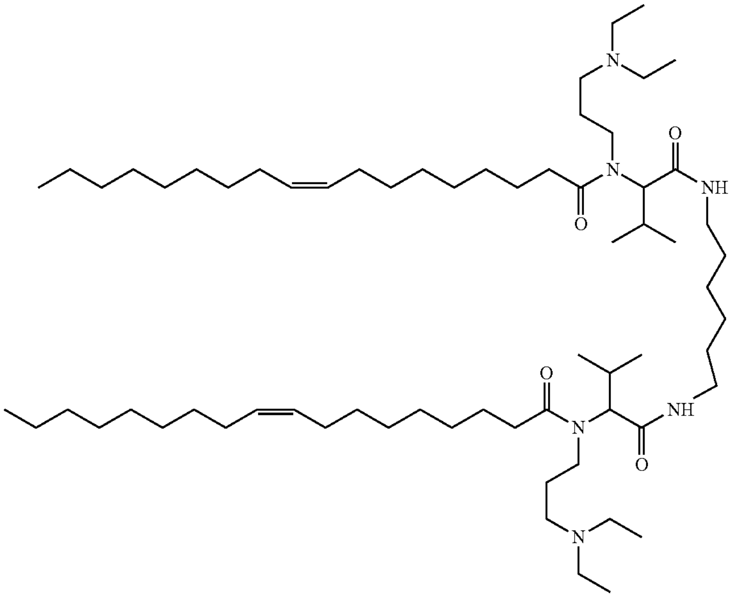

-continued
I1R3C18-2A1
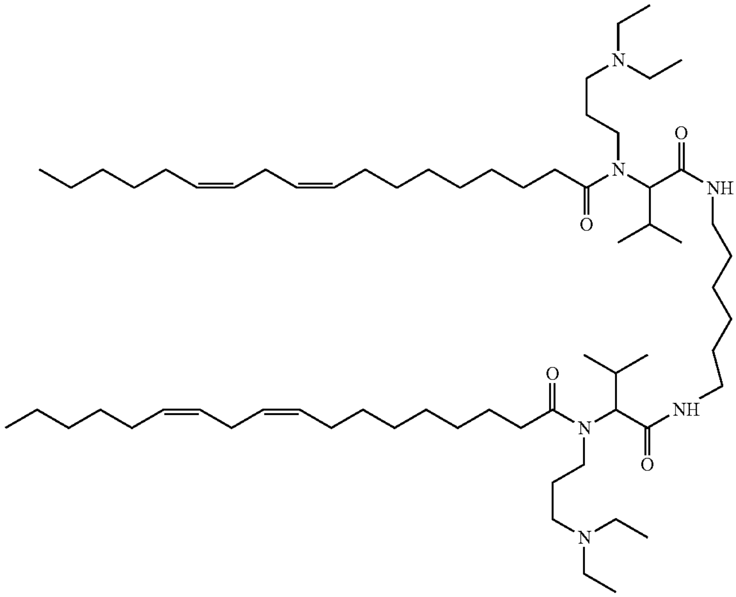
I1R5C12A1
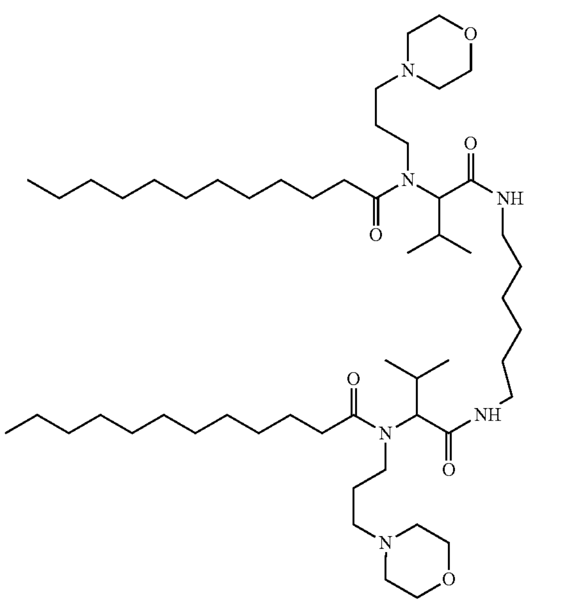
I1R5C14A1
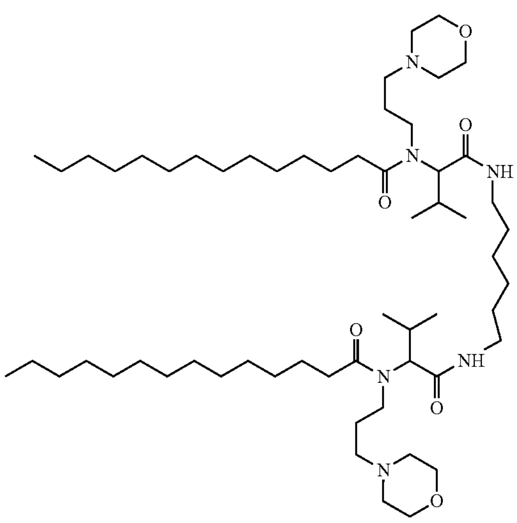

-continued
I1R5C16A1
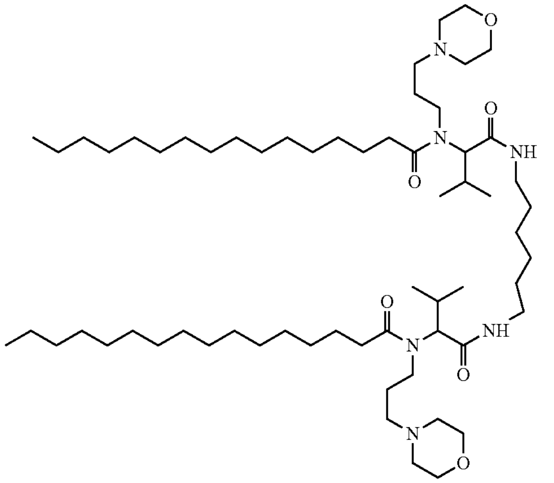
I1R5C18A1
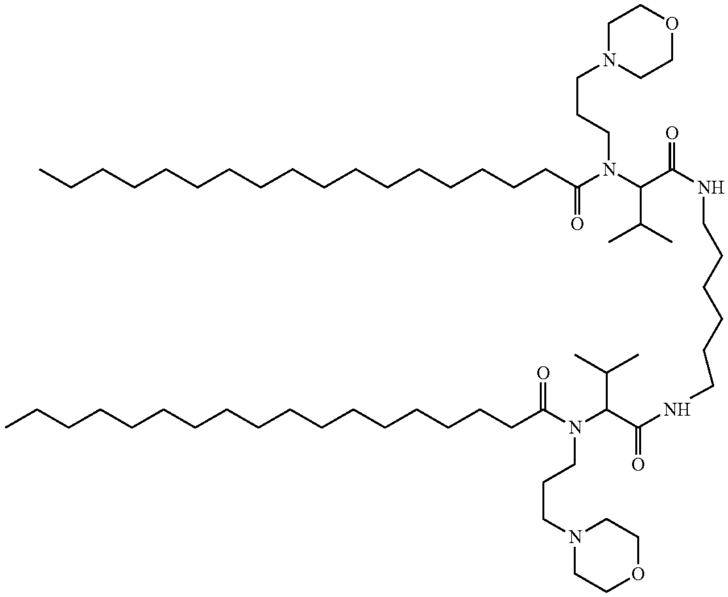

-continued
I1R5C20A1
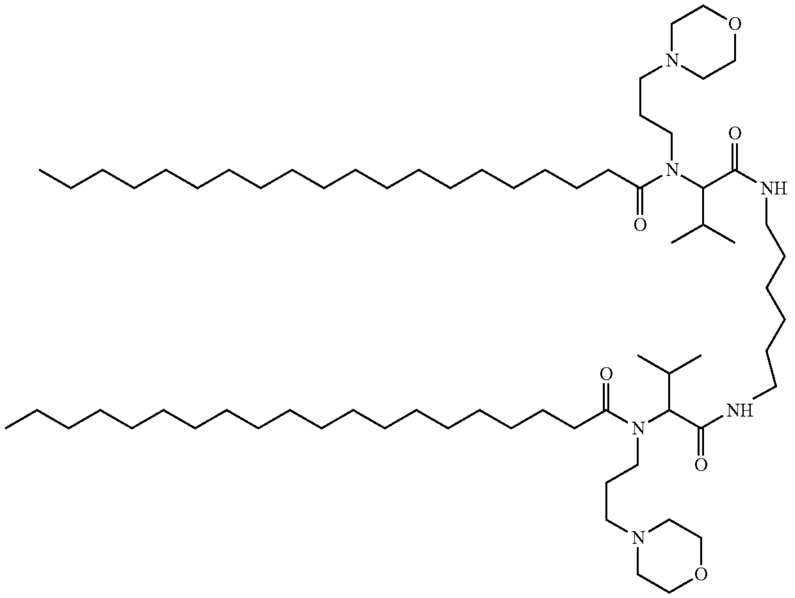
I1R5C18-1A1
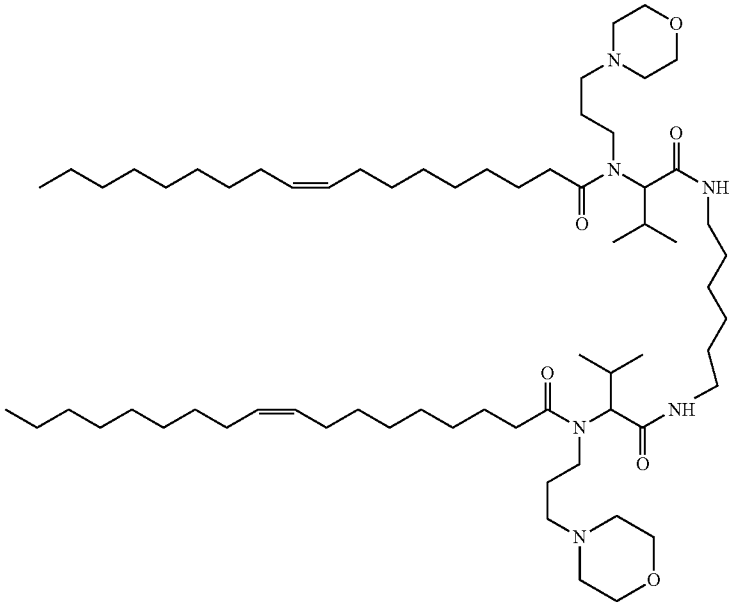

-continued
I1R5C18-2A1
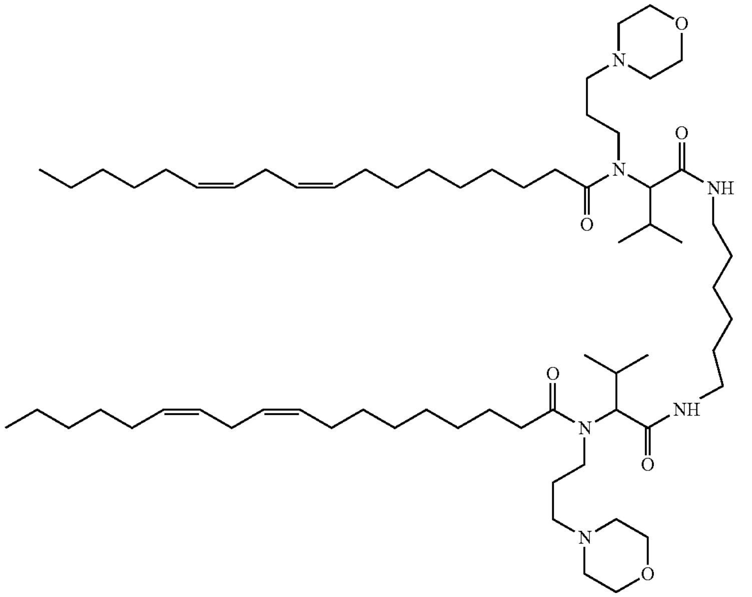
I1R11C12A1
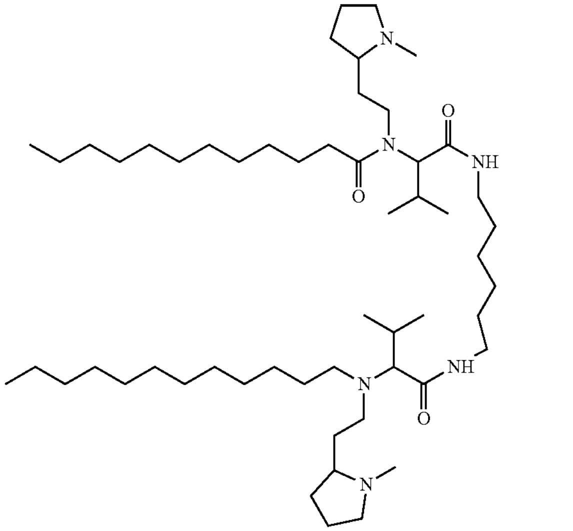
I1R11C14A1
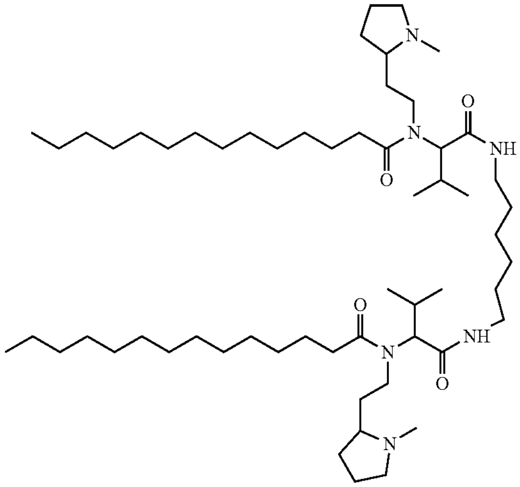

-continued
I1R11C16A1
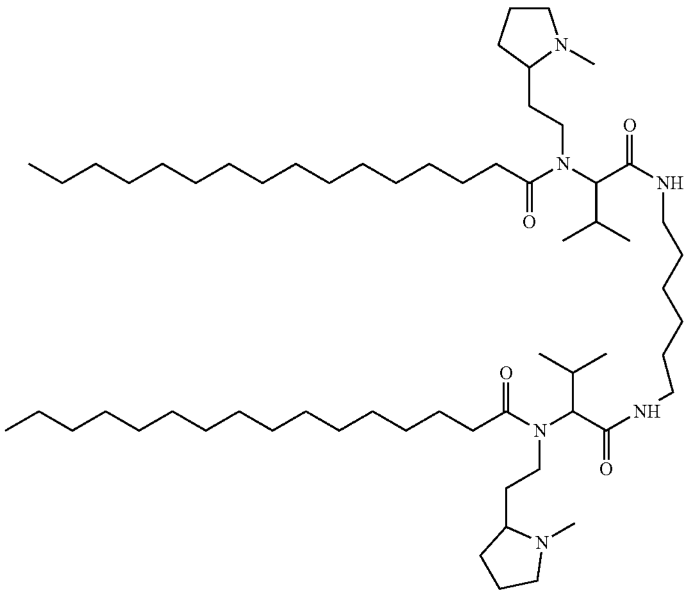
I1R11C18A1
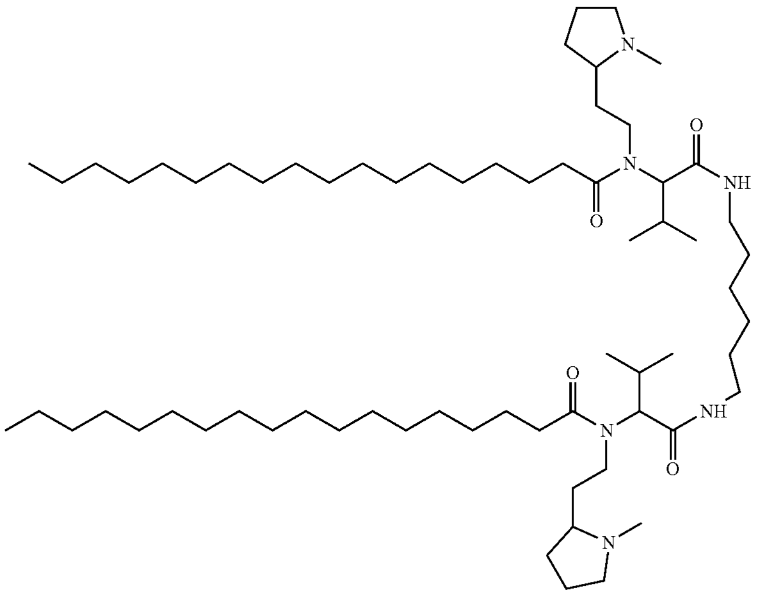

-continued
I1R11C20A1
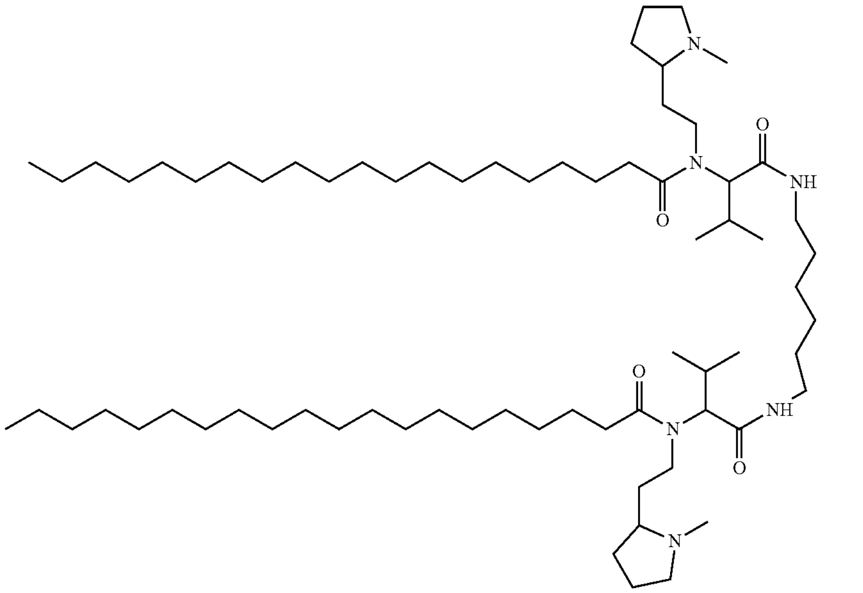
I1R11C18-1A1
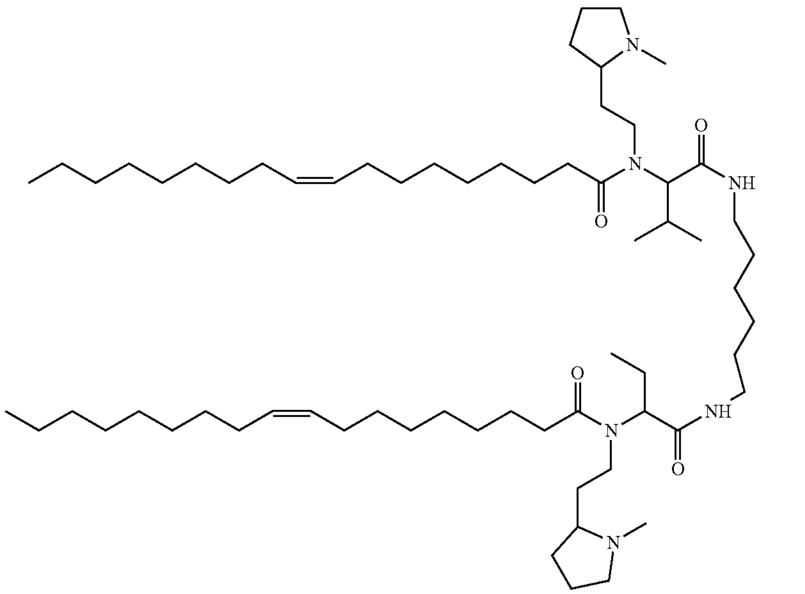

-continued
I1R11C18-2A1
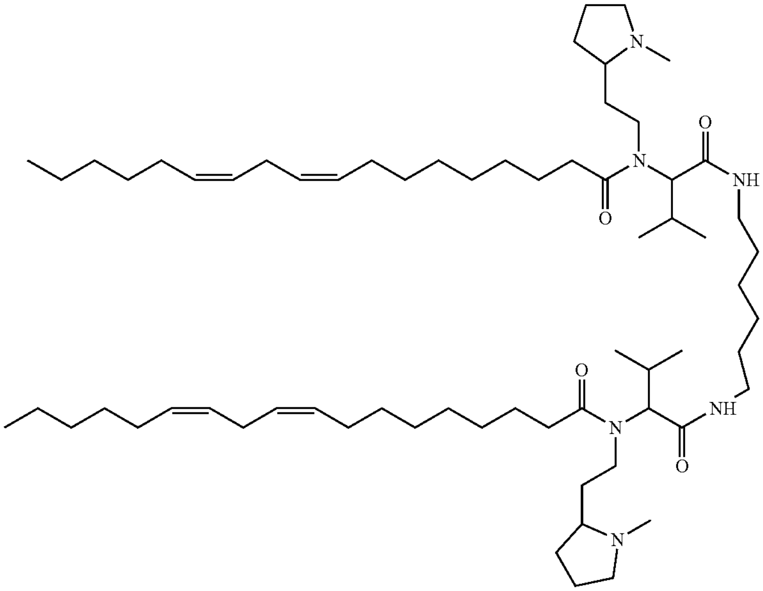
I2R1C12A1
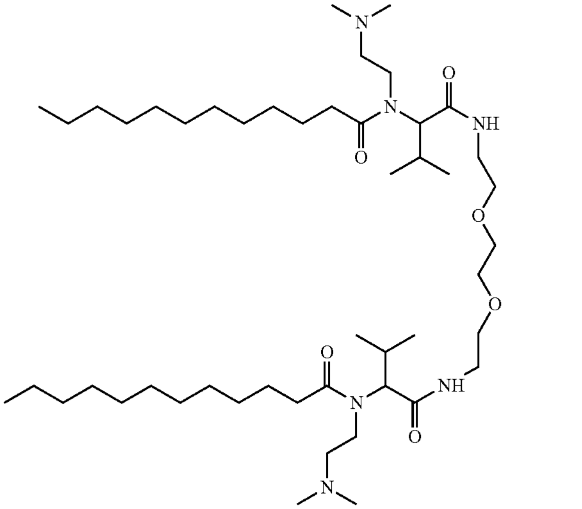
I2R1C14A1
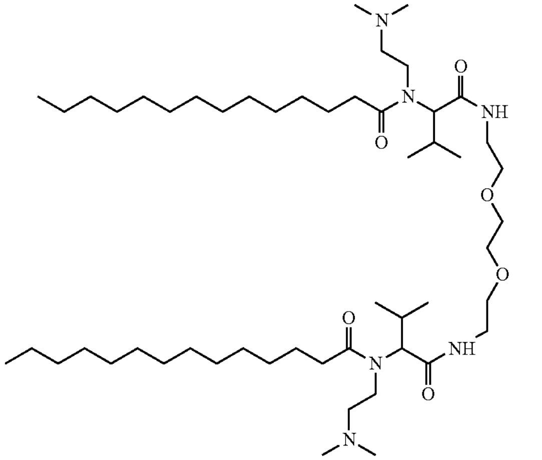

-continued
I2R1C16A1
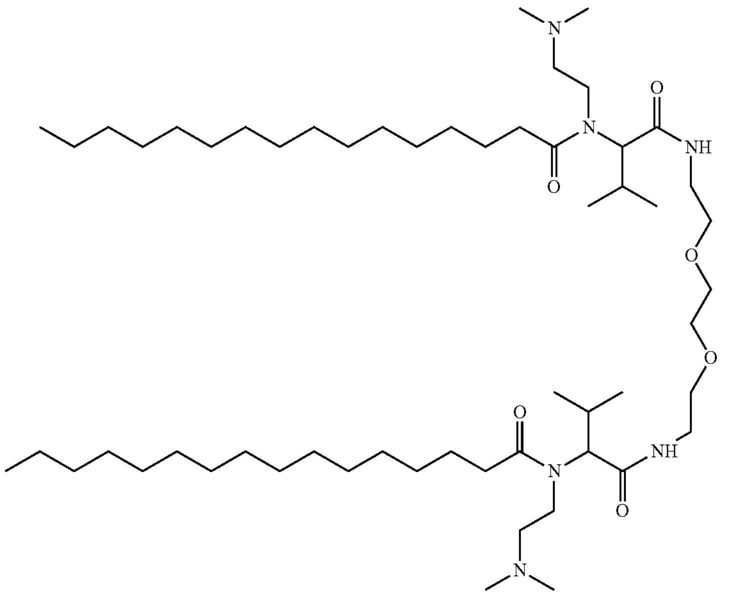
I2R1C18A1
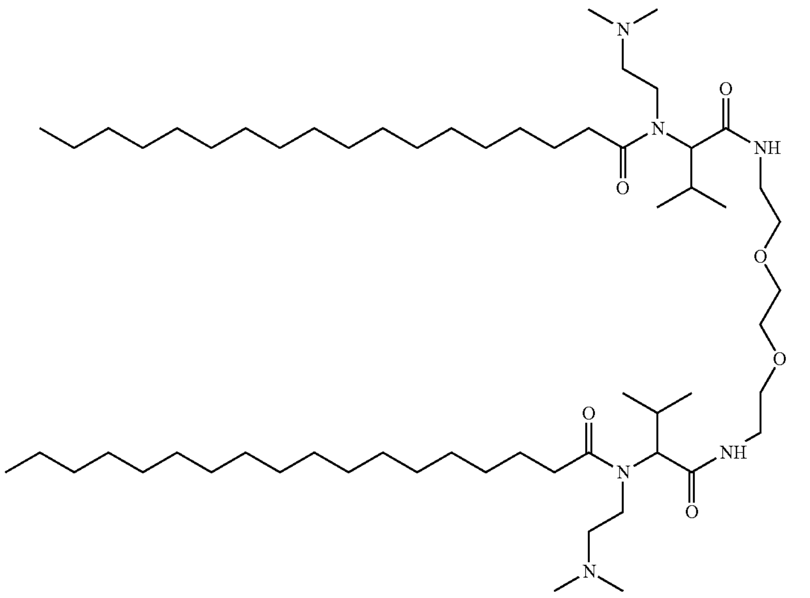

-continued
I2R1C20A1
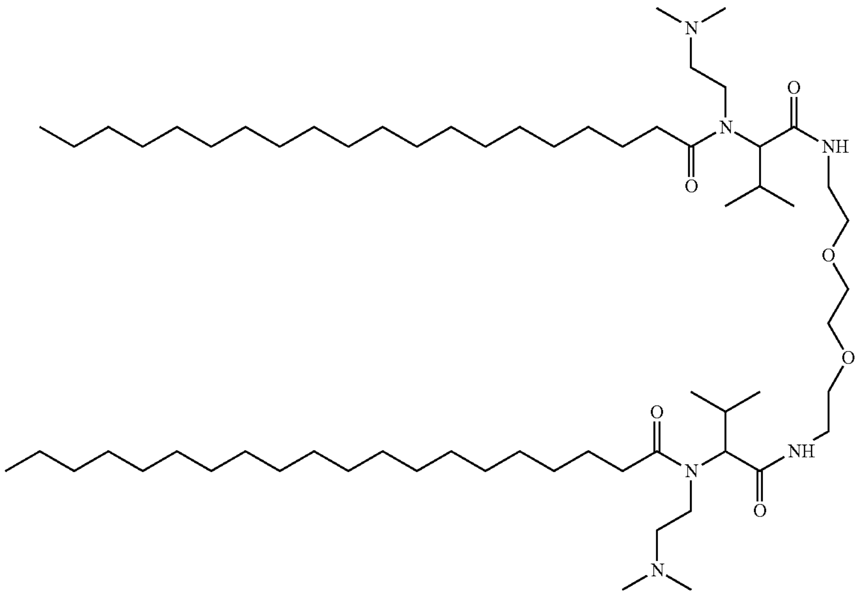
I2R1C18-1A1
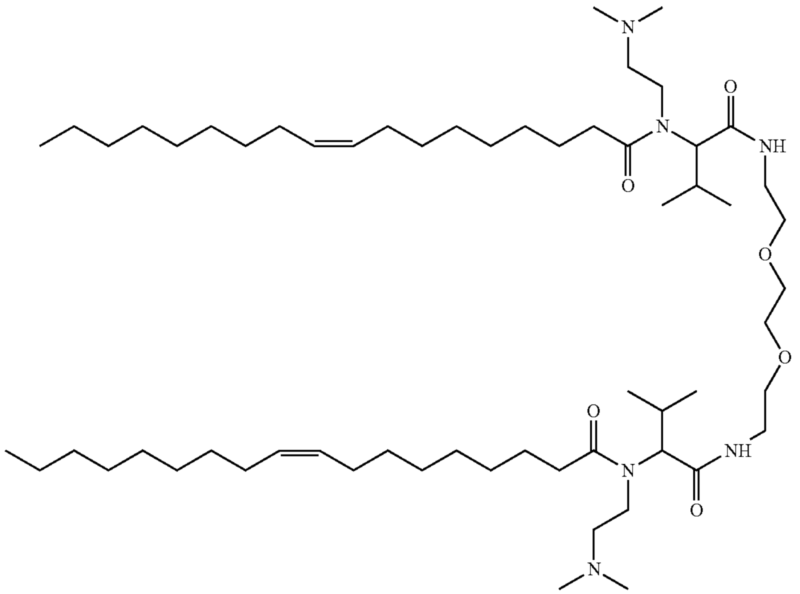

-continued
I2R1C18-2A1
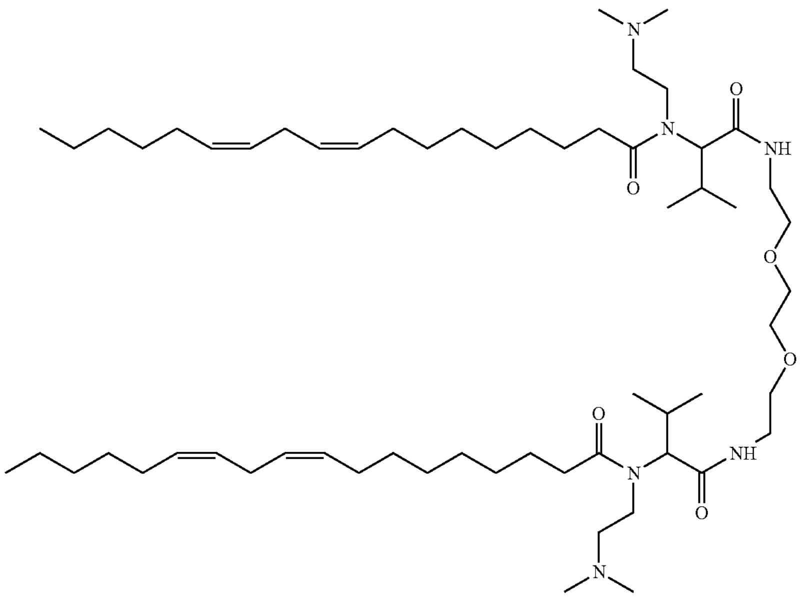
I2R2C12A1
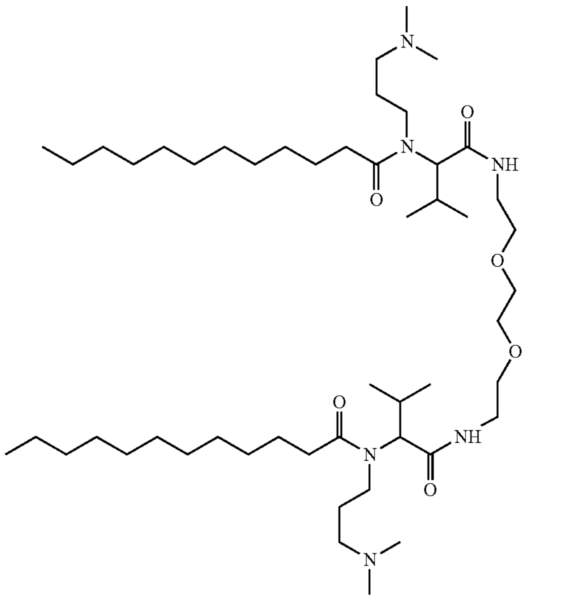
I2R2C14A1
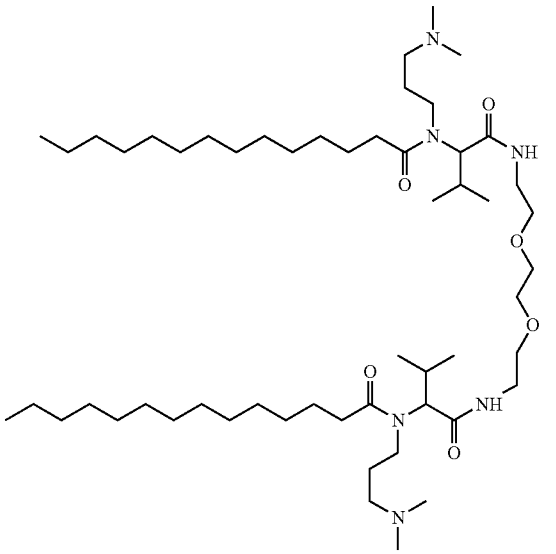

-continued
I2R2C16A1
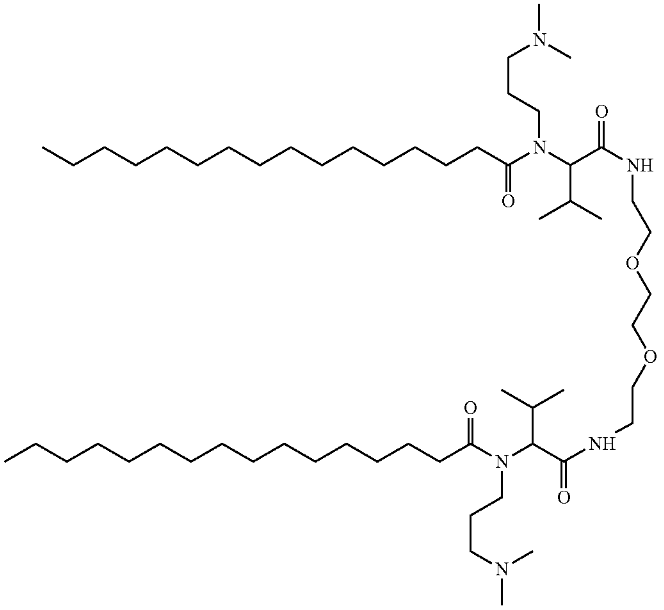
I2R2C18A1
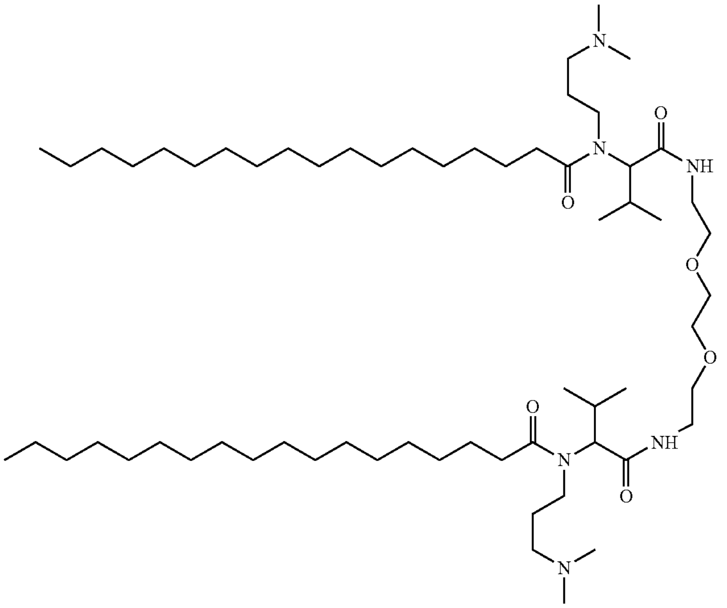

-continued
I2R2C20A1
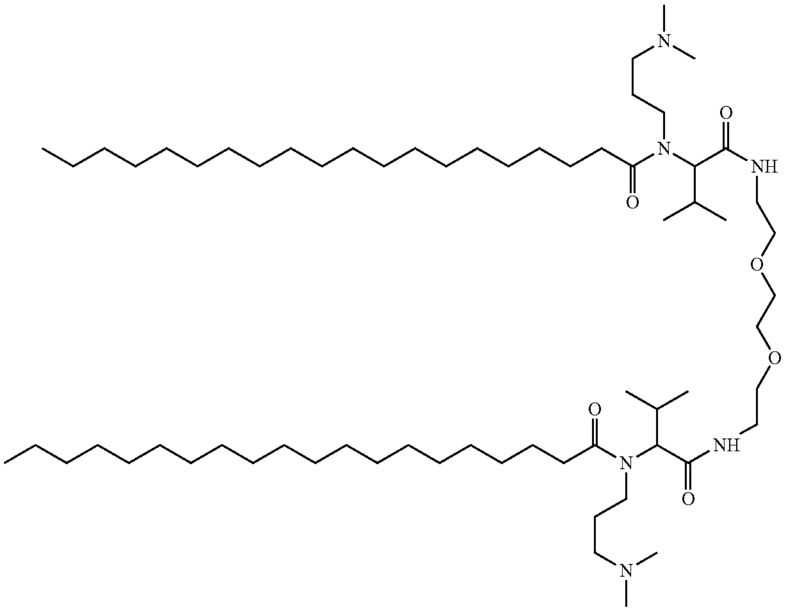
I2R2C18-1A1
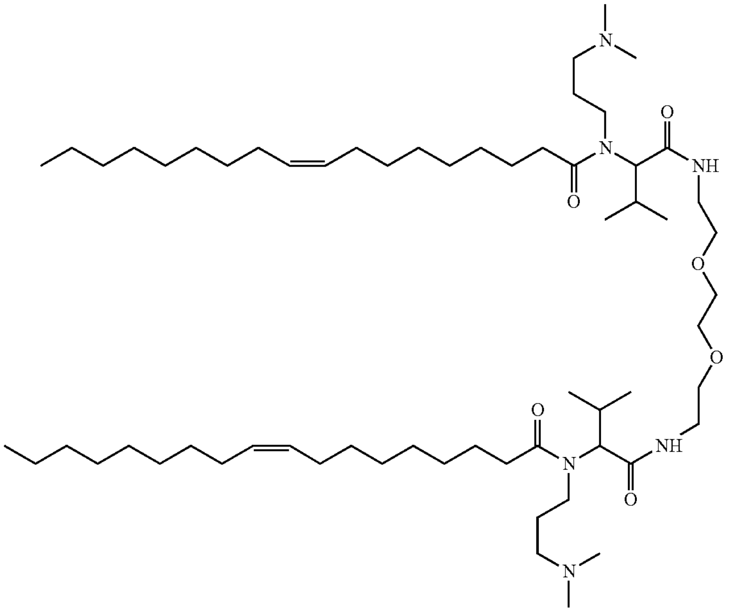

-continued
I2R2C18-2A1
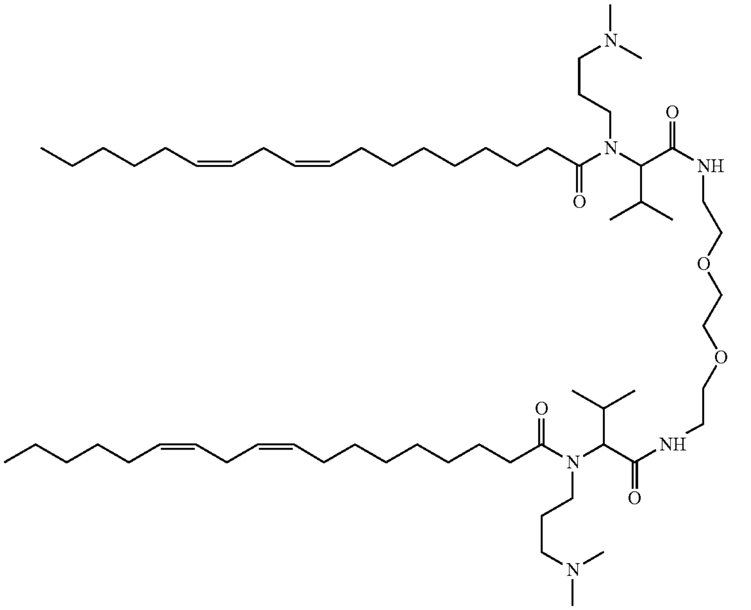
I2R3C12A1
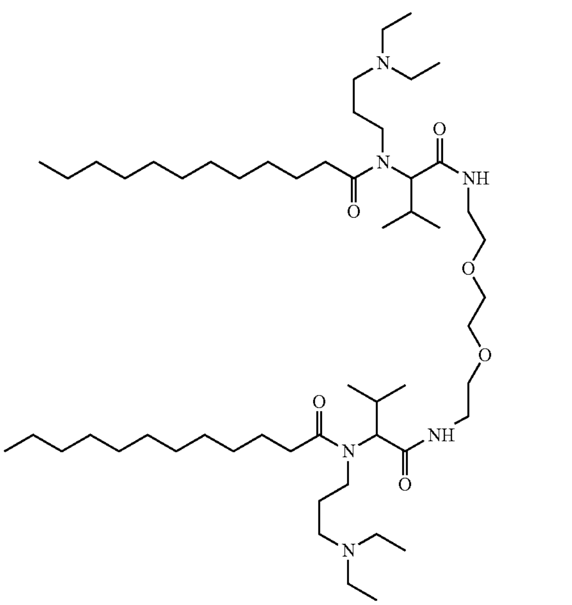
I2R3C14A1
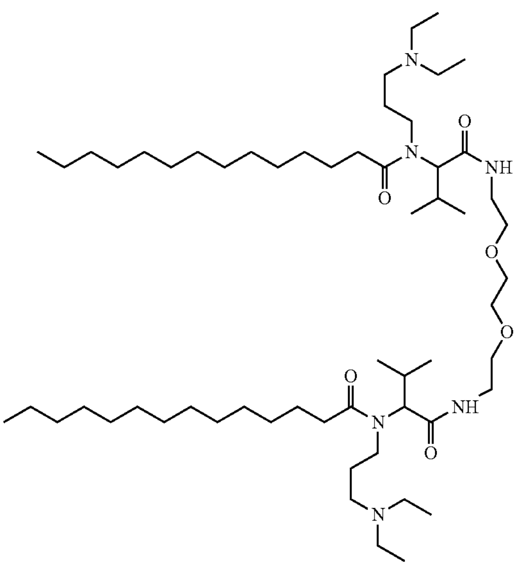

-continued
I2R3C16A1
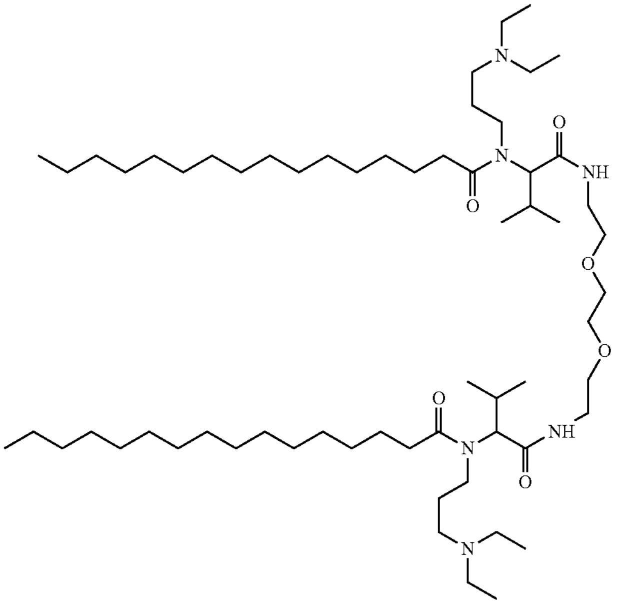
I2R3C18A1
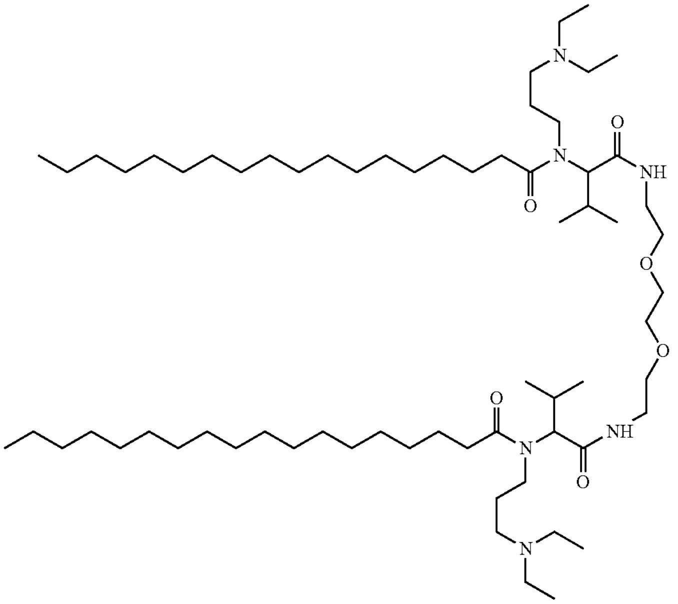

-continued
I2R3C20A1
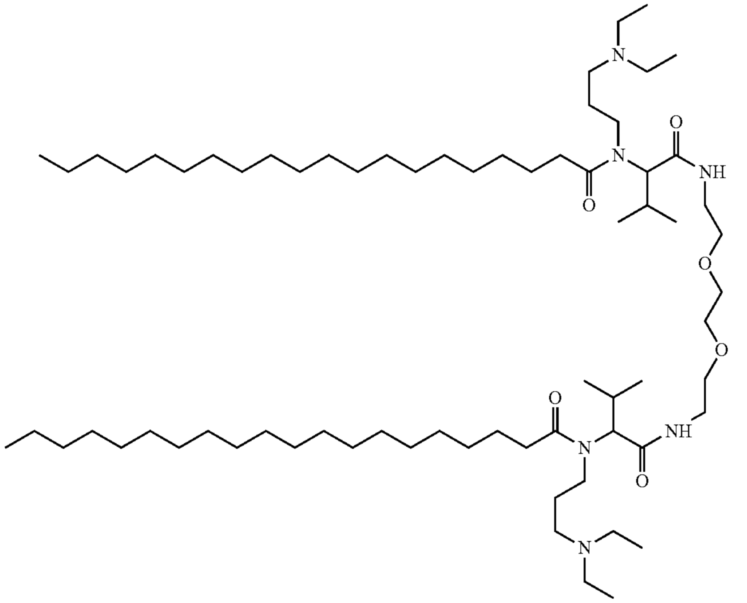
I2R3C18-1A1
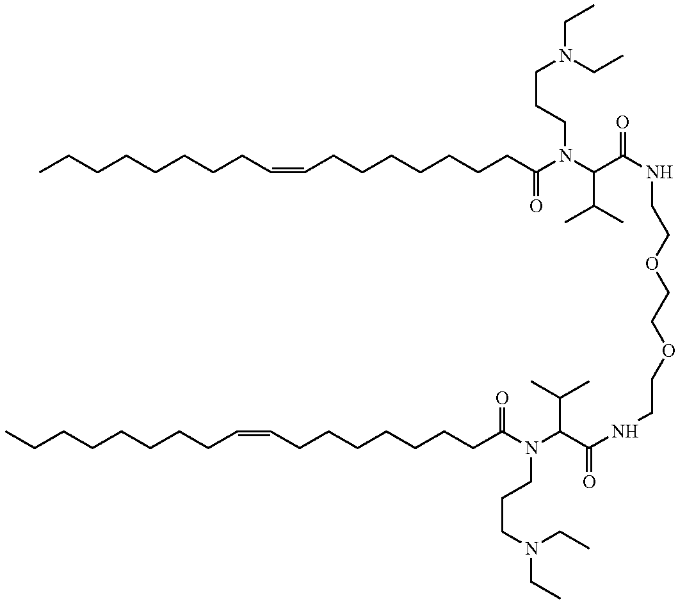

-continued
I2R3C18-2A1
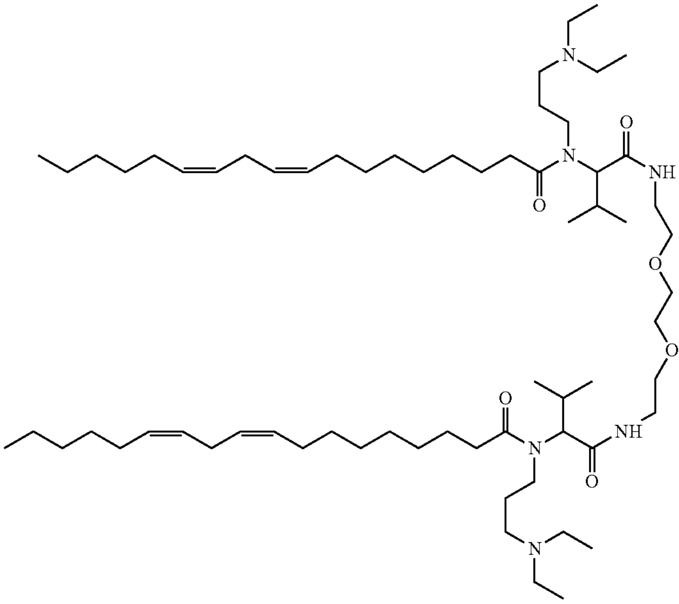
I2R5C12A1
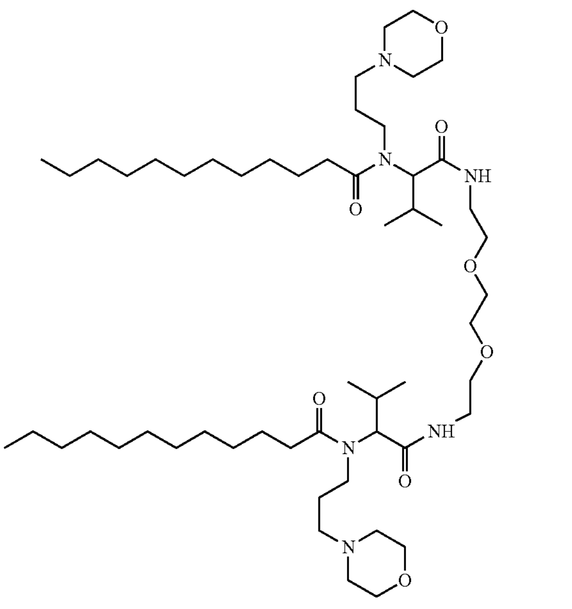
I2R5C14A1
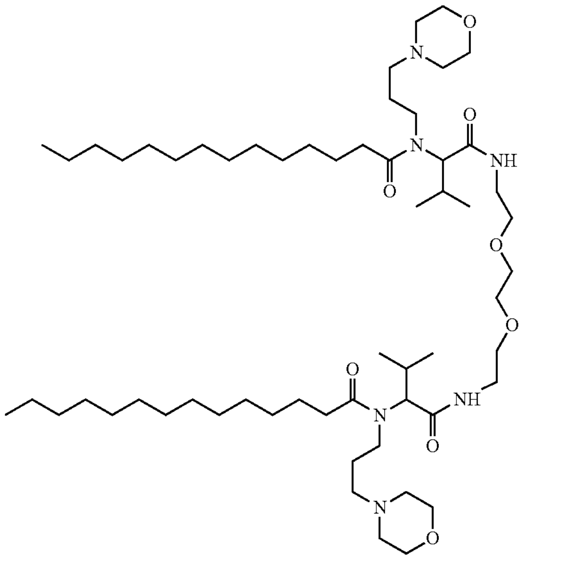

-continued
I2R5C16A1
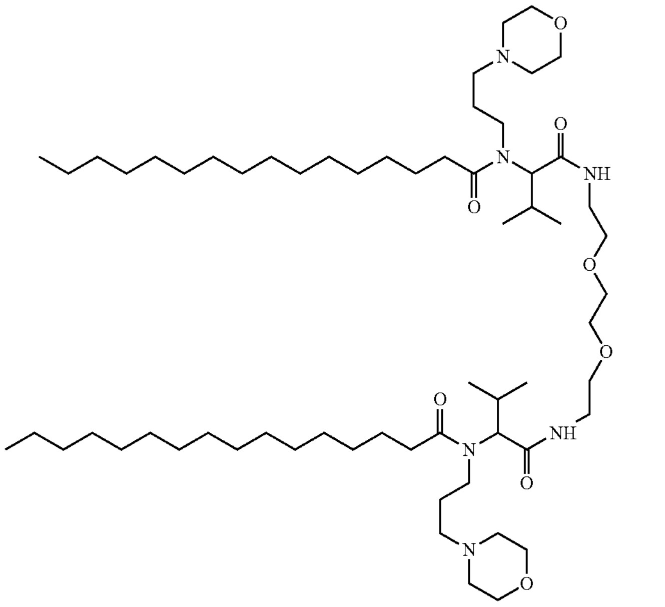
I2R5C18A1
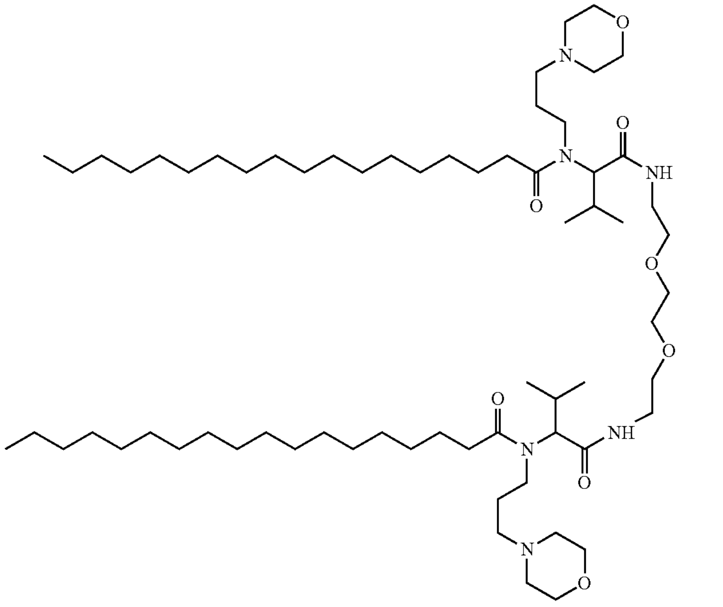

-continued
I2R5C20A1
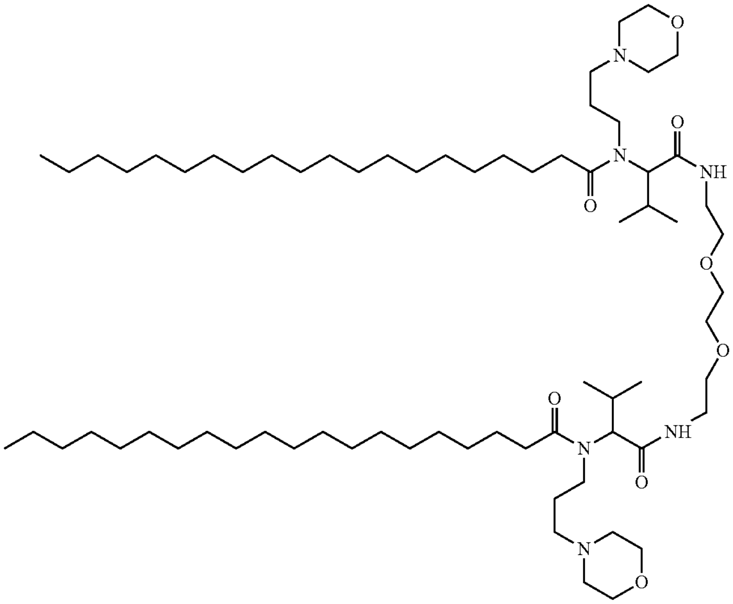
I2R5C18-1A1
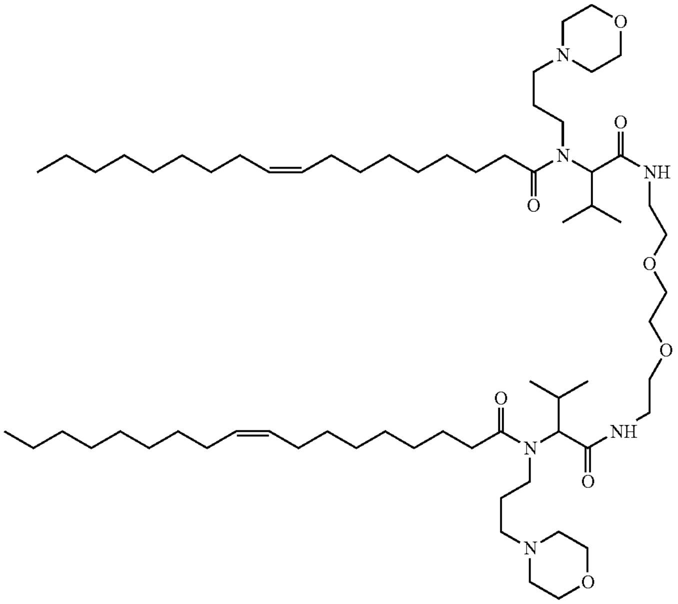

-continued
I2R5C18-2A1
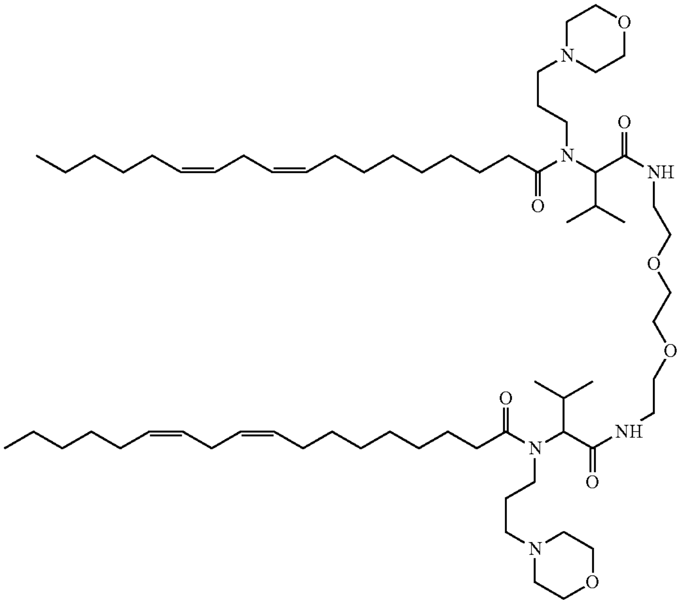
I2R11C12A1
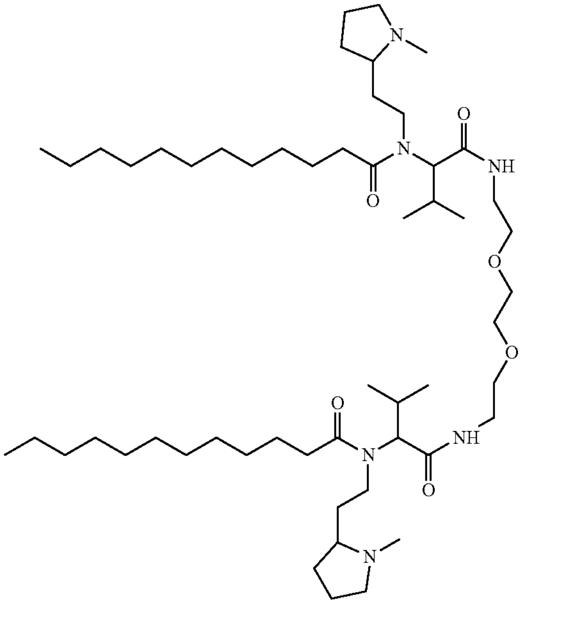
I2R11C14A1
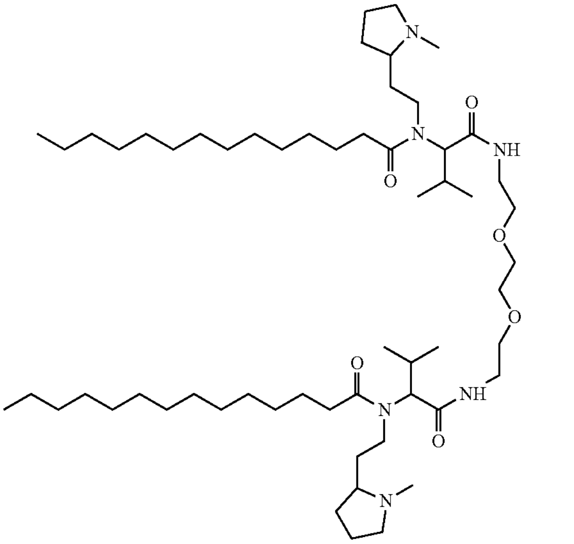

-continued
I2R11C16A1
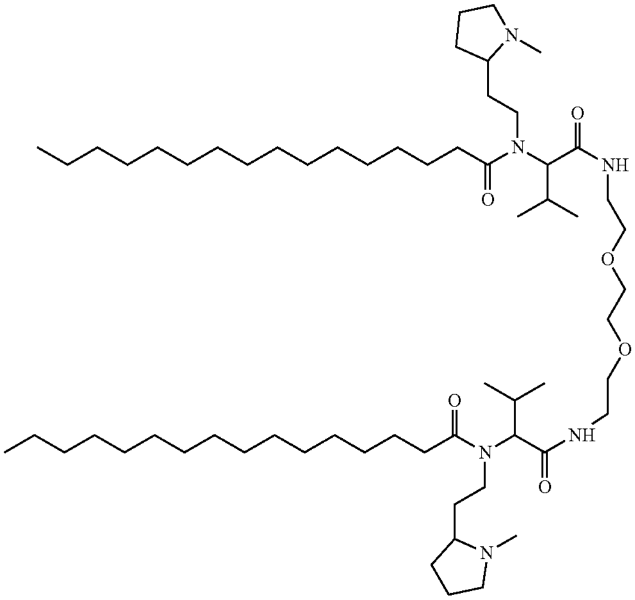
I2R11C18A1
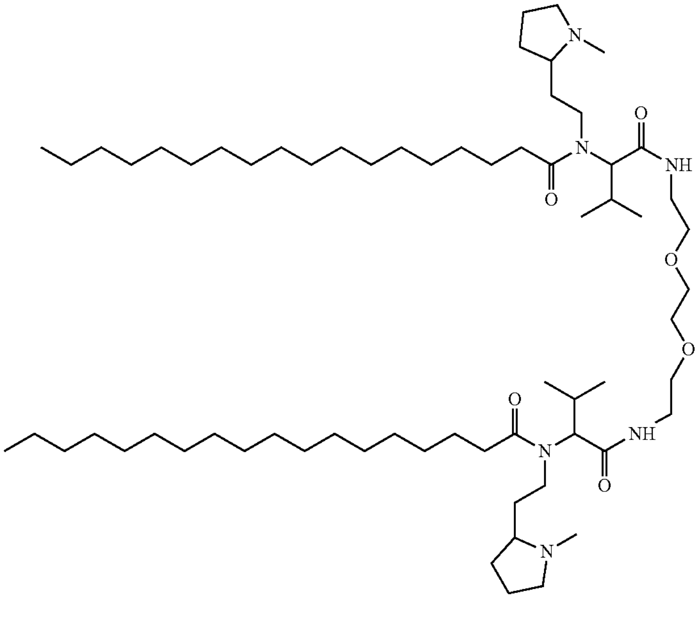

-continued
I2R11C20A1
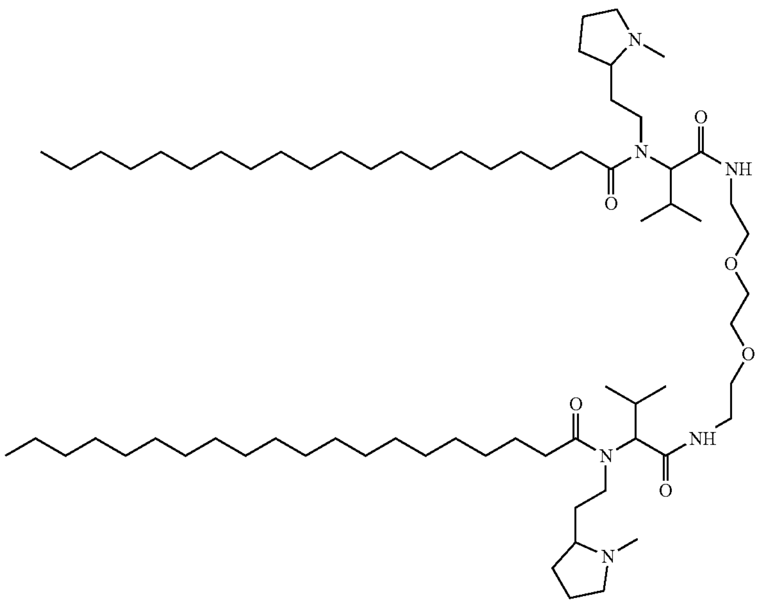
I2R11C18-1A1
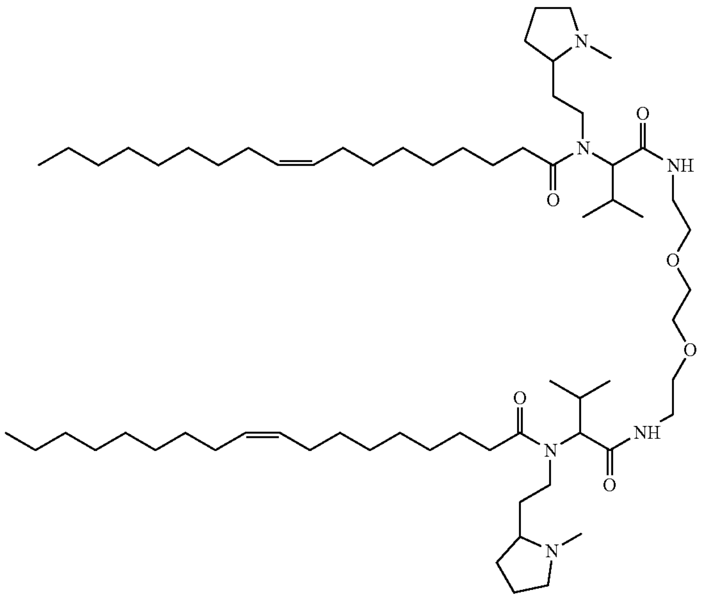

-continued
I2R11C18-2A1
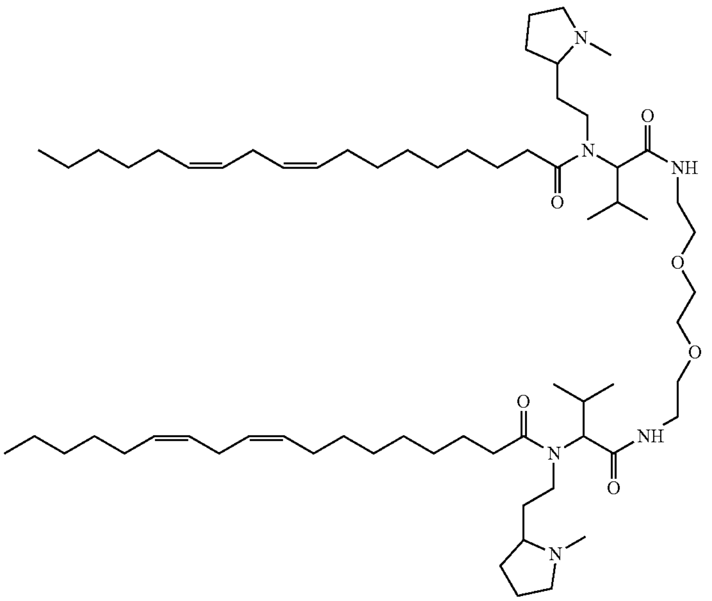
I2-1R2C18A1
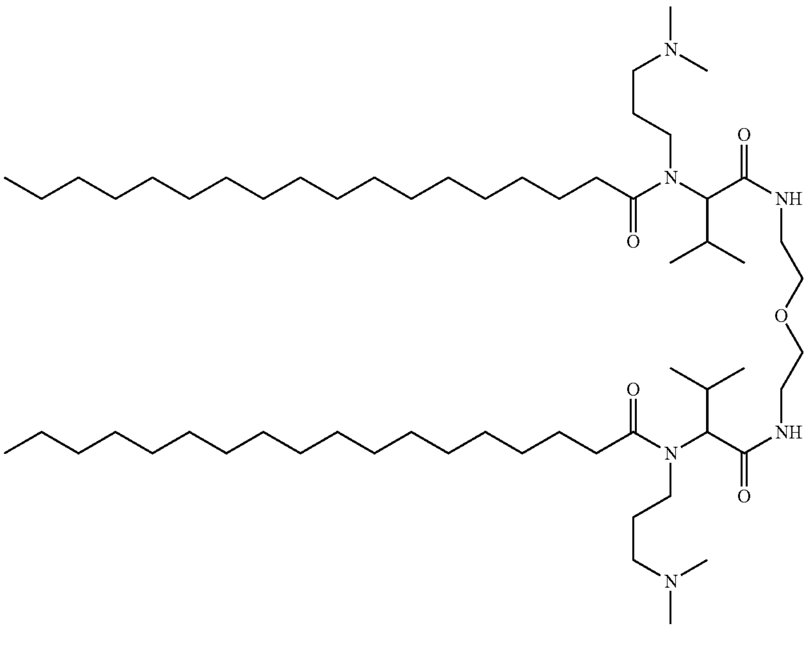

-continued

I2-3R2C18A1

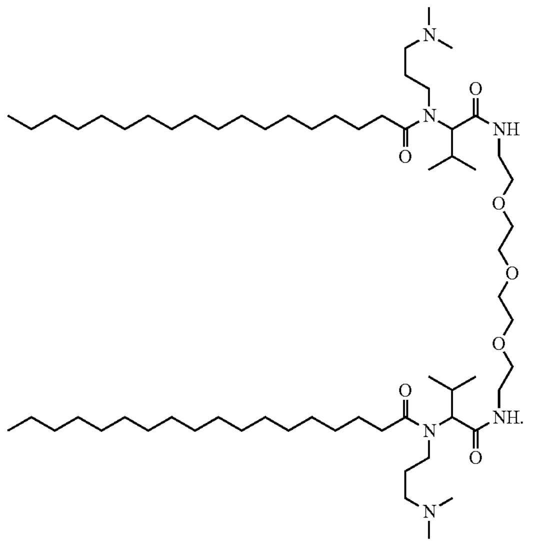

Through the screening of different cationic lipid analog materials, the present application finds that the delivery effect of nucleic acids is related to the structure of cationic lipid analog materials, and the above 72 small-molecule cationic lipid analog materials can combine with a variety of nucleic acid molecules to form nanoparticles and achieve efficient intracellular delivery of plasmid DNA, mRNA and siRNA. Moreover, the cationic lipid analog materials above have low cytotoxicity.

In addition, the cationic lipid analog material is at least one selected from the group consisting of I1R2C14A1, I1R2C18-2A1, I1R11C14A1, I2R1C14A1, I2R1C16A1, I2R1C18-1A1, I2R1C18-2A1, I2R2C14A1, I2R2C16A1, I2R2C18-1A1, I2R2C18-2A1, I2R3C16A1, I2R3C18A1, I2R3C18-1A1, I2R3C18-2A1, I2R11C14A1, I2R11C16A1, I2R11C18A1, I2R11C18-1A1, I2R11C18-2A1. The present application uses green fluorescent protein (GFP)-expressing plasmid DNA or luciferase (luminescence)-expressing plasmid DNA as a reporter gene to detect the gene transfection efficiency of different cationic lipid analog materials in Hela cells. The results show that the above 20 cationic lipid analog materials have high transfection efficiency, and their transfection efficiency reaches or is higher than that of the commercial transfection reagent Lipofectamine 2000.

In addition, the cationic lipid analog material is at least one selected from the group consisting of I1R2C14A1, I1R2C16A1, I1R2C18A1, I1R2C18-1A1, I1R2C18-2A1, I1R11C14A1, I1R11C16A1, I1R11C18A1, I2R1C14A1, I2R1C16A1, I2R1C18-1A1, I2R2C14A1, I2R2C16A1, I2R2C18A1, I2R2C18-1A1, I2R2C18-2A1, I2R3C14A1, I2R3C16A1, I2R3C18A1, I2R3C18-1A1, I2R3C18-2A1, I2R11C14A1, I2R11C16A1, I2R11C18A1, I2R11C18-1A1, I2R11C18-2A1. In this application, eGFP-mRNA is selected as the model mRNA, and the mRNA transfection efficiency of different cationic lipid analog materials is compared in DC 2.4 cells, and the results show that the above cationic lipid analog materials have high transfection efficiency.

In addition, the cationic lipid analog material is at least one selected from the group consisting of I2R2C18-1A1, I2R2C18-2A1, I2R3C18-1A1, I2R3C18-2A1. In this application, the siRNA transfection and delivery effect of cationic lipid analog materials is detected in A549 cells (A549-Luc), and the above four materials could deliver siRNA, which can achieve efficient gene silencing.

In addition, there is no special limit on the type or structure of the nucleic acids used in the present application. The nucleic acids include, but are not limited to, at least one selected from the group consisting of messenger RNA (mRNA), small interference RNA (siRNA), short hairpin RNA (shRNA), microRNA (miRNA), guide RNA (gRNA), CRISPR RNA (crRNA), trans-activating CRISPR RNA (tracrRNA), plasmid DNA (pDNA), minicircle DNA, genomic DNA (gNDA). The nucleic acids used in the present application may be nucleic acids from a human, an animal, a plant, a bacterium, a virus, etc., or nucleic acids prepared by chemical synthesis. Further, the above nucleic acids can be single-stranded, double-stranded, or triple-stranded, and there is no special limit on their molecular weights. Further, the nucleic acids of the present application may be nucleic acids modified by a chemical modification, enzyme modification, or peptide modification.

In addition, the cell is from a human or a mouse. Further, the cell is a mouse dendritic cell (DC 2.4), a mouse macrophage (RAW 264.7), an adenocarcinoma human alveolar basal epithelial cell (A549), a human pancreatic cancer cell (BxPC3), or a HeLa cell. More preferably, the cell is an A549 cell (A549-Luc).

The present application also provides a preparation method of the cationic lipid analog material above, and the specific method is as follows: adding an aldehyde compound and an amine compound to an organic solution; allowing to react for 10 min to 120 min before sequentially adding a carboxylic acid compound and an isocyanide compound; allowing to react at 4° C. to 60° C. for 6 h to 72 h; and separating and purifying a product by column chromatography after completion of reaction to obtain the cationic lipid analog material.

In the present application, the small-molecule cationic lipid analog material is synthesized through a Ugi reaction with the aldehyde compound, the amine compound, the carboxylic acid compound, and the isocyanide compound as raw materials. The reaction condition for the cationic lipid analog material of the present application is mild, and the synthesis process is simple and stable. The small-molecule cationic lipid analog material synthesized has low toxicity and can efficiently deliver various drugs into cells.

In addition, in the preparation method of the cationic lipid analog material, a mixture of methanol and dichloromethane is used as a mobile phase for the separation with the chromatography column.

In addition, in the preparation method of the cationic lipid analog material, a molar ratio of the aldehyde compound, the amine compound, the carboxylic acid compound, and the isocyanide compound is (0.1-1):(0.1-1):(0.1-1):(0.1-1), and preferably, the molar ratio is 1:1:1:0.5.

In addition, in the preparation method of the cationic lipid analog material, the aldehyde compound is any one selected from the group consisting of compounds A1 to A3:

A1
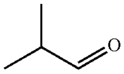

A2
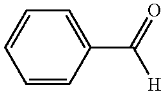

A3
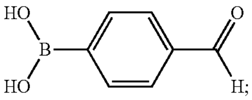

preferably, the aldehyde compound is compound A1;

the amine compound is any one selected from the group consisting of compounds R1 to R11:

R1
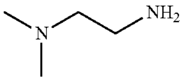

R2
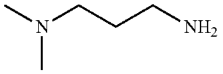

R3
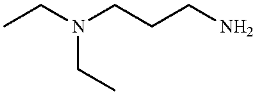

R4
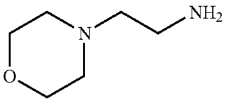

R5
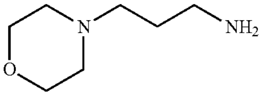

R6
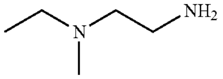

R7
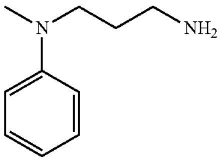

-continued

R8
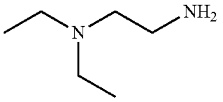

R9
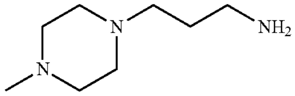

R10
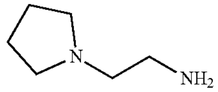

R11
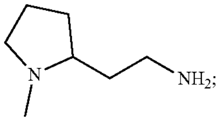

the carboxylic acid compound is any one selected from the group consisting of compounds CHS, C18-1, C18-2, or C8 to C20:

C8
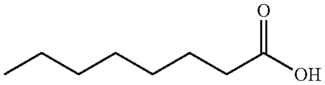

C9
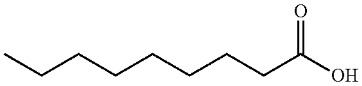

C10
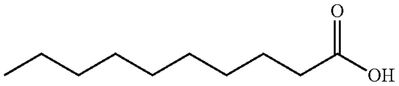

C11
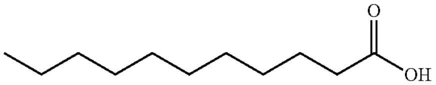

C12
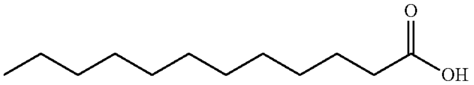

C13
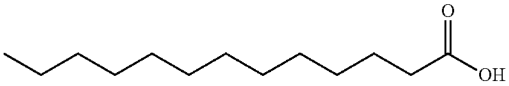

C14
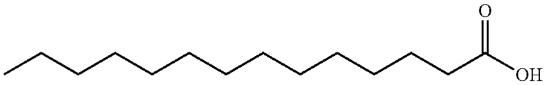

C15
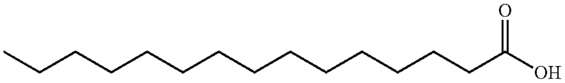

C16
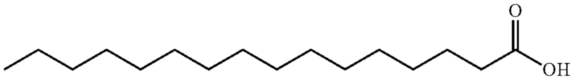

-continued

C17

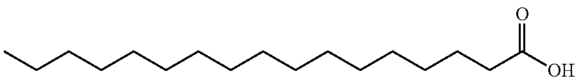

C18

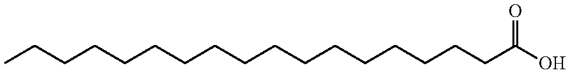

C19

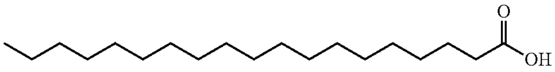

C20

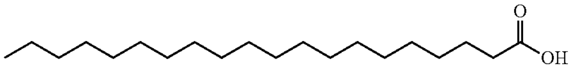

C18-1

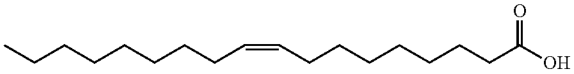

C18-2

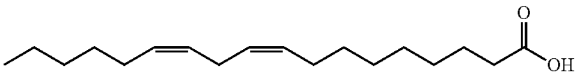

CHS

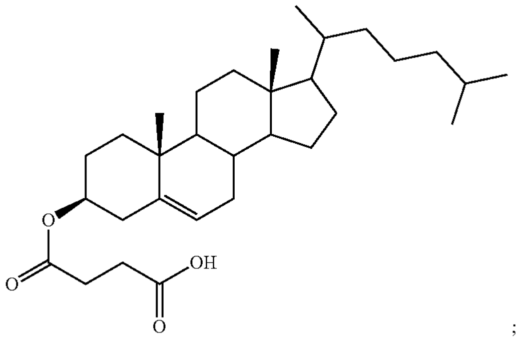

;

the isocyanide compound is any one selected from the group consisting of compounds I1, I2-1, I2, I2-3, I3:

I1

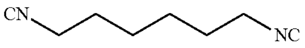

I2-1

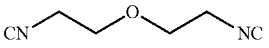

I2

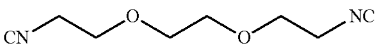

I2-3

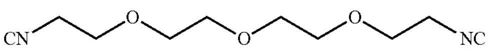

I3

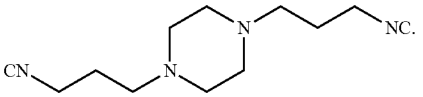

Compared with the prior art, the present application has the following beneficial effects:

The cationic lipid analog materials of the present application can efficiently bind to nucleic acids such as plasmid DNA, mRNA, and siRNA. Moreover, they can deliver different plasmid DNAs to various cells, and all have high transfection efficiency, even achieving or exceeding the level of current transfection reagents on the market. The cationic lipid analog material of the present application can be used as a safe and efficient intracellular delivery carrier of nucleic acid drugs or a transfection reagent, and has practical biomedical application value.

Figure 7:
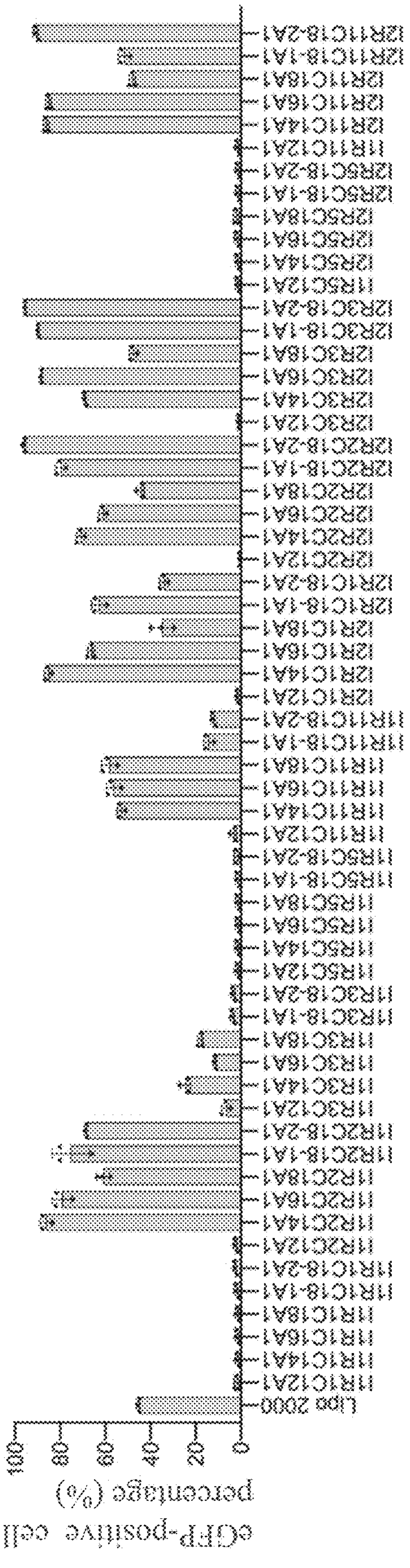
FIG. 7 shows positive rates of eGFP-mRNA transfected by different cationic lipid analog materials, where a dosage of 11R2C14A1, 11R2C18-1A1, 11R2C18-2A1, 11R11C14A1, I2R2C14A1, I2R2C18-1A1, I2R2C18-2A1, I2R3C16A1, I2R3C18A1, I2R3C18-1A1. I2R3C18-2A1, I2R11C14A1, I2R11C16A1, I2R11C18-1A1, and I2R11C18-2A1 is 1 μg/well; and a dosage of I1R1C12A1, 11R1C14A1, 11R1C16A1, 11R1C18A1, 11R1C18-1A1, I1R1C18-2A1, I1R2C12A1, I1R2C16A1, 11R2C18A1, 11R3C12A1, 11R3C14A1, 11R3C16A1, I1R3C18A1, 11R3C18-1A1, 11R3C18-2A1, 11R5C12A1, 11R5C14A1, I1R5C16A1, I1R5C18A1, 11R5C18-1A1, 11R5C18-2A1, I1R11C12A1, 11R11C16A1, 11R11C18A1, I1R11C18-1A1, I1R11C18-2A1, I2R1C12A1, I2R1C14A1, I2R1C16A1, I2R1C18A1, I2R1C18-1A1, I2R1C18-2A1, I2R2C12A1, I2R2C16A1, I2R2C18A1, I2R3C12A1.
Figure 8:
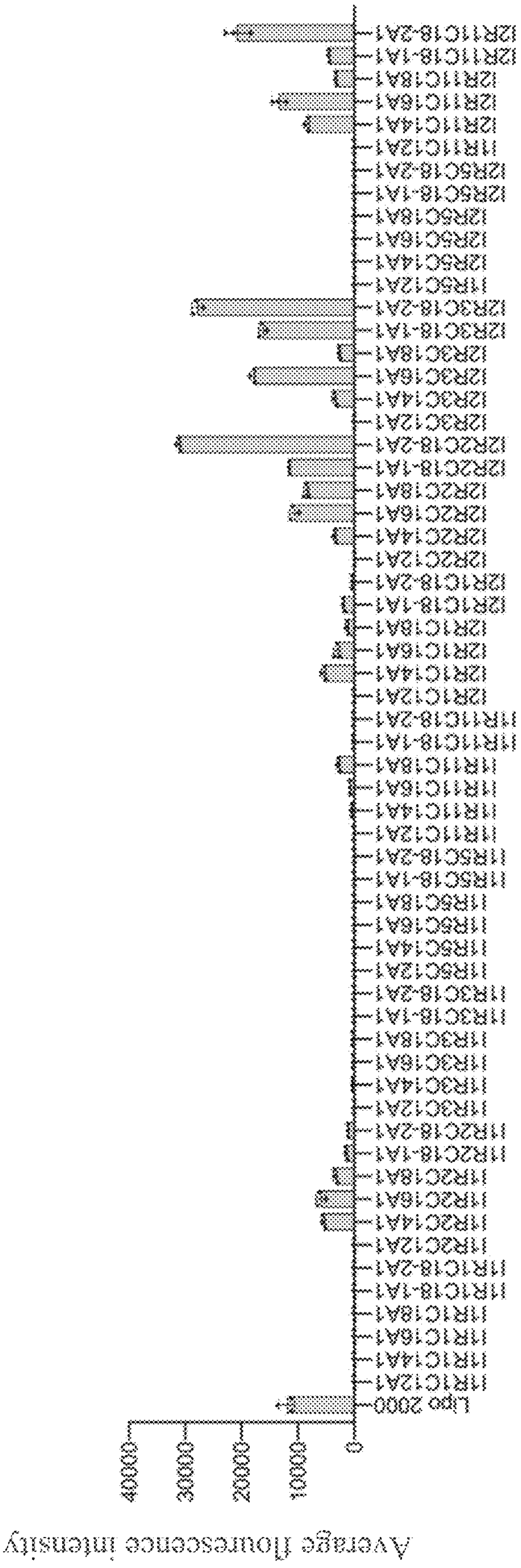

I2R3C14A1, I2R5C12A1, I2R5C14A1, I2R5C16A1. I2R5C18A1, I2R5C18-1A1. I2R5C18-2A1, I2R11C12A1, and I2R11C18A1 is 2 μg/well;

FIG. 8 shows average fluorescence intensities of eGFP-mRNA transfected by different cationic lipid analog materials, where experimental conditions are consistent with those in FIG. 7.

Figure 9:
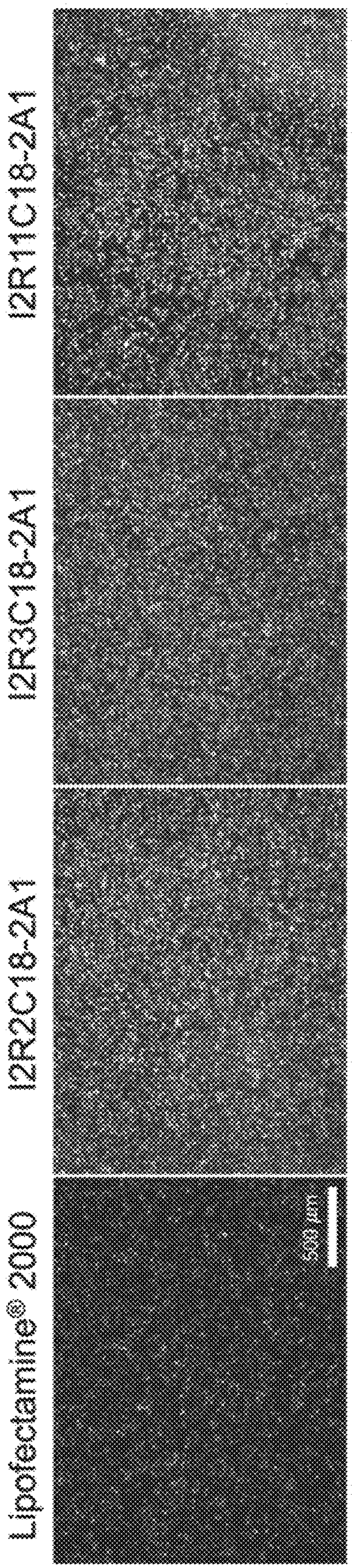
Figure 10:
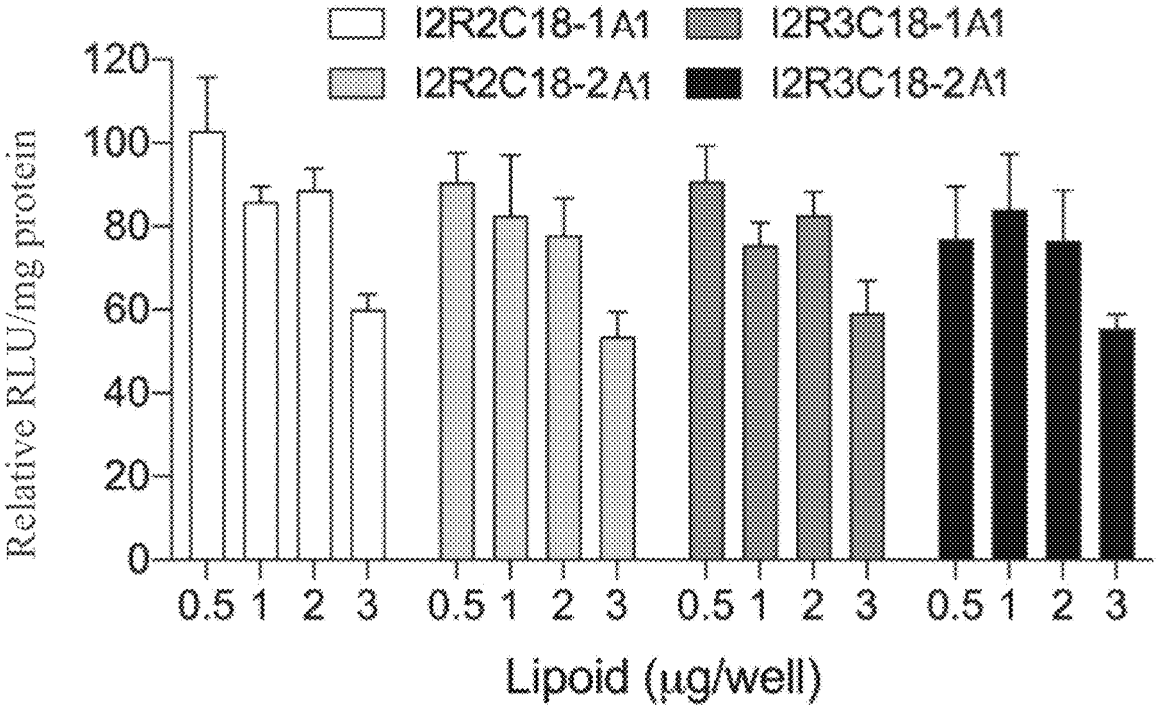
Figure 11:
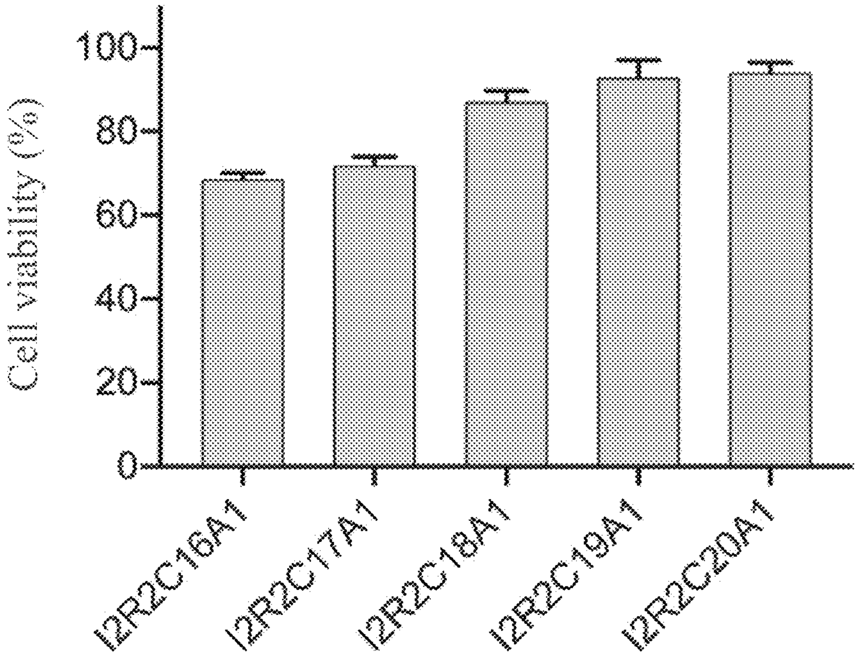

FIG. 9 shows LSCM results of DC 2.4 cells transfected with eGFP-mRNA by I2R2C18-2A1. I2R3C18-2A1, I2R11C18-2A1, and a commercial transfection reagent Lipofectamine 2000 as a positive control;

FIG. 10 shows gene silencing results of siRNA transfected by I2R2C18-1A1, I2R3C18-1A1, I2R2C18-2A1, and I2R3C18-2A1 at different doses;

FIG. 11 shows cytotoxicity results of I2R2C16A1, I2R2C17A1, I2R2C18A1, I2R2C19A1, and I2R2C20A1.

DETAILED DESCRIPTION

In order to well illustrate the objectives, technical solutions, and advantages of the present application, the present application will be further described below in conjunction with specific examples. It should be understood by those skilled in the art that the specific examples described herein are merely intended to explain the present application, rather than to limit the present application.

In the examples, unless otherwise specified, the experimental methods used are conventional, and the materials and reagents used are commercially available.

Example 1 Synthesis and Characterization of Cationic Lipid Analog Materials

A synthesis route of the cationic lipid analog material of the present application was as follows:

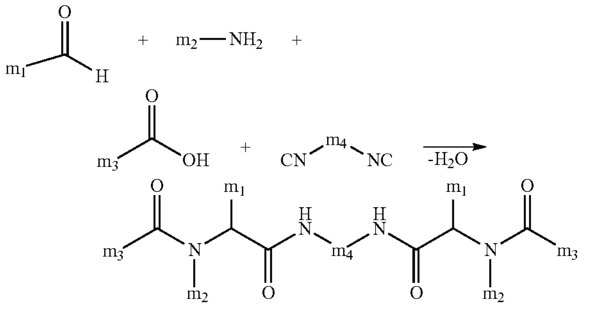

where the amine compound $m_2$—$NH_2$ was any one selected from the group consisting of compounds R1 to R11 as follows; the carboxylic acid compound

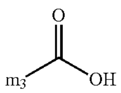

was any one selected from the group consisting of compounds C8 to C20, CHS as follows; the aldehyde compound

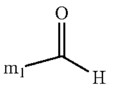

was any one selected from the group consisting of compounds A1 to A3 as follows; and the isocyanide compound

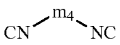

was any one selected from the group consisting of compounds I1 to I3 as follows:

R1

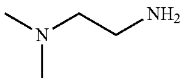

R2

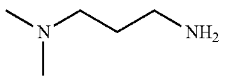

R3

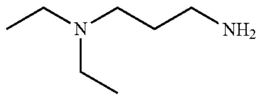

R4

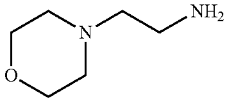

R5

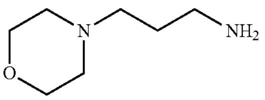

R6

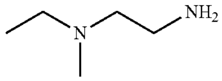

R7

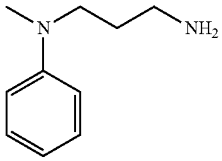

R8

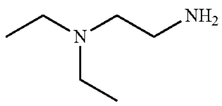

R9

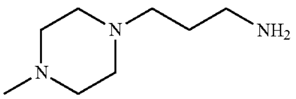

R10

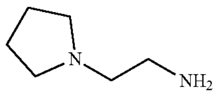

-continued

R11

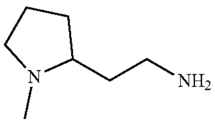

C8

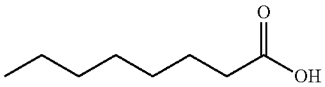

C9

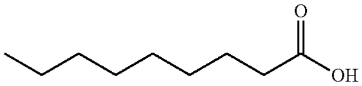

C10

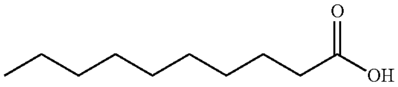

C11

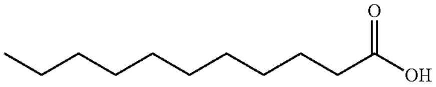

C12

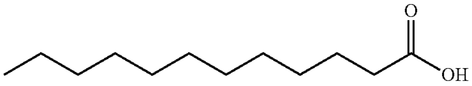

C13

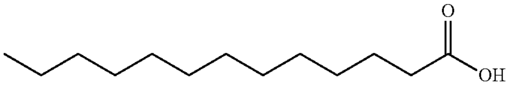

C14

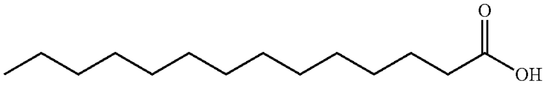

C15

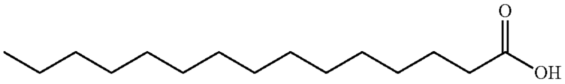

C16

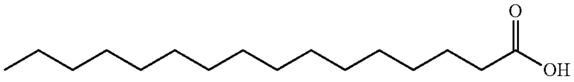

C17

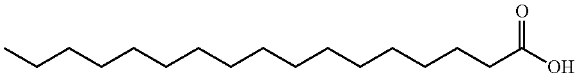

C18

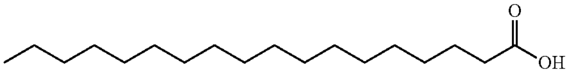

C19

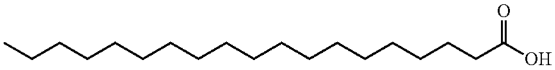

C20

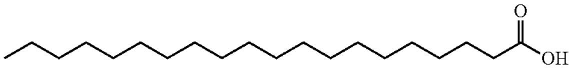

C18-1

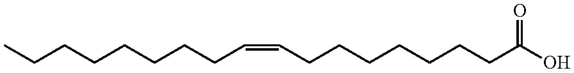

-continued

C18-2

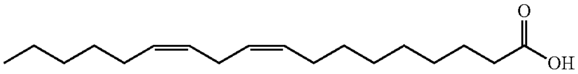

CHS

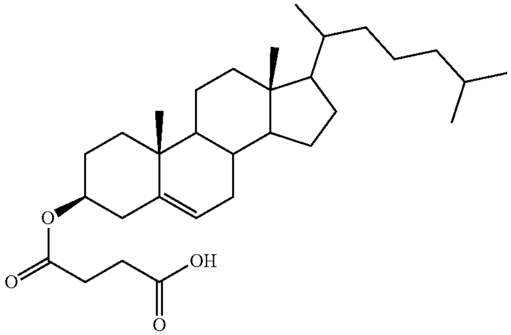

A1

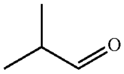

A2

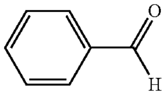

A3

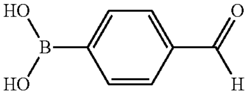

I1

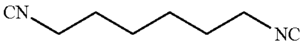

I2-1

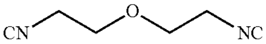

I2

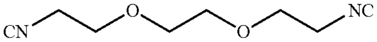

I2-3

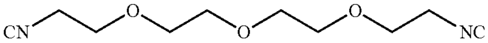

I3

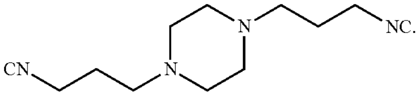

A preparation method of the cationic lipid analog material in this example was specifically as follows: 1 mmol of isobutyl aldehyde and 1 mmol of an amine compound were added to 0.5 mL of a methanol solution, and a reaction was conducted for 60 min; 1 mmol of a carboxylic acid compound and 0.5 mmol of an isocyanide compound were added sequentially, and a reaction was conducted at 40° C. for 12 h; and after the reaction was completed, a product was separated and purified by a chromatography column, where a mixture of methanol and dichloromethane was adopted as a mobile phase.

Raw materials used in this example and structures of cationic lipid analog materials synthesized thereby were shown in Table 1.

TABLE 1
| | Iso-cyanide compound | Amine compound | Carboxylic acid compound | Aldehyde compound | Cationic lipid analog material (number and structure formula) |
|---|---|---|---|---|---|
| 1 | I1 | R1 | C12 | A1 | 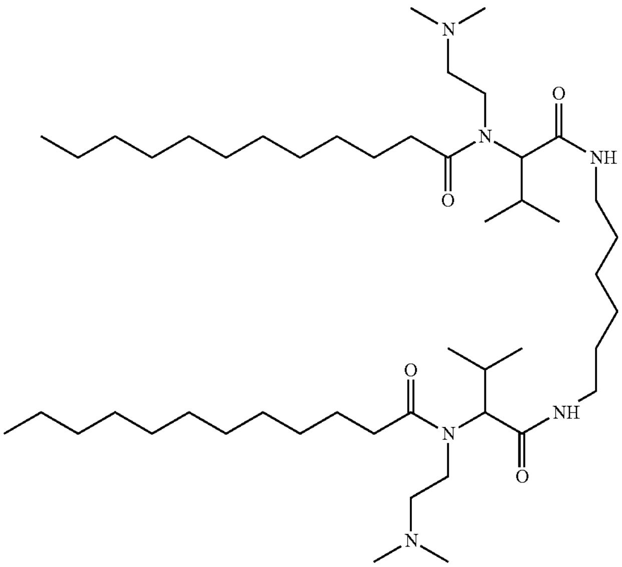 I1R1C12A1 |
| 2 | I1 | R1 | C14 | A1 | 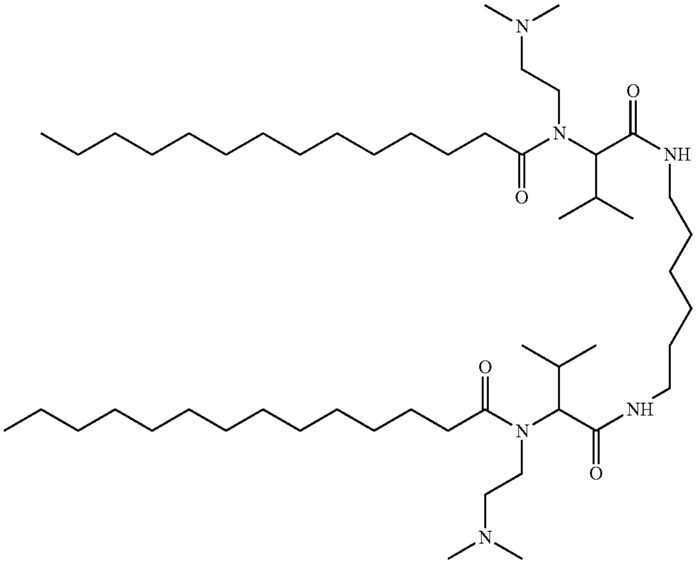 I1R1C14A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 3 | I1 | R1 | C16 | A1 | 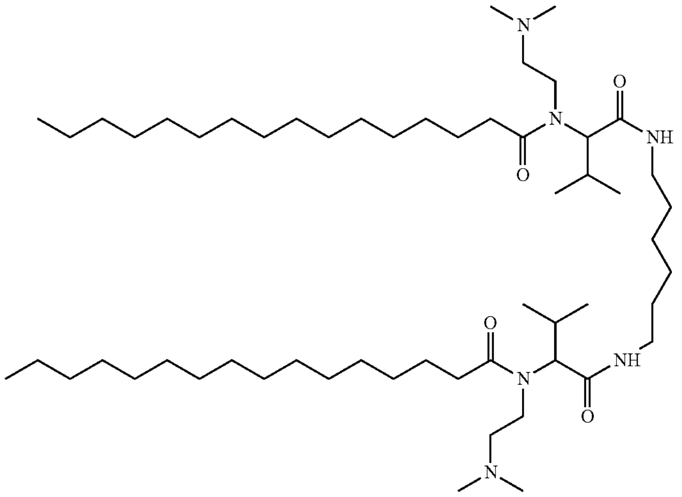 I1R1C16A1 |
| 4 | I1 | R1 | C18 | A1 | 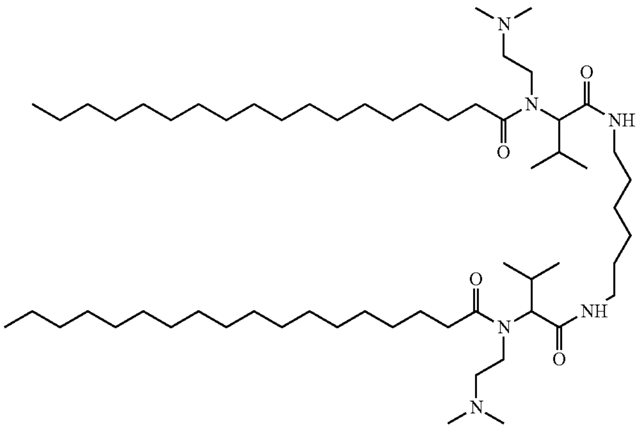 I1R1C18A1 |
| 5 | I1 | R1 | C20 | A1 | 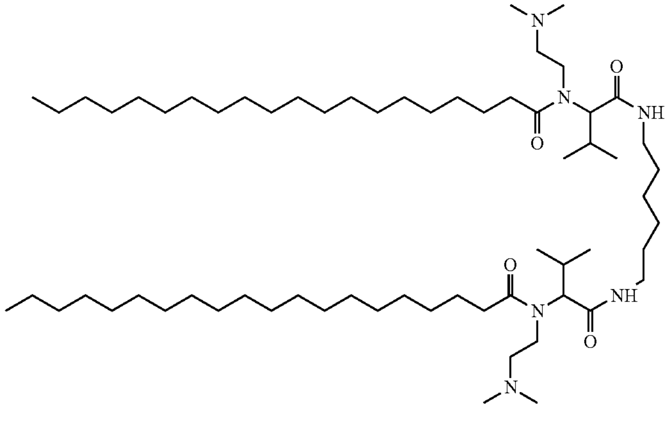 I1R1C120A1 |

TABLE 1-continued
| | Isocyanide compound | Amine compound | Carboxylic acid compound | Aldehyde compound | Cationic lipid analog material (number and structure formula) |
|---|---|---|---|---|---|
| 6 | I1 | R1 | C18-1 | A1 | 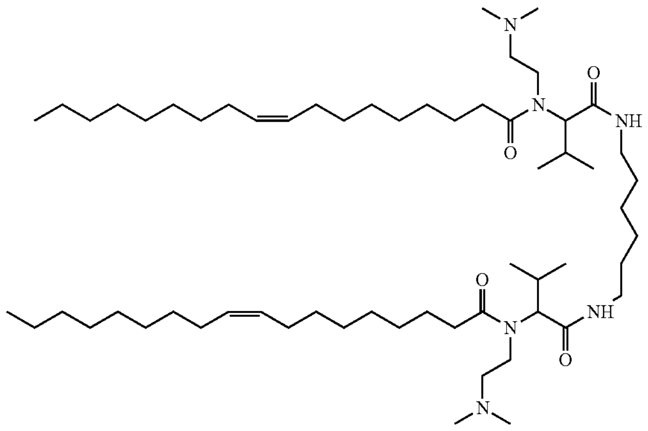 [SMILES: CCCCCCCC/C=C\CCCCCCCC(=O)N(CCN(C)C)C(C(=O)NCCCCCCNC(=O)C(C(C)C)N(CCN(C)C)C(=O)CCCCCCC/C=C\CCCCCCCC)C(C)C] I1R1C18-1A1 |
| 7 | I1 | R1 | C18-2 | A1 | 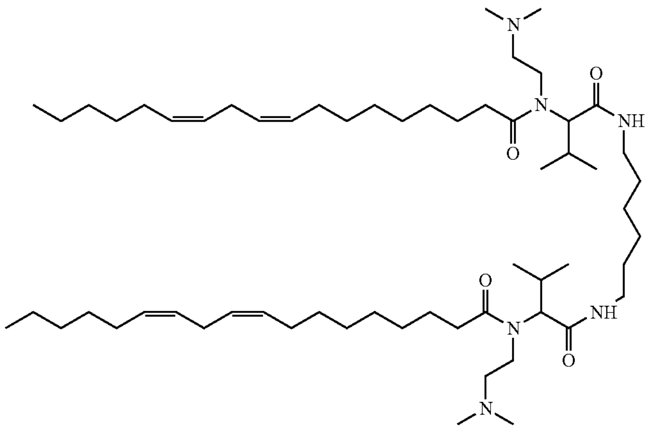 [SMILES: CCCCC/C=C\C/C=C\CCCCCCCC(=O)N(CCN(C)C)C(C(=O)NCCCCCCNC(=O)C(C(C)C)N(CCN(C)C)C(=O)CCCCCCC/C=C\C/C=C\CCCCC)C(C)C] I1R1C18-2A1 |

TABLE 1-continued
| | Isocyanide compound | Amine compound | Carboxylic acid compound | Aldehyde compound | Cationic lipid analog material (number and structure formula) |
|---|---|---|---|---|---|
| 8 | I1 | R2 | C12 | A1 | 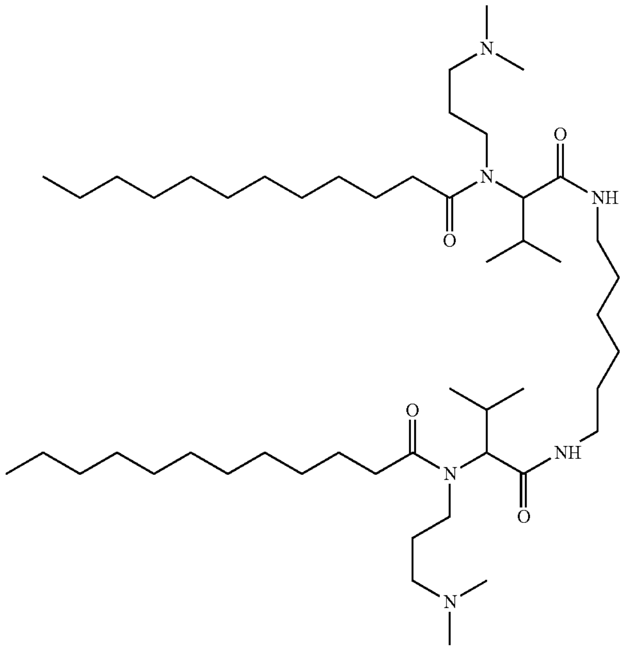 I1R2C12A1 |
| 9 | I1 | R2 | C14 | A1 | 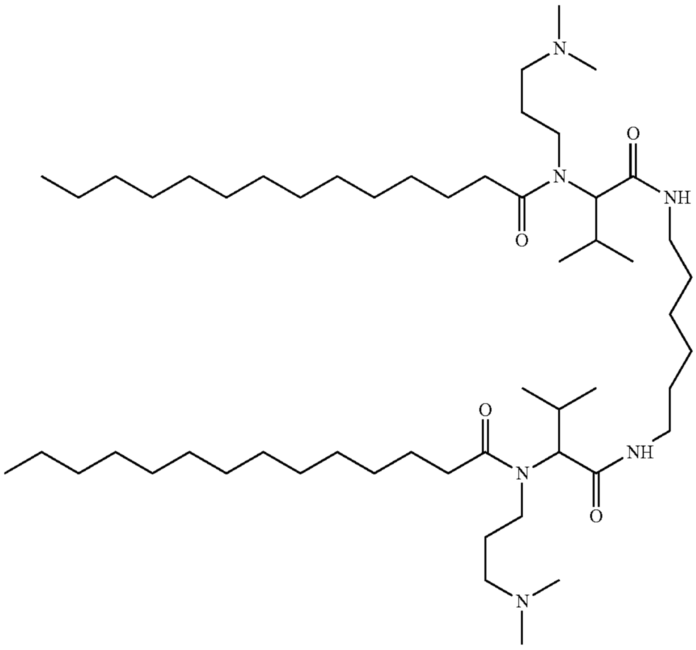 I1R2C14A1 |

TABLE 1-continued
| | Isocyanide compound | Amine compound | Carboxylic acid compound | Aldehyde compound | Cationic lipid analog material (number and structure formula) |
|---|---|---|---|---|---|
| 10 | I1 | R2 | C16 | A1 | 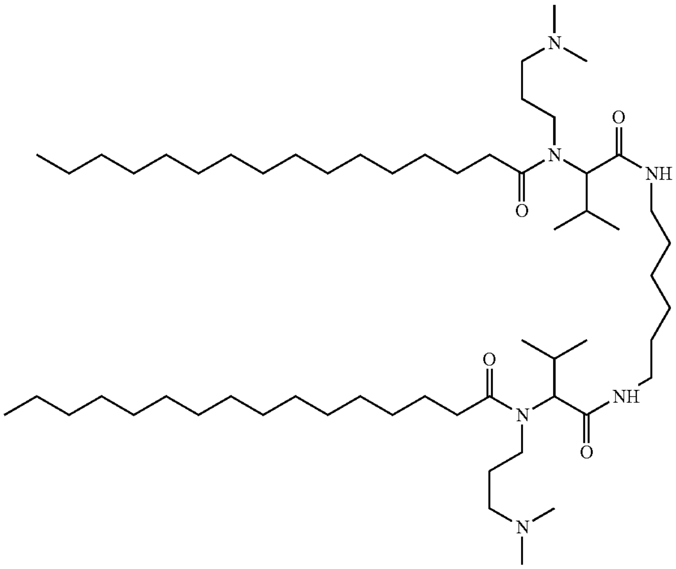 I1R2C16A1 |
| 11 | I1 | R2 | C18 | A1 | 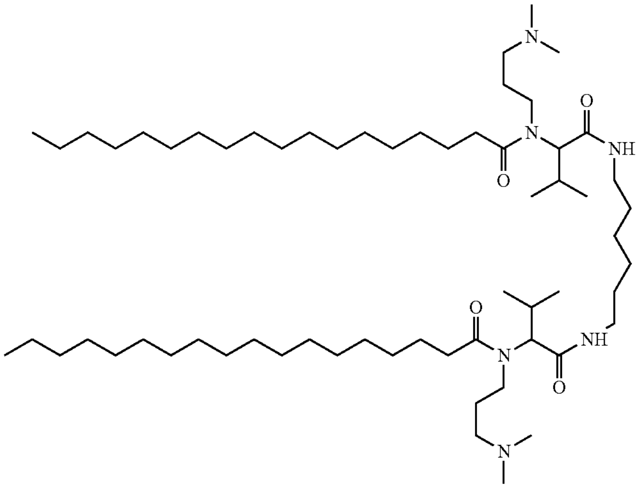 I1R2C18A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 12 | I1 | R2 | C20 | A1 | 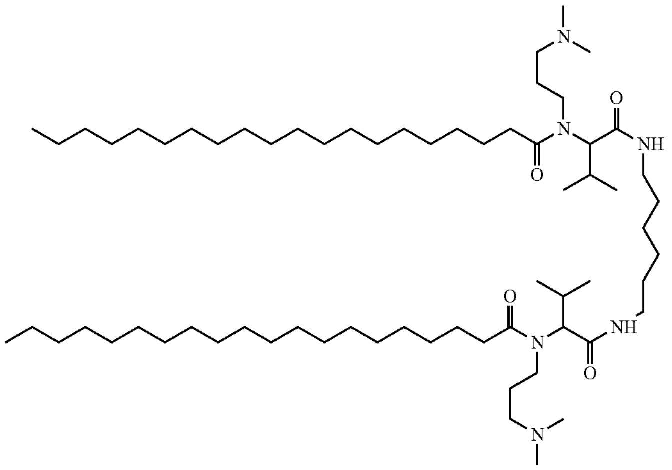 I1R2C20A1 |
| 13 | I1 | R2 | C18-1 | A1 | 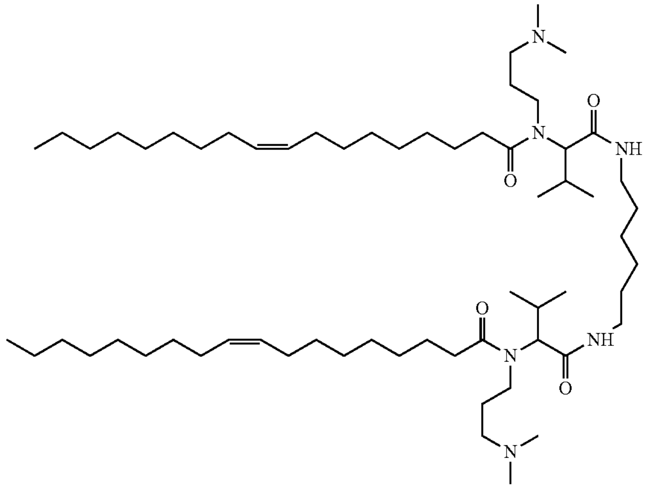 I1R2C18-1A1 |
| 14 | I1 | R2 | C18-2 | A1 | 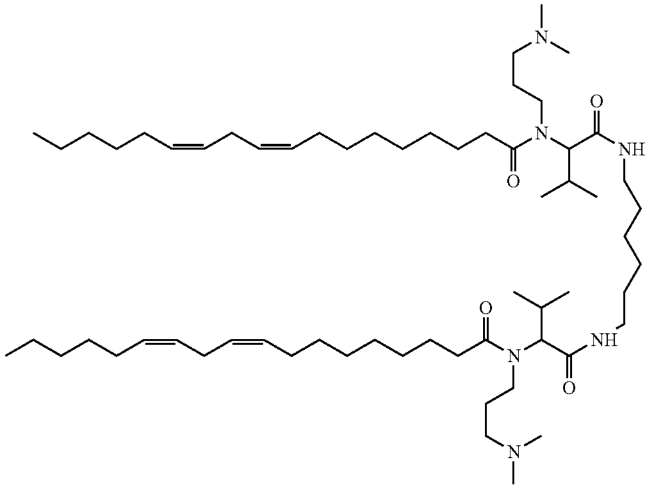 |

TABLE 1-continued
| | Iso-cyanide compound | Amine compound | Carboxylic acid compound | Aldehyde compound | Cationic lipid analog material (number and structure formula) |
|---|---|---|---|---|---|
| | | | | | I1R2C18-2A1 |
| 15 | I1 | R3 | C12 | A1 | 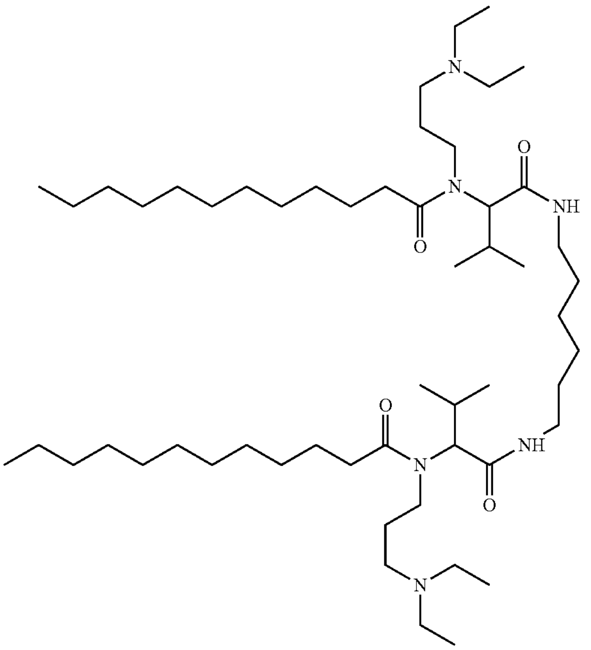 [SMILES: CCCCCCCCCCCC(=O)N(CCCN(CC)CC)C(C(=O)NCCCCCCNC(=O)C(C(C)C)N(CCCN(CC)CC)C(=O)CCCCCCCCCCC)C(C)C] I1R3C12A1 |
| 16 | I1 | R3 | C14 | A1 | 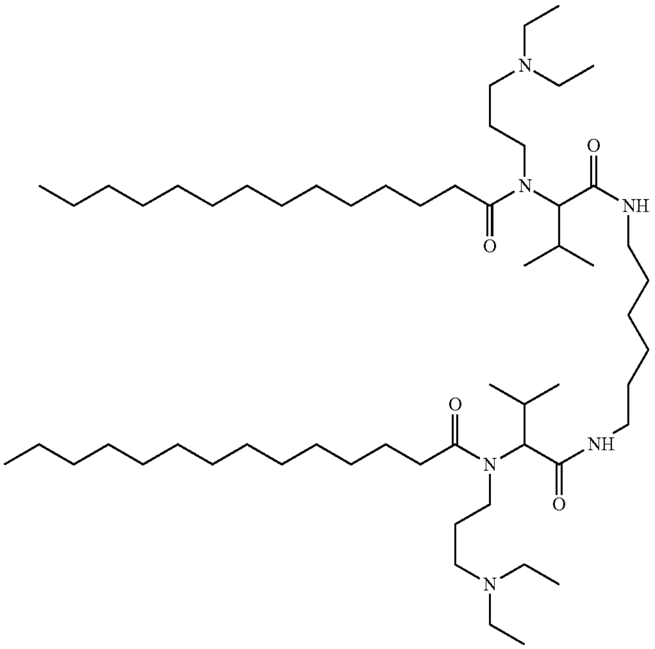 [SMILES: CCCCCCCCCCCCCC(=O)N(CCCN(CC)CC)C(C(=O)NCCCCCCNC(=O)C(C(C)C)N(CCCN(CC)CC)C(=O)CCCCCCCCCCCCC)C(C)C] I1R3C14A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 17 | I1 | R3 | C16 | A1 | 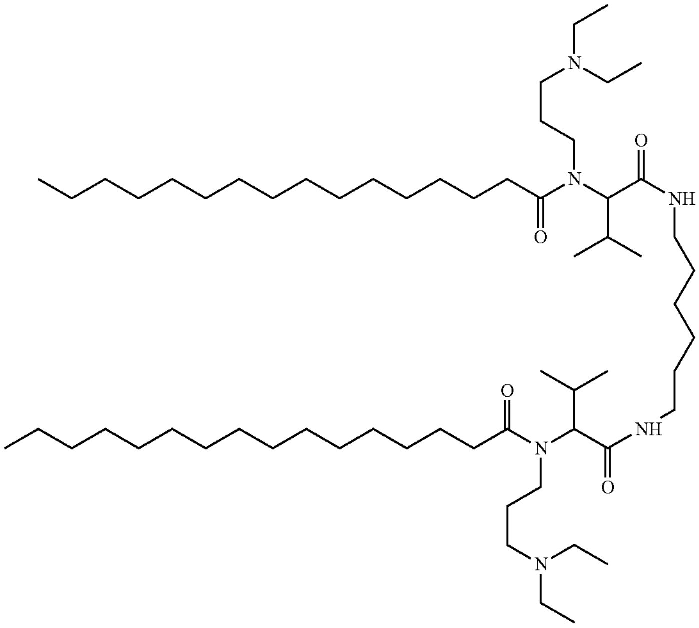 I1R3C16A1 |
| 18 | I1 | R3 | C18 | A1 | 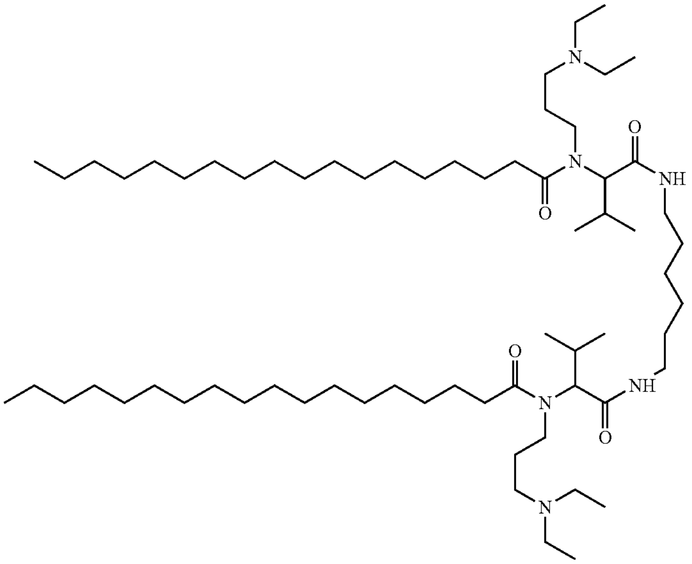 I1R3C18A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 19 | I1 | R3 | C20 | A1 | 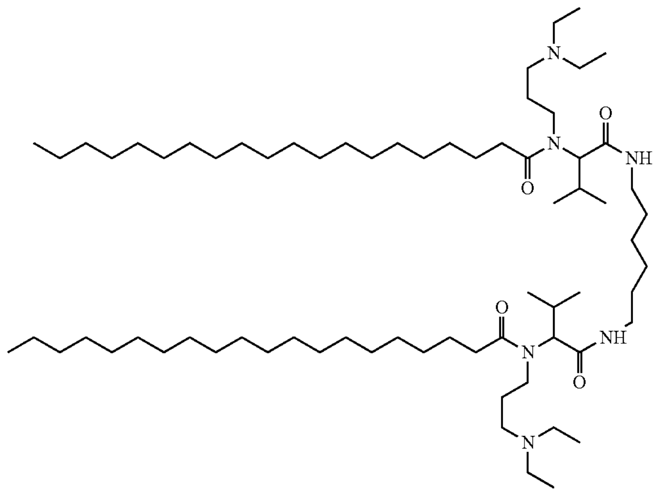 I1R3C20A1 |
| 20 | I1 | R3 | C18-1 | A1 | 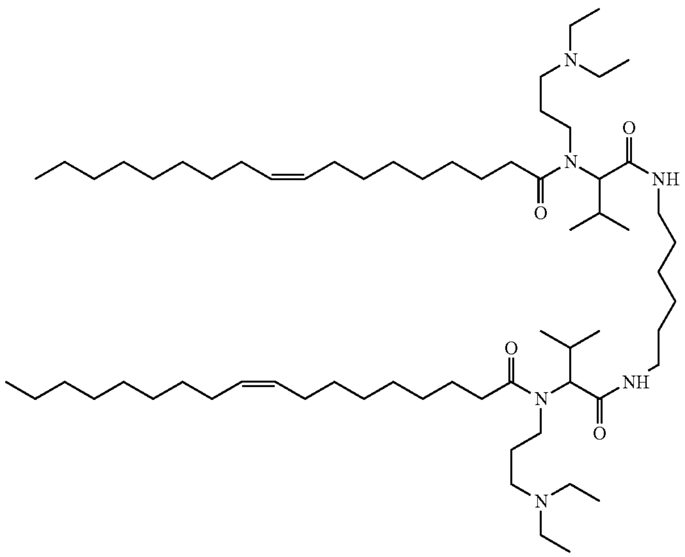 I1R3C18-1A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 21 | I1 | R3 | C18-2 | A1 | 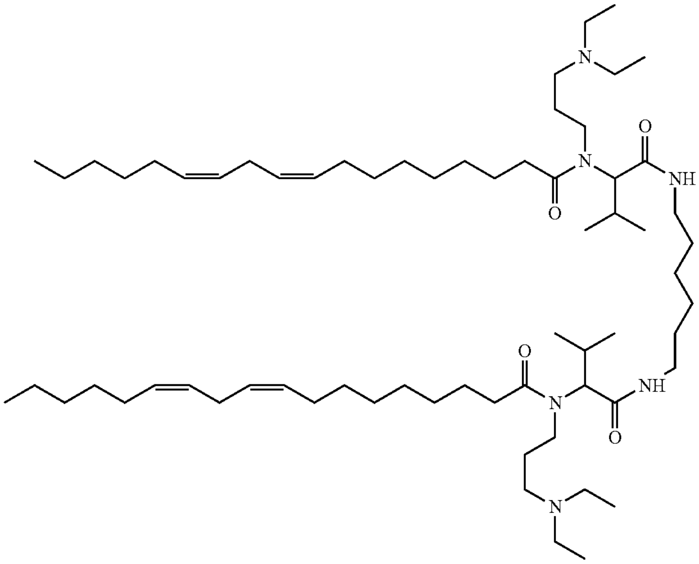 [SMILES: CCCCC/C=C\C/C=C\CCCCCCCC(=O)N(CCCN(CC)CC)C(C(=O)NCCCCCCNC(=O)C(C(C)C)N(CCCN(CC)CC)C(=O)CCCCCCC/C=C\C/C=C\CCCCC)C(C)C] I1R3C18-2A1 |
| 22 | I1 | R5 | C12 | A1 | 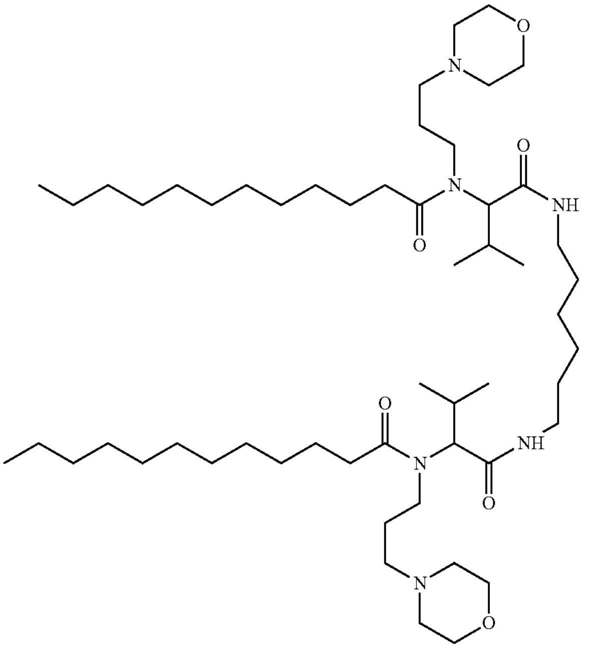 [SMILES: CCCCCCCCCCCC(=O)N(CCCN1CCOCC1)C(C(=O)NCCCCCCNC(=O)C(C(C)C)N(CCCN1CCOCC1)C(=O)CCCCCCCCCCC)C(C)C] I1R5C12A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 23 | I1 | R5 | C14 | A1 | 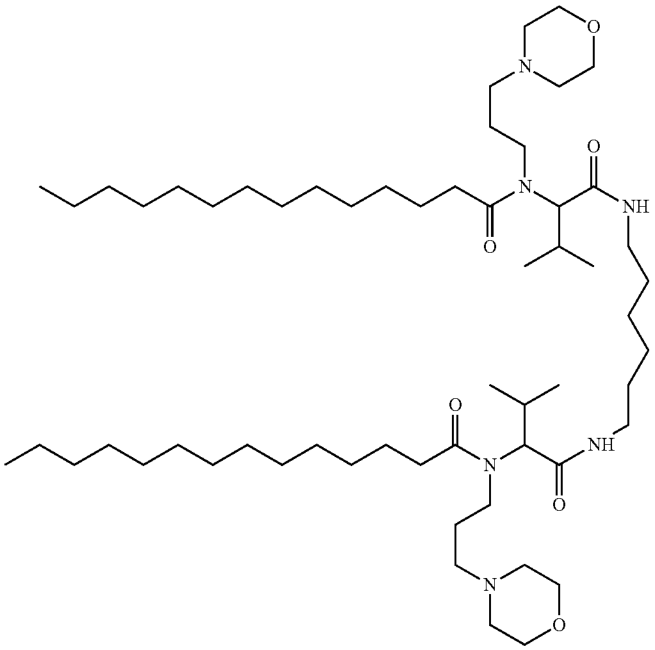 I1R5C14A1 |
| 24 | I1 | R5 | C16 | A1 | 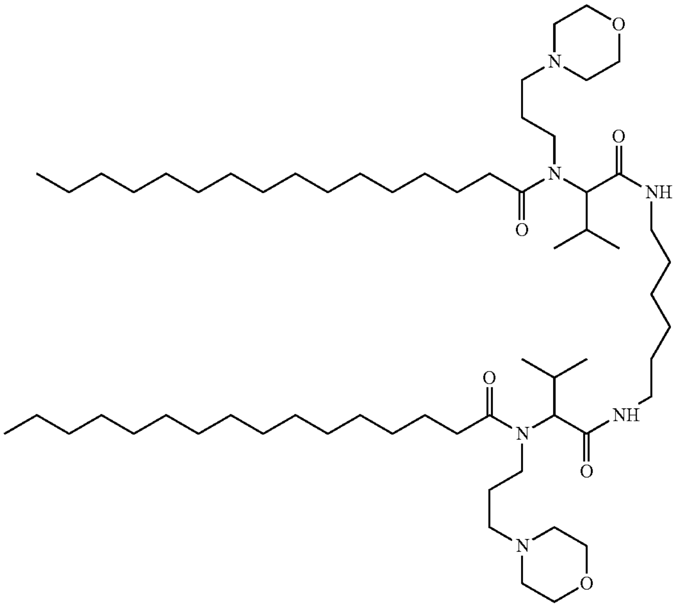 I1R5C16A1 |

TABLE 1-continued
| | Isocyanide compound | Amine compound | Carboxylic acid compound | Aldehyde compound | Cationic lipid analog material (number and structure formula) |
|---|---|---|---|---|---|
| 25 | I1 | R5 | C18 | A1 | 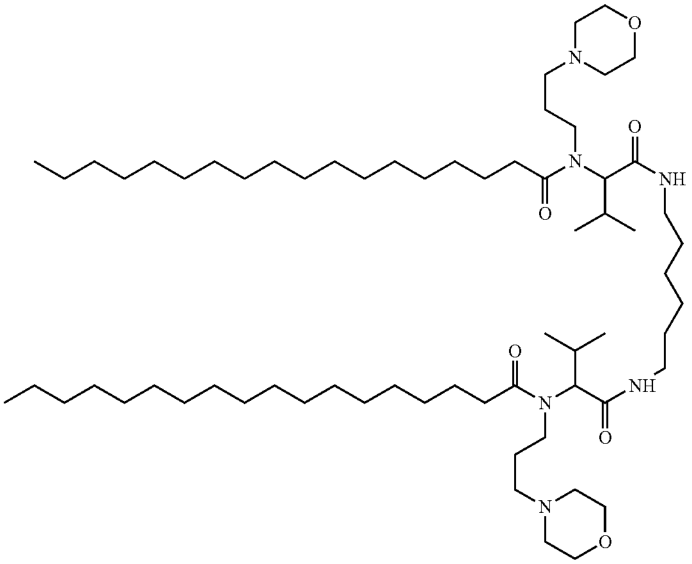 I1R5C18A1 |
| 26 | I1 | R5 | C20 | A1 | 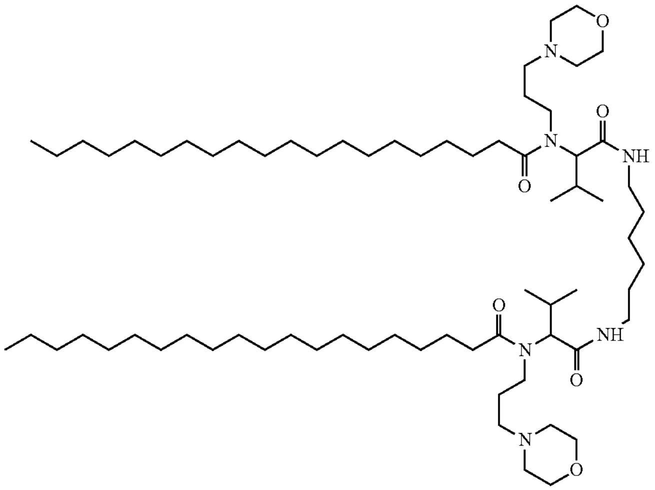 I1R5C20A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 27 | I1 | R5 | C18-1 | A1 | 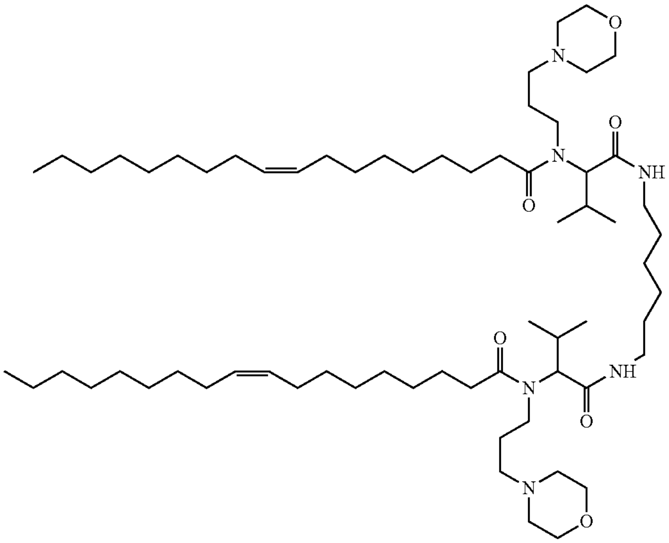 [SMILES: CCCCCCCC/C=C\CCCCCCCC(=O)N(CCCN1CCOCC1)C(C(=O)NCCCCCCNC(=O)C(C(C)C)N(CCCN1CCOCC1)C(=O)CCCCCCC/C=C\CCCCCCCC)C(C)C] I1R5C18-1A1 |
| 28 | I1 | R5 | C18-2 | A1 | 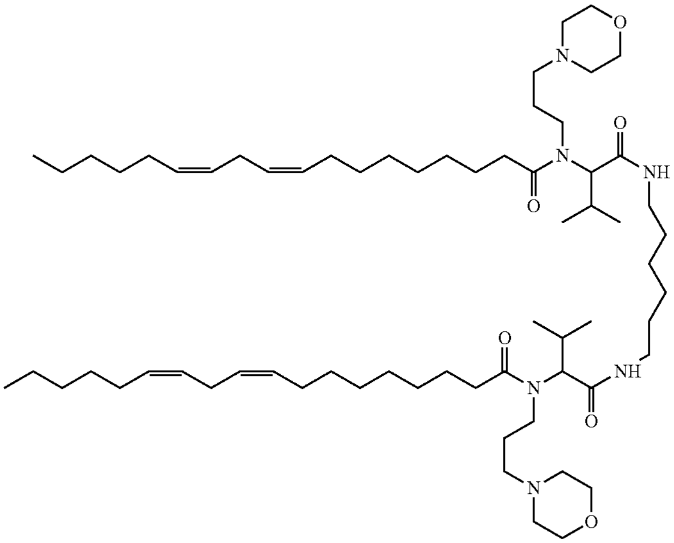 [SMILES: CCCCC/C=C\C/C=C\CCCCCCCC(=O)N(CCCN1CCOCC1)C(C(=O)NCCCCCCNC(=O)C(C(C)C)N(CCCN1CCOCC1)C(=O)CCCCCCC/C=C\C/C=C\CCCCC)C(C)C] I1R5C18-2A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 29 | I1 | R11 | C12 | A1 | 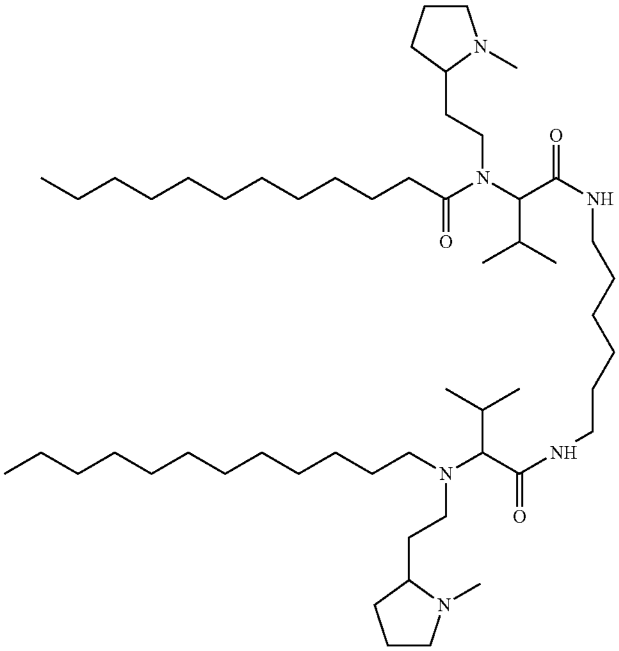 I1R11C12A1 |
| 30 | I1 | R11 | C14 | A1 | 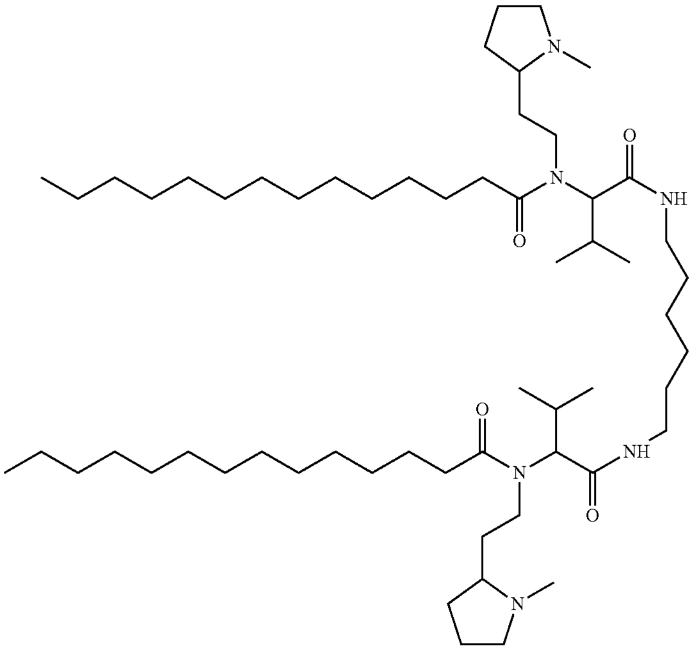 I1R11C14A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 31 | I1 | R11 | C16 | A1 | 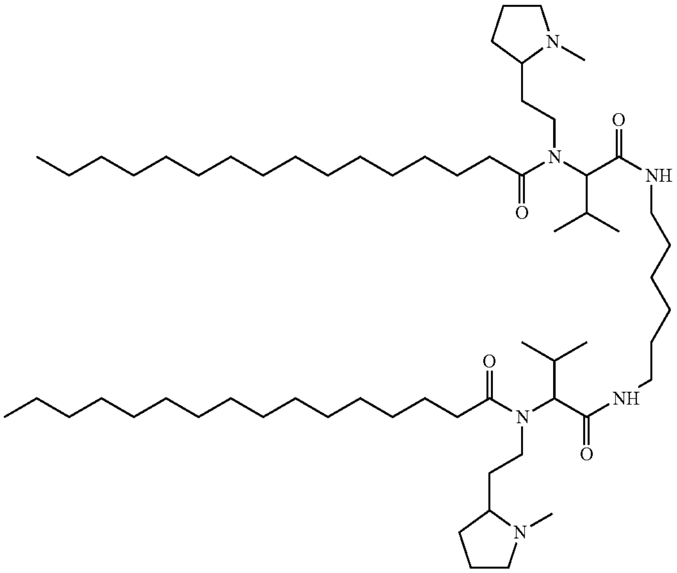 I1R11C16A1 |
| 32 | I1 | R11 | C18 | A1 | 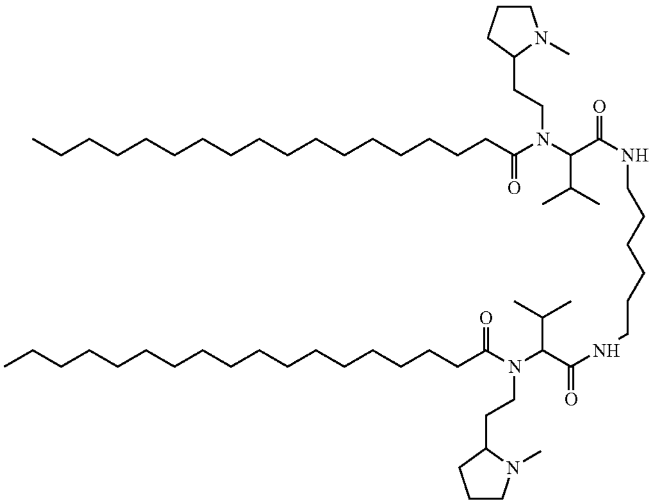 I1R11C18A1 |

TABLE 1-continued
| | Iso-cyanide com-pound | Amine com-pound | Car-boxylic acid com-pound | Aldehyde compound | Cationic lipid analog material (number and structure formula) |
|---|---|---|---|---|---|
| 33 | I1 | R11 | C20 | A1 | 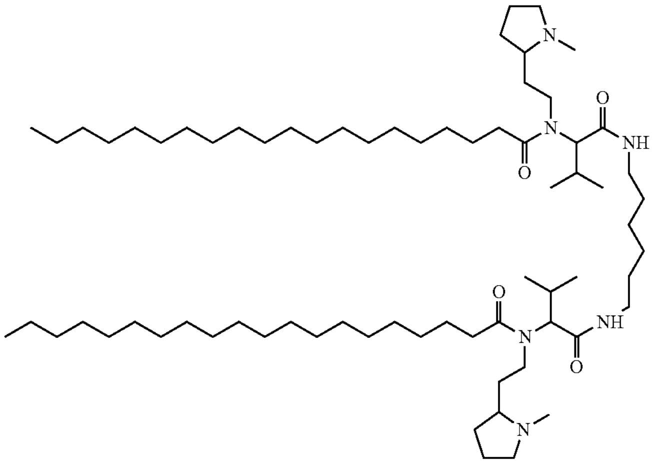 I1R11C20A1 |
| 34 | I1 | R11 | C18-1 | A1 | 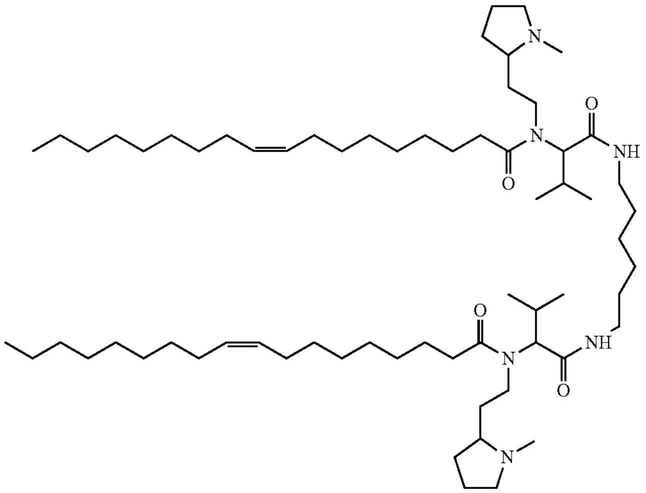 I1R11C18-1A1 |
| 35 | I1 | R11 | C18-2 | A1 | 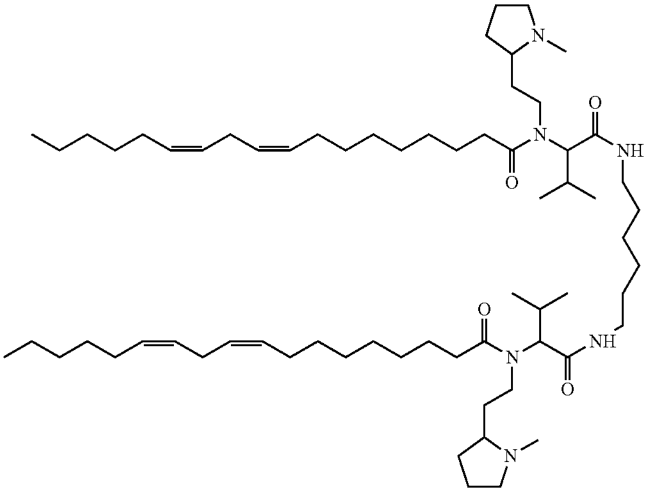 |

TABLE 1-continued
| | Iso-cyanide com-pound | Amine com-pound | Car-boxylic acid com-pound | Aldehyde compound | Cationic lipid analog material (number and structure formula) |
|---|---|---|---|---|---|
| | | | | | I1R11C18-2A1 |
| 36 | I2 | R1 | C12 | A1 | 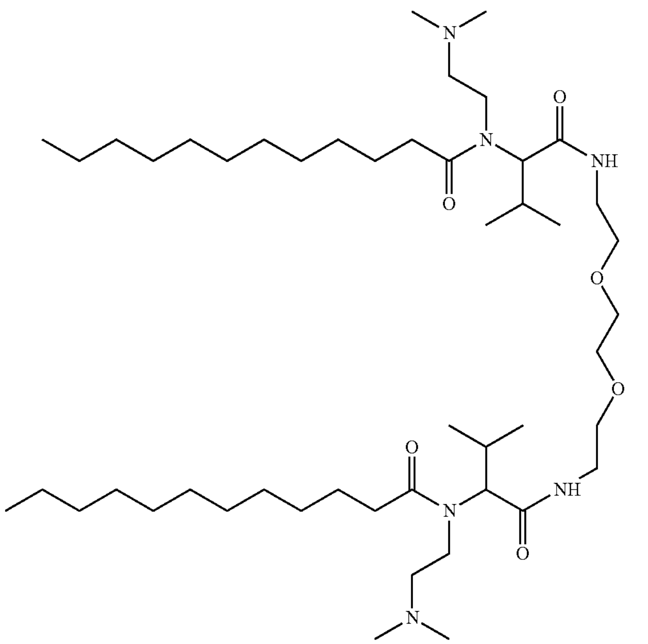 [SMILES: CCCCCCCCCCCC(=O)N(CCN(C)C)C(C(=O)NCCOCCOCCNC(=O)C(C(C)C)N(CCN(C)C)C(=O)CCCCCCCCCCC)C(C)C]<br>I2R1C12A1 |
| 37 | I2 | R1 | C14 | A1 | 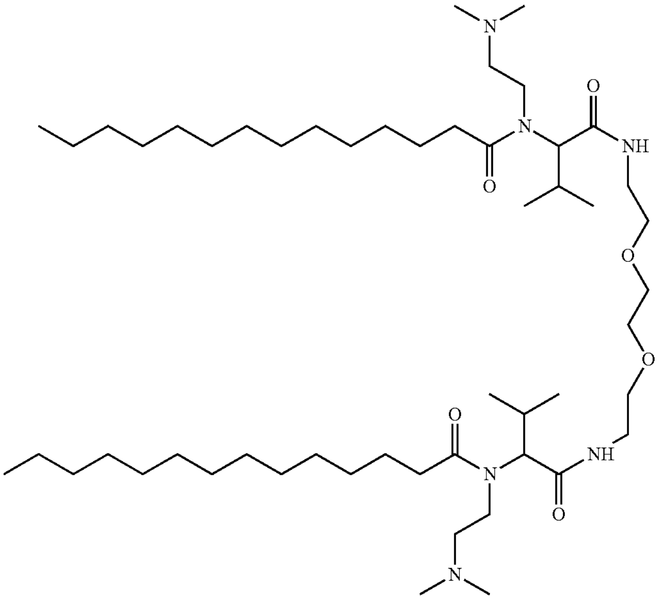 [SMILES: CCCCCCCCCCCCCC(=O)N(CCN(C)C)C(C(=O)NCCOCCOCCNC(=O)C(C(C)C)N(CCN(C)C)C(=O)CCCCCCCCCCCCC)C(C)C]<br>I2R1C14A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 38 | I2 | R1 | C16 | A1 | 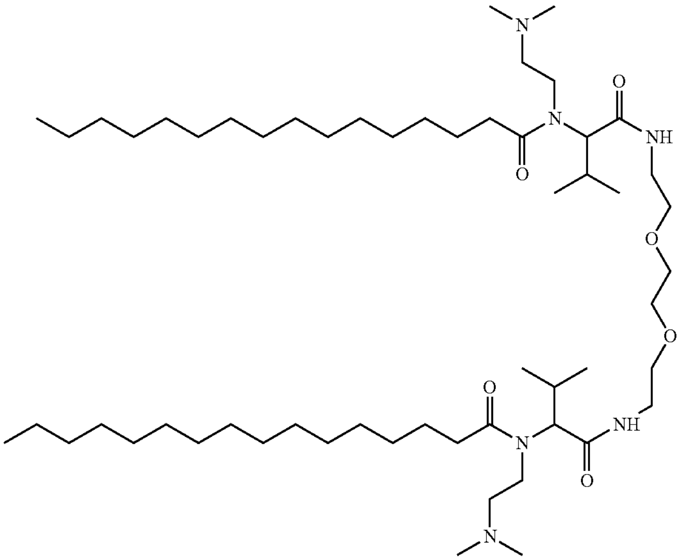 I2R1C16A1 |
| 39 | I2 | R1 | C18 | A1 | 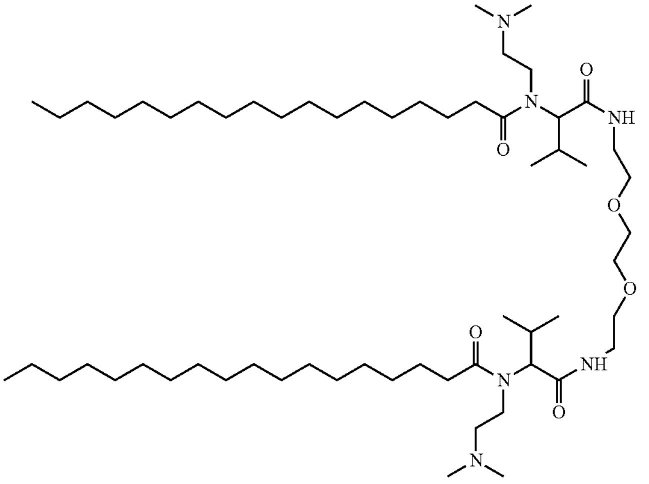 I2R1C18A1 |

TABLE 1-continued
| | Iso-cyanide com-pound | Amine com-pound | Car-boxylic acid com-pound | Aldehyde compound | Cationic lipid analog material (number and structure formula) |
|---|---|---|---|---|---|
| 40 | I2 | R1 | C20 | A1 | 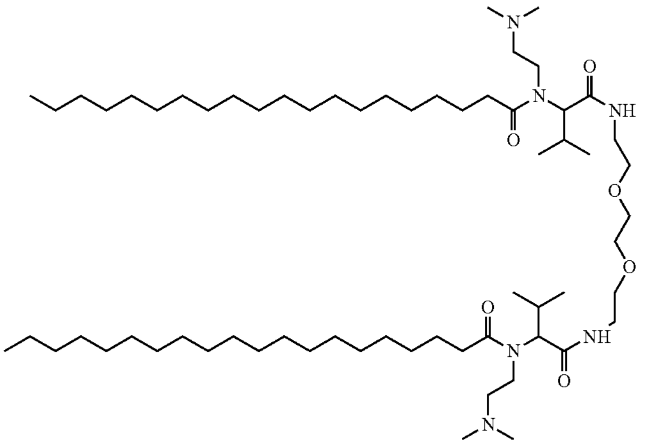 I2R1C20A1 |
| 41 | I2 | R1 | C18-1 | A1 | 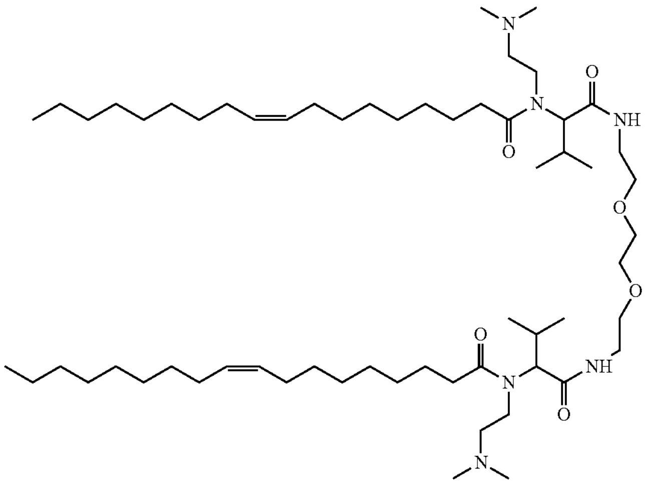 I2R1C18-1A1 |
| 42 | I2 | R1 | C18-2 | A1 | 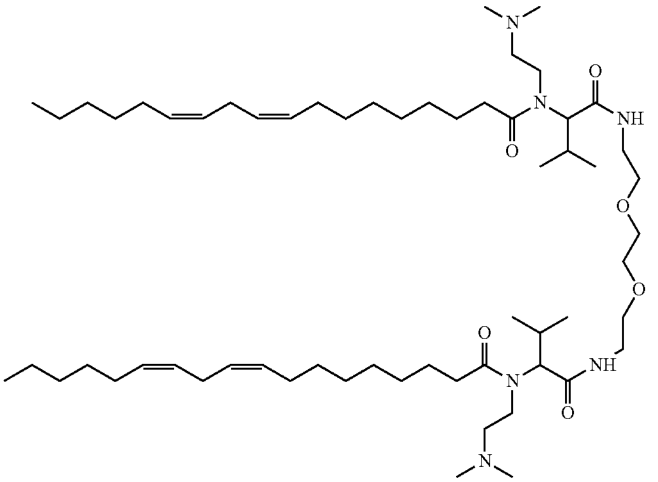 I2R1C18-2A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 43 | I2 | R2 | C12 | A1 | 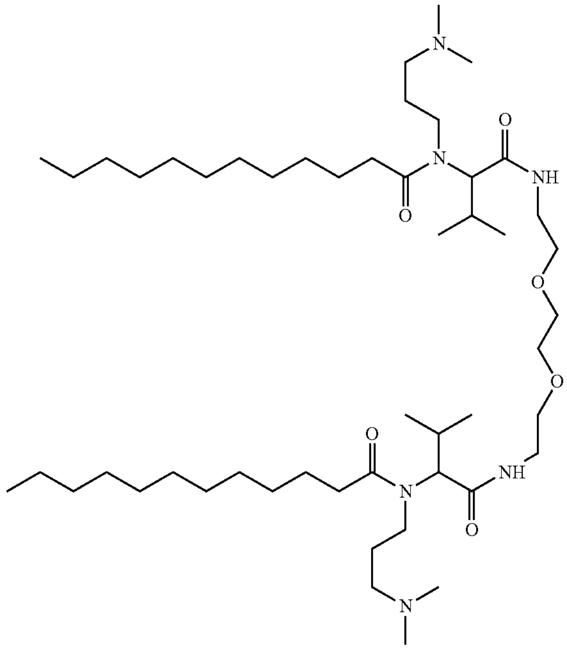 I2R2C12A1 |
| 44 | I2 | R2 | C14 | A1 | 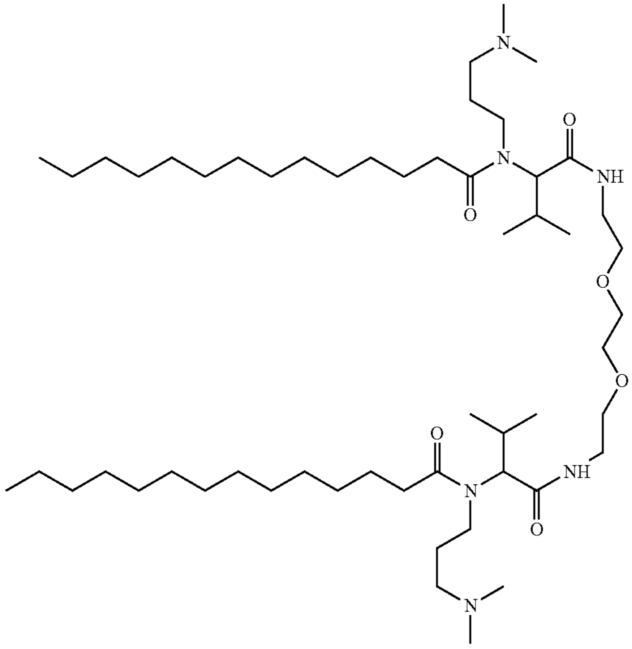 I2R2C14A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 45 | I2 | R2 | C16 | A1 | 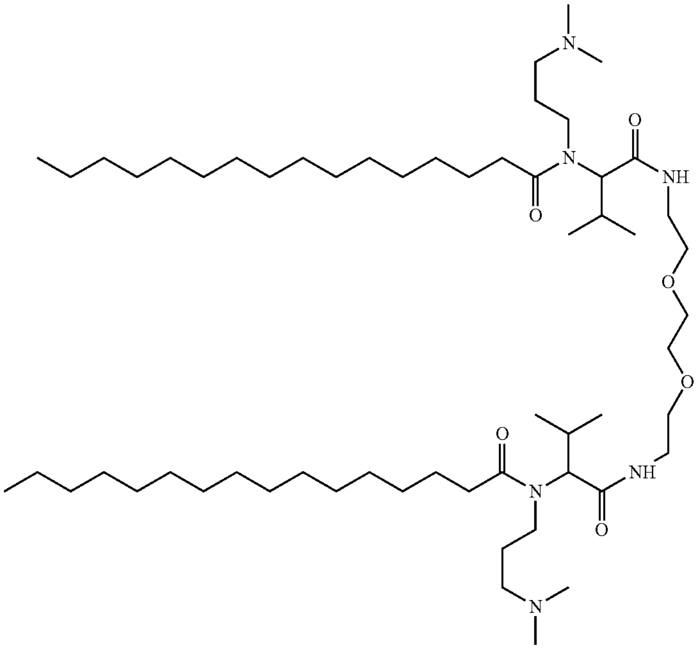 I2R2C16A1 |
| 46 | I2 | R2 | C18 | A1 | 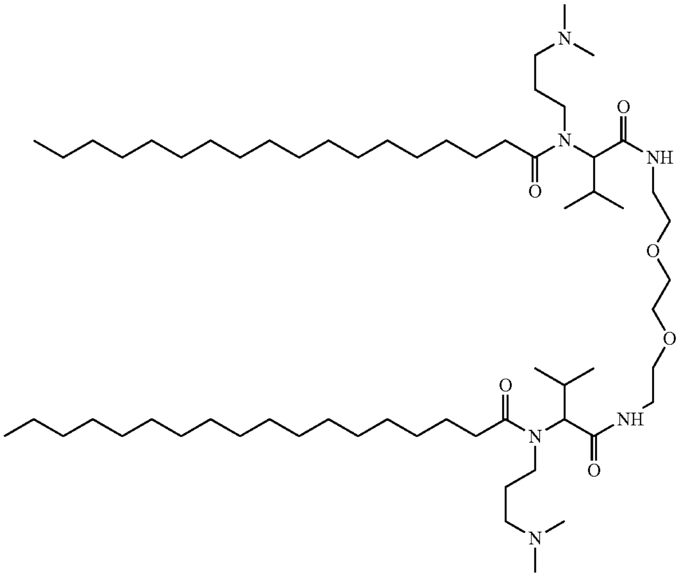 I2R2C18A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 47 | I2 | R2 | C20 | A1 | 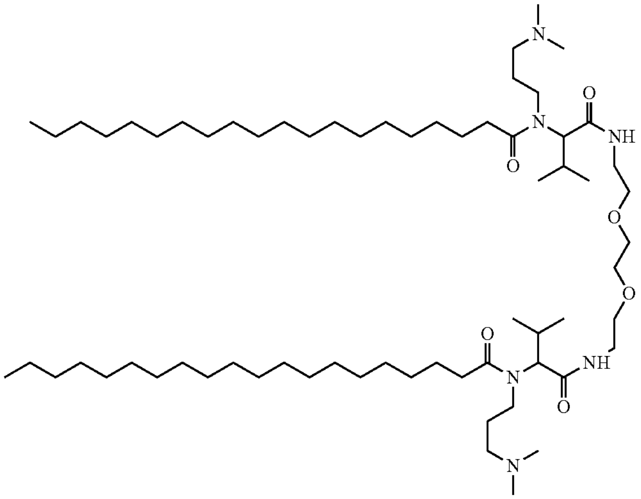 I2R2C20A1 |
| 48 | I2 | R2 | C18-1 | A1 | 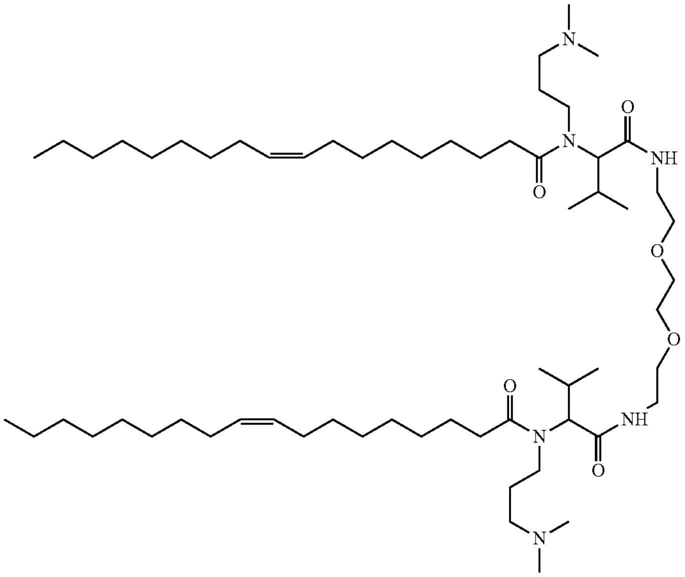 I2R2C18-1A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 49 | I2 | R2 | C18-2 | A1 | 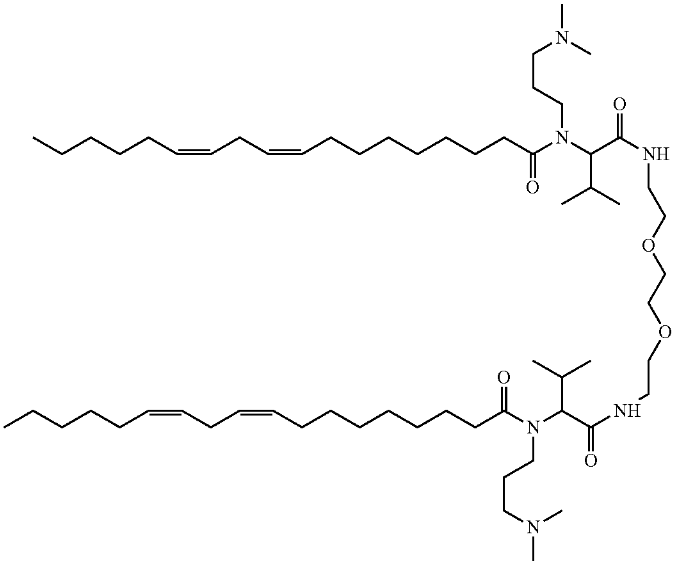 [SMILES: CCCCC/C=C\C/C=C\CCCCCCCC(=O)N(CCCN(C)C)C(C(=O)NCCOCCOCCNC(=O)C(C(C)C)N(CCCN(C)C)C(=O)CCCCCCC/C=C\C/C=C\CCCCC)C(C)C] I2R2C18-2A1 |
| 50 | I2 | R3 | C12 | A1 | 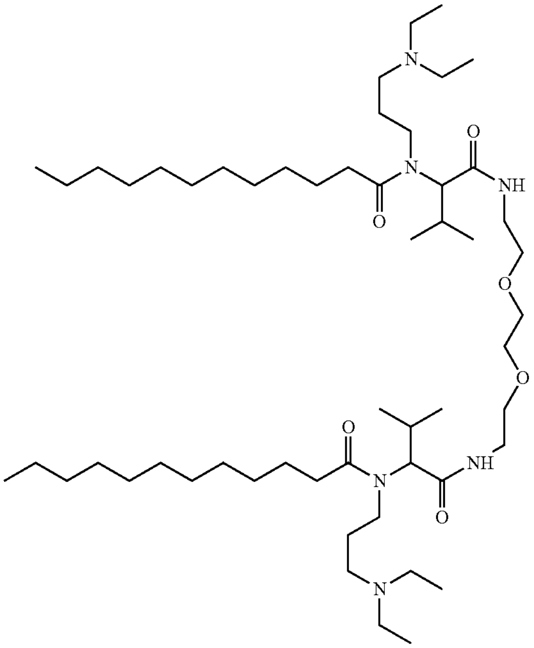 [SMILES: CCCCCCCCCCCC(=O)N(CCCN(CC)CC)C(C(=O)NCCOCCOCCNC(=O)C(C(C)C)N(CCCN(CC)CC)C(=O)CCCCCCCCCCC)C(C)C] I2R3C12A1 |

TABLE 1-continued
| | Iso-cyanide com-pound | Amine com-pound | Car-boxylic acid com-pound | Aldehyde compound | Cationic lipid analog material (number and structure formula) |
|---|---|---|---|---|---|
| 51 | I2 | R3 | C14 | A1 | 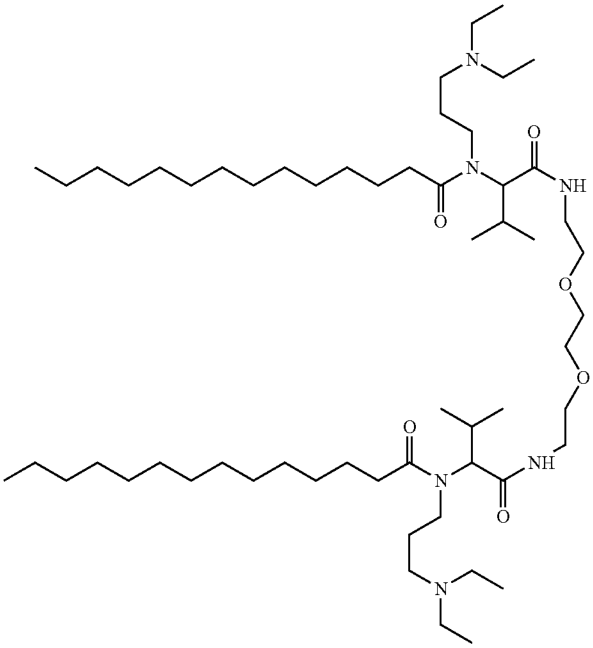 [SMILES: CCCCCCCCCCCCCC(=O)N(CCCN(CC)CC)C(C(=O)NCCOCCOCCNC(=O)C(C(C)C)N(CCCN(CC)CC)C(=O)CCCCCCCCCCCCC)C(C)C]<br>I2R3C14A1 |
| 52 | I2 | R3 | C16 | A1 | 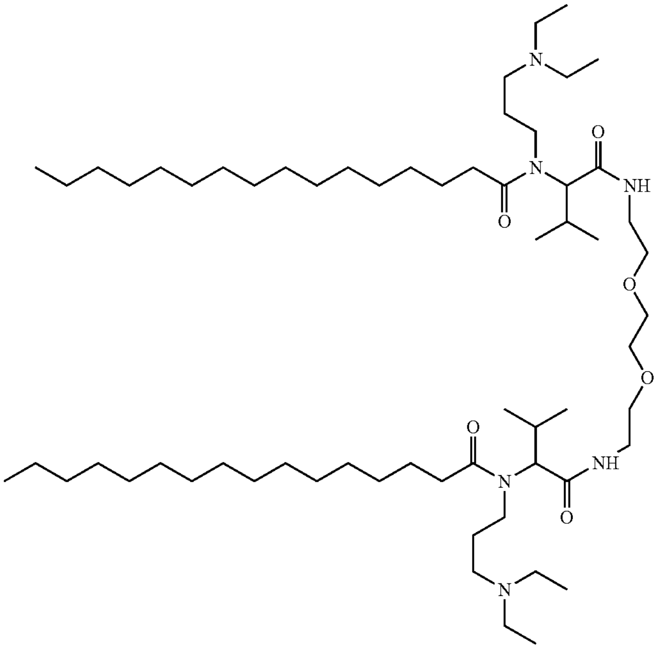 [SMILES: CCCCCCCCCCCCCCCC(=O)N(CCCN(CC)CC)C(C(=O)NCCOCCOCCNC(=O)C(C(C)C)N(CCCN(CC)CC)C(=O)CCCCCCCCCCCCCCC)C(C)C]<br>I2R3C16A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 53 | I2 | R3 | C18 | A1 | 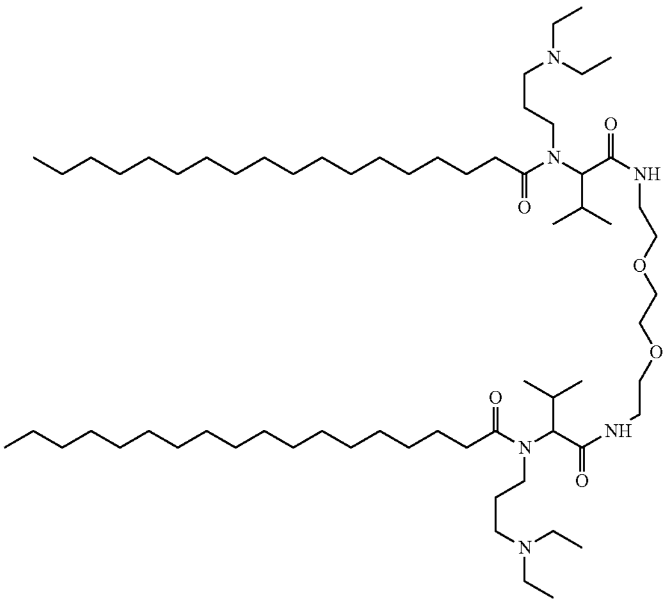 I2R3C18A1 |
| 54 | I2 | R3 | C20 | A1 | 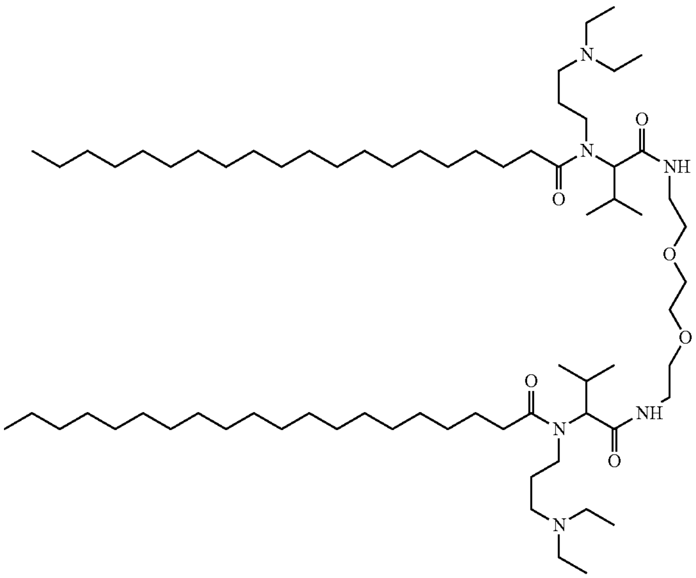 I2R3C20A1 |

TABLE 1-continued
| | Isocyanide compound | Amine compound | Carboxylic acid compound | Aldehyde compound | Cationic lipid analog material (number and structure formula) |
|---|---|---|---|---|---|
| 55 | I2 | R3 | C18-1 | A1 | 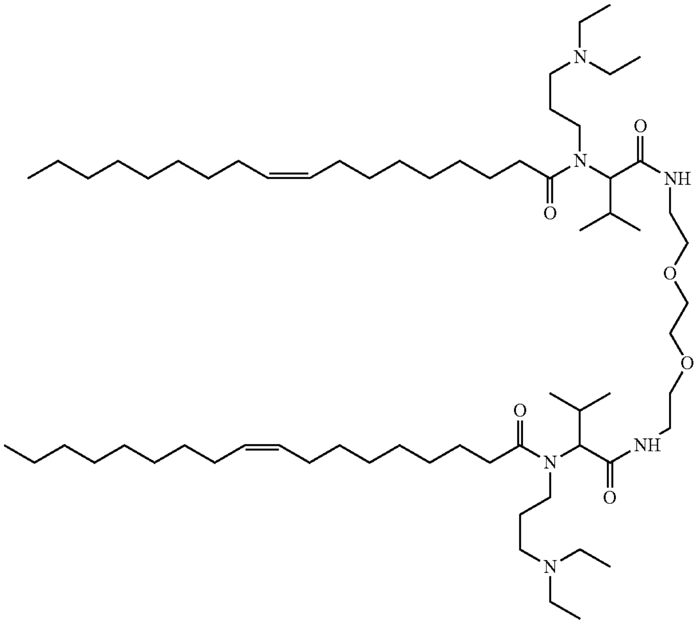 [SMILES: CCCCCCCC/C=C\CCCCCCCC(=O)N(CCCN(CC)CC)C(C(=O)NCCOCCOCCNC(=O)C(C(C)C)N(CCCN(CC)CC)C(=O)CCCCCCC/C=C\CCCCCCCC)C(C)C] I2R3C18-1A1 |
| 56 | I2 | R3 | C18-2 | A1 | 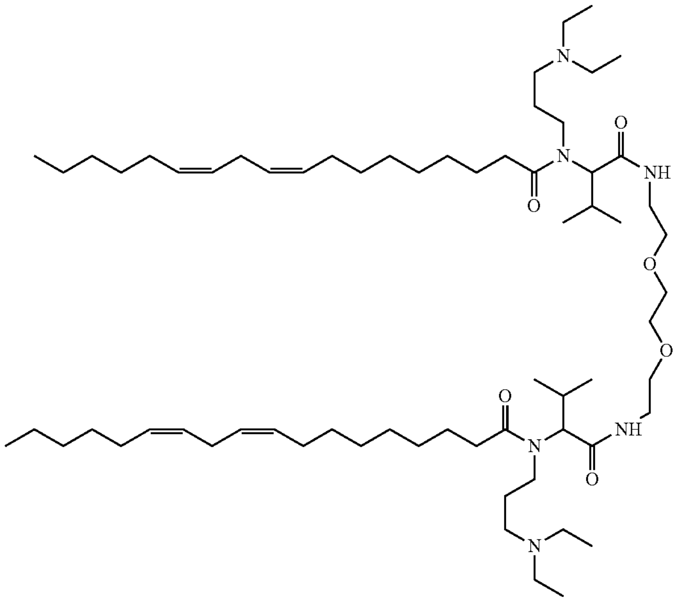 [SMILES: CCCCC/C=C\C/C=C\CCCCCCCC(=O)N(CCCN(CC)CC)C(C(=O)NCCOCCOCCNC(=O)C(C(C)C)N(CCCN(CC)CC)C(=O)CCCCCCC/C=C\C/C=C\CCCCC)C(C)C] I2R3C18-2A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 57 | I2 | R5 | C12 | A1 | 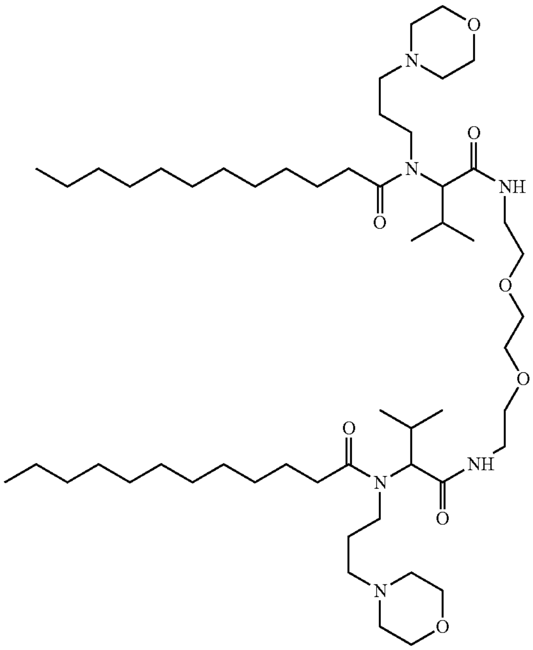 I2R5C12A1 |
| 58 | I2 | R5 | C14 | A1 | 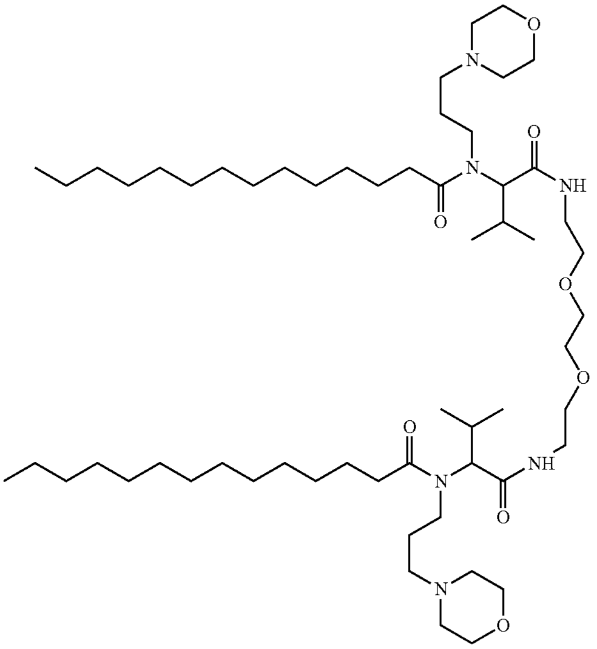 I2R5C14A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 59 | I2 | R5 | C16 | A1 | 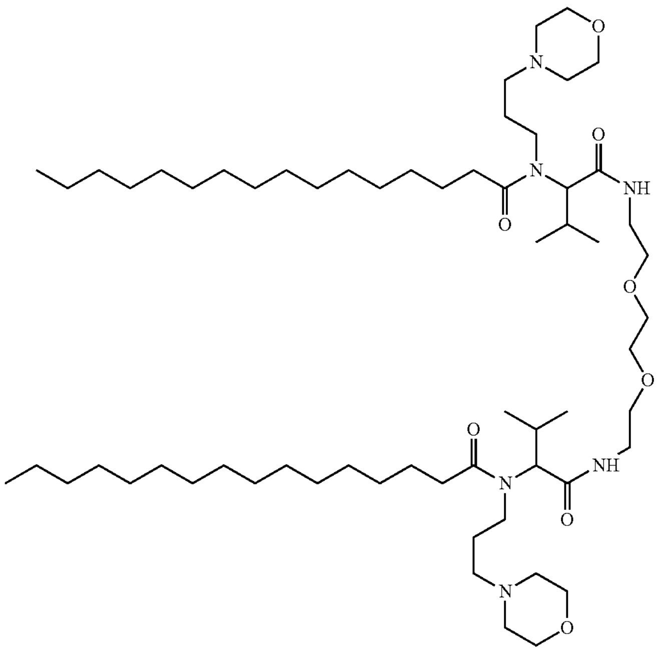 I2R5C16A1 |
| 60 | I2 | R5 | C18 | A1 | 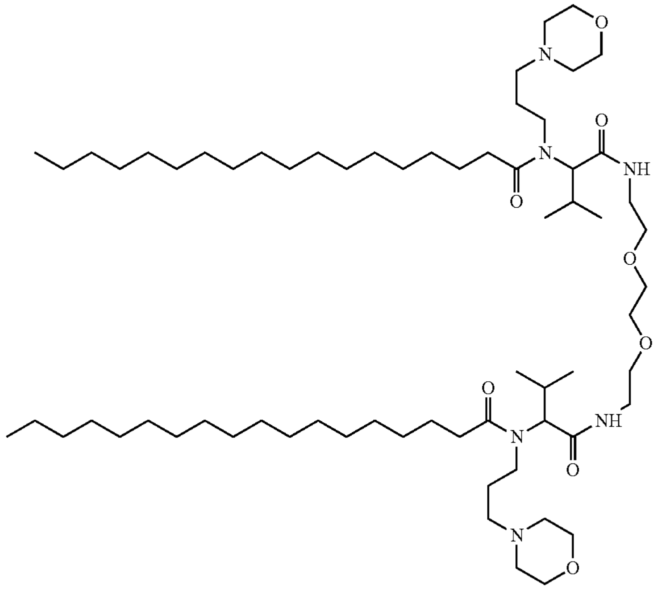 I2R5C18A1 |

TABLE 1-continued
| | Iso-cyanide com-pound | Amine com-pound | Car-boxylic acid com-pound | Aldehyde compound | Cationic lipid analog material (number and structure formula) |
|---|---|---|---|---|---|
| 61 | I2 | R5 | C20 | A1 | 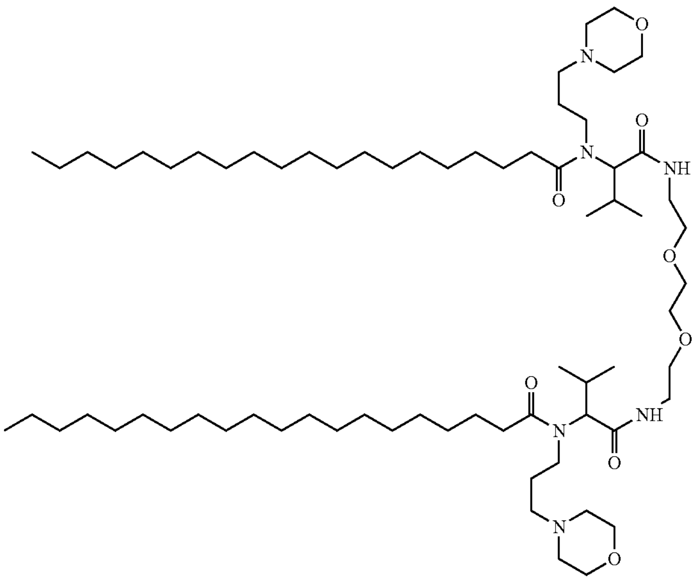 I2R5C20A1 |
| 62 | I2 | R5 | C18-1 | A1 | 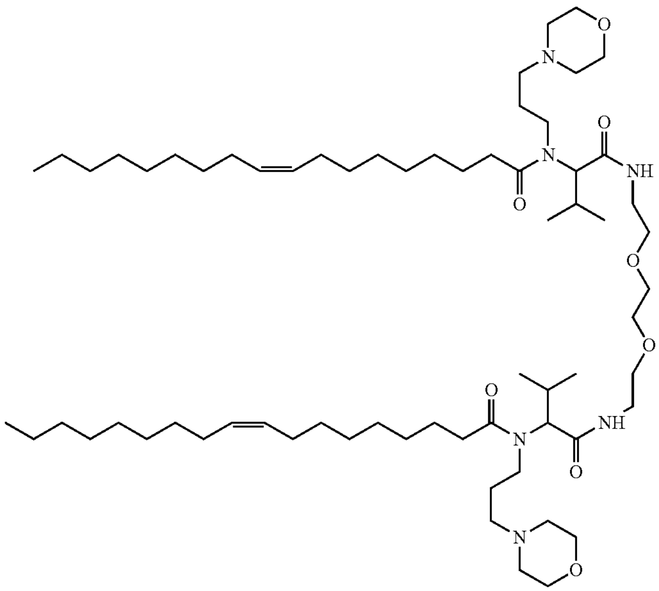 I2R5C18-1A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 63 | I2 | R5 | C18-2 | A1 | 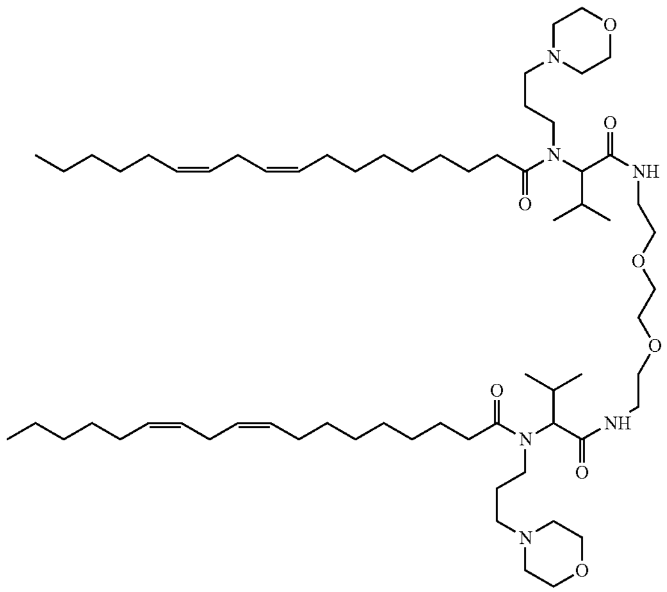 [SMILES: CCCCC/C=C\C/C=C\CCCCCCCC(=O)N(CCCN1CCOCC1)C(C(=O)NCCOCCOCCNC(=O)C(C(C)C)N(CCCN1CCOCC1)C(=O)CCCCCCC/C=C\C/C=C\CCCCC)C(C)C] I2R5C18-2A1 |
| 64 | I2 | R11 | C12 | A1 | 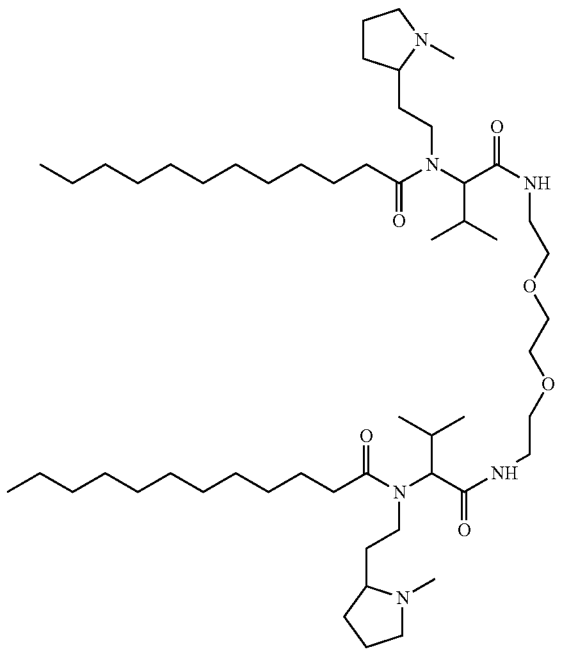 [SMILES: CCCCCCCCCCCC(=O)N(CCC1CCCN1C)C(C(=O)NCCOCCOCCNC(=O)C(C(C)C)N(CCC1CCCN1C)C(=O)CCCCCCCCCCC)C(C)C] I2R11C12A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 65 | I2 | R11 | C14 | A1 | 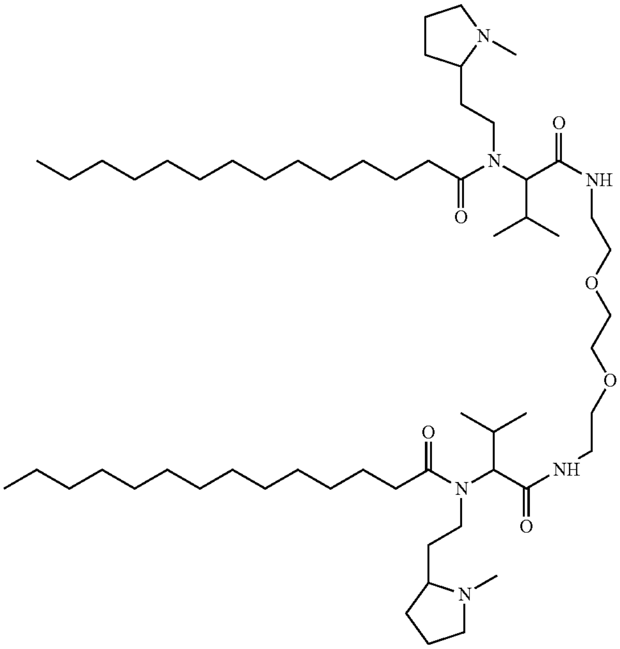 I2R11C14A1 |
| 66 | I2 | R11 | C16 | A1 | 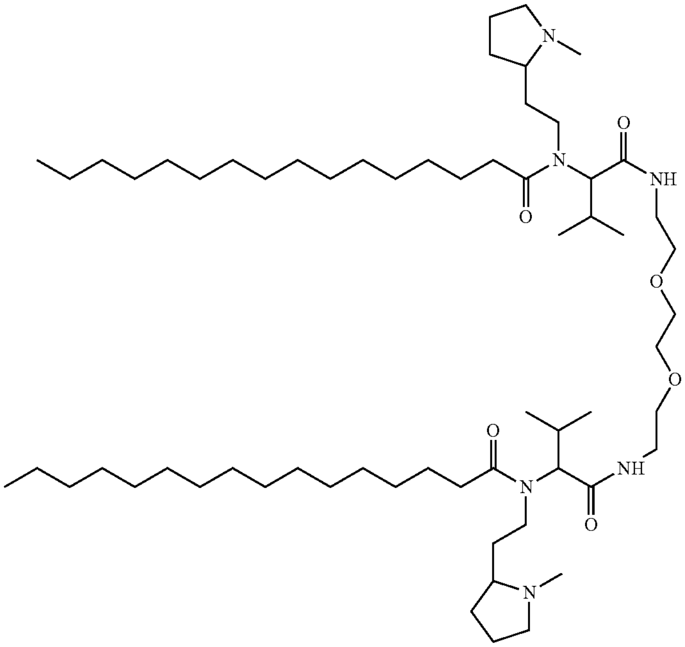 I2R11C16A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 67 | I2 | R11 | C18 | A1 | 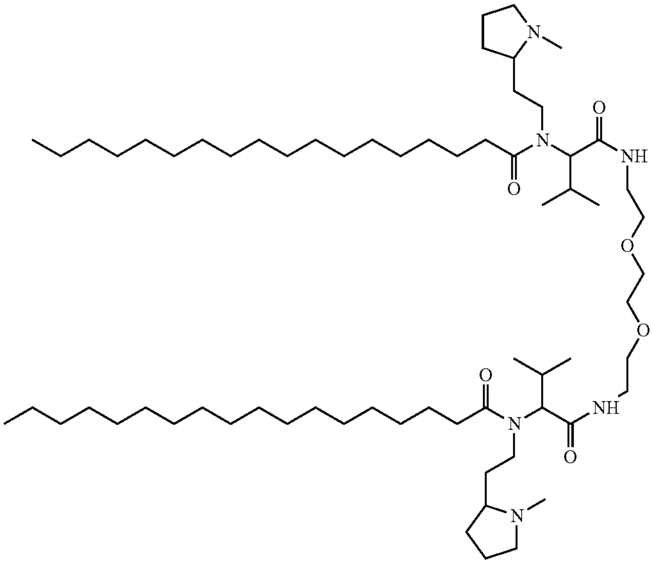 I2R11C18A1 |
| 68 | I2 | R11 | C20 | A1 | 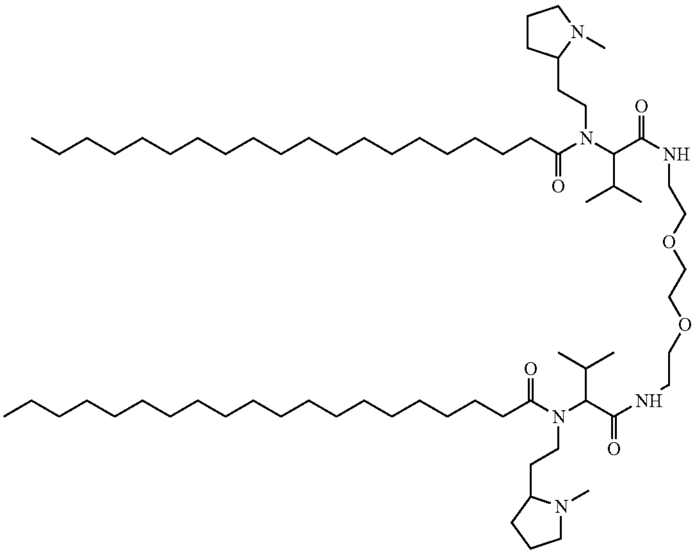 I2R11C20A1 |

TABLE 1-continued
| | Isocyanide compound | Amine compound | Carboxylic acid compound | Aldehyde compound | Cationic lipid analog material (number and structure formula) |
|---|---|---|---|---|---|
| 69 | I2 | R11 | C18-1 | A1 | 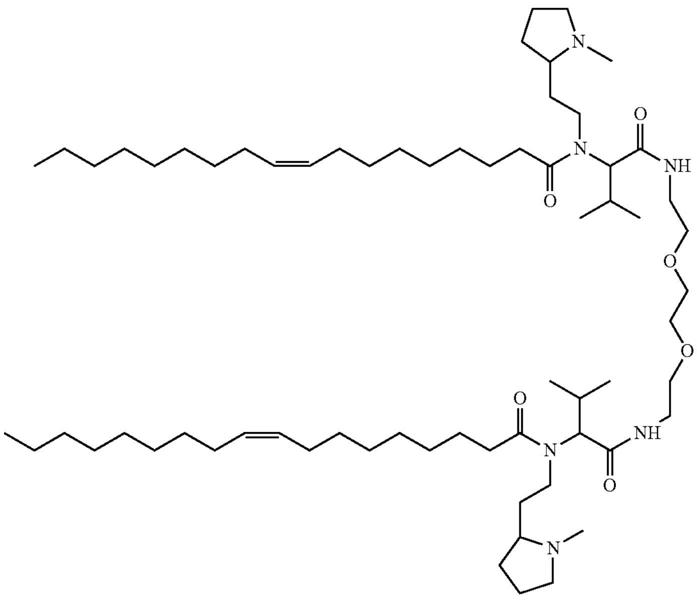 [SMILES: CCCCCCCC/C=C\CCCCCCCC(=O)N(CCC1CCCN1C)C(C(=O)NCCOCCOCCNC(=O)C(C(C)C)N(CCC1CCCN1C)C(=O)CCCCCCC/C=C\CCCCCCCC)C(C)C] I2R11C18-1A1 |
| 70 | I2 | R11 | C18-2 | A1 | 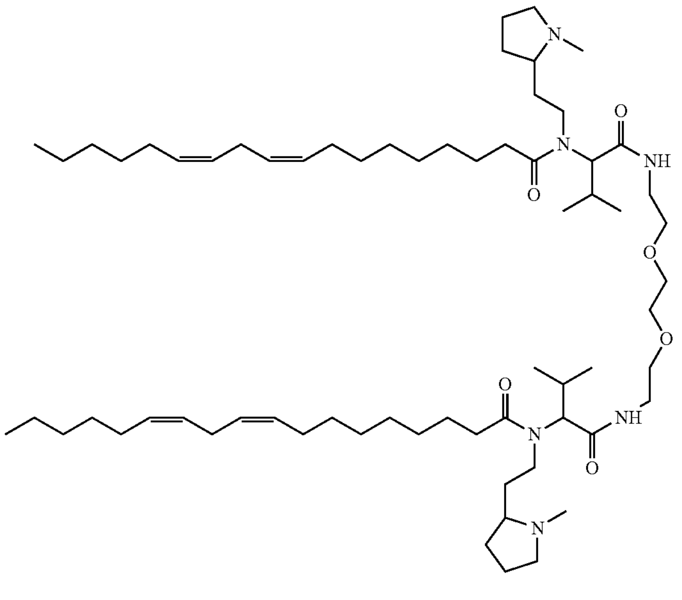 [SMILES: CCCCC/C=C\C/C=C\CCCCCCCC(=O)N(CCC1CCCN1C)C(C(=O)NCCOCCOCCNC(=O)C(C(C)C)N(CCC1CCCN1C)C(=O)CCCCCCC/C=C\C/C=C\CCCCC)C(C)C] I2R11C18-2A1 |

TABLE 1-continued
| | Iso-cyanide compound | Amine compound | Carboxylic acid compound | Aldehyde compound | Cationic lipid analog material (number and structure formula) |
|---|---|---|---|---|---|
| 71 | 12-1 | R2 | C18 | A1 | 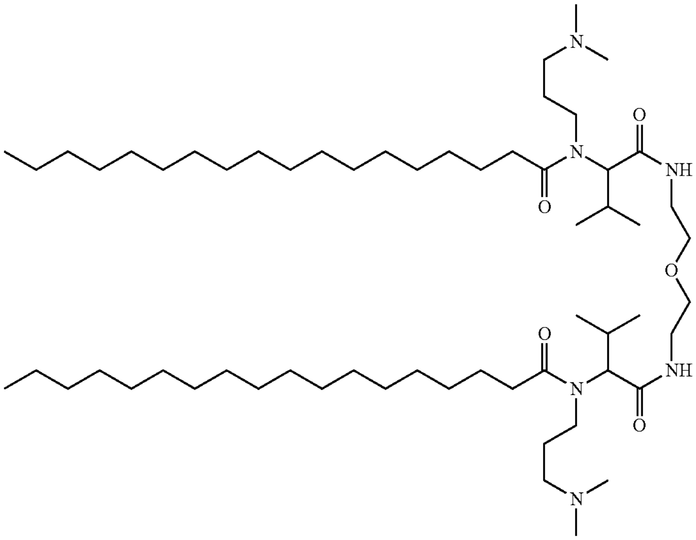 [SMILES: CCCCCCCCCCCCCCCCCC(=O)N(CCCN(C)C)C(C(=O)NCCOCCNC(=O)C(C(C)C)N(CCCN(C)C)C(=O)CCCCCCCCCCCCCCCCC)C(C)C] I2-1R2C18A1 |
| 72 | 12-3 | R2 | C18 | A1 | 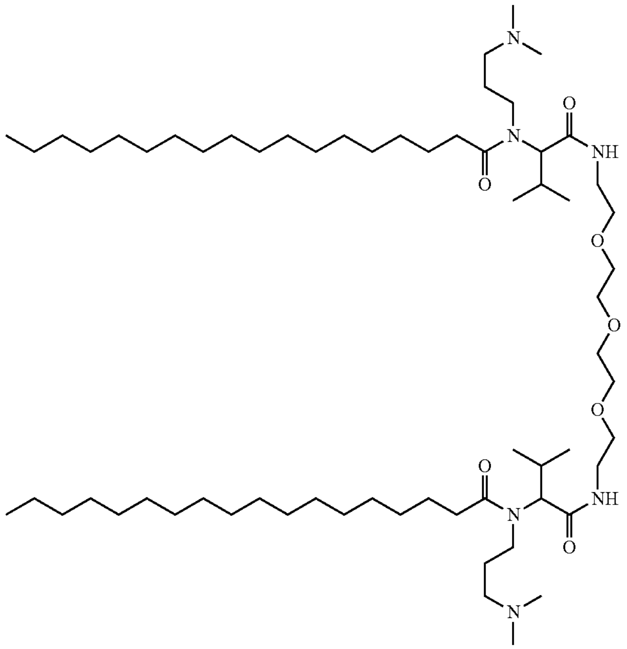 [SMILES: CCCCCCCCCCCCCCCCCC(=O)N(CCCN(C)C)C(C(=O)NCCOCCOCCOCCNC(=O)C(C(C)C)N(CCCN(C)C)C(=O)CCCCCCCCCCCCCCCCC)C(C)C] I2-3R2C18A1 |

Figure 1A:
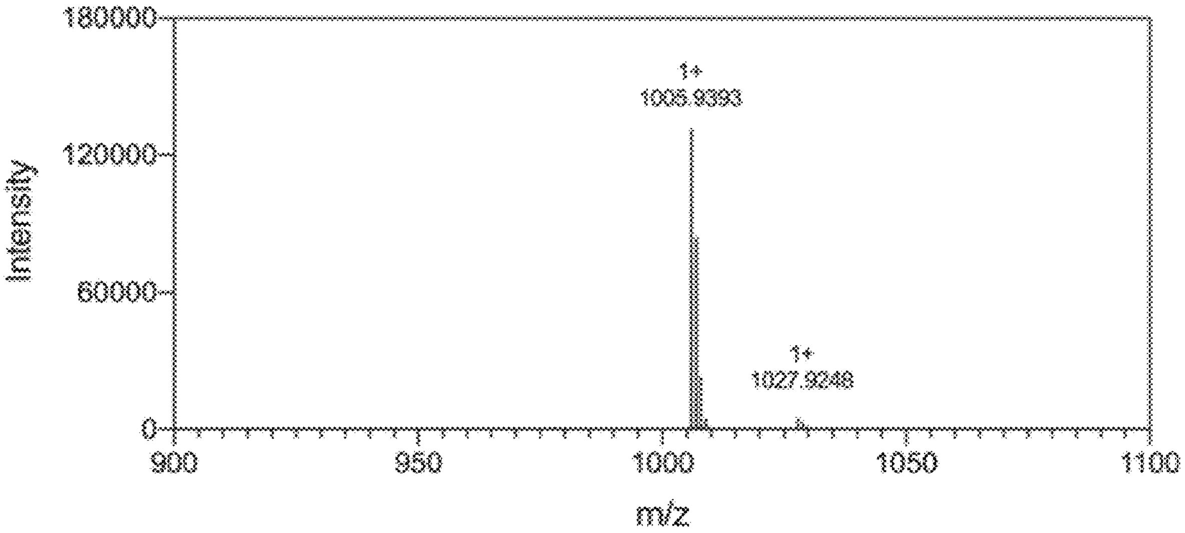
FIG. 1A shows a mass spectrometry spectrum of cationic lipid analog material 12-1R2C18A1.
Figure 1B:
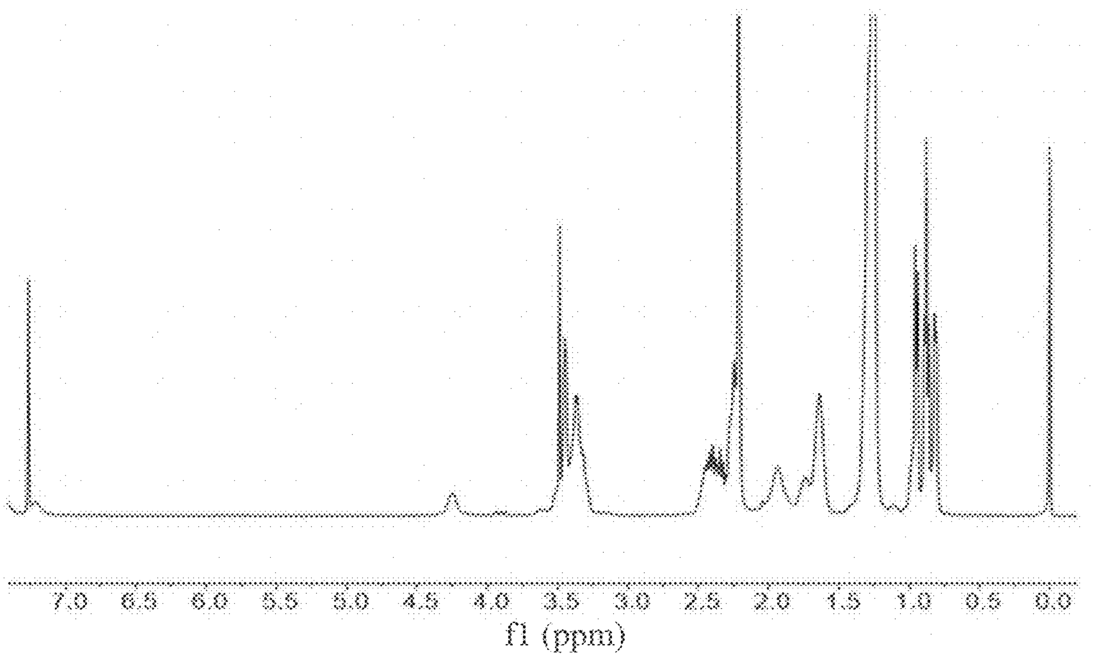
FIG. 1B shows a proton nuclear magnetic resonance spectrum of cationic lipid analog material 12-1R2C18A1.
Figure 2A:
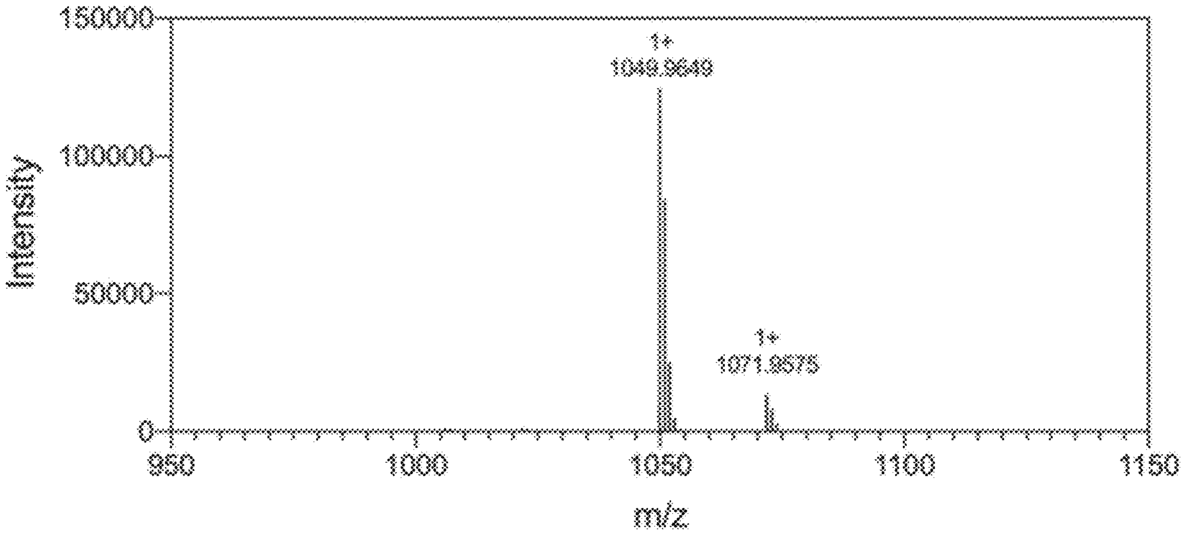
FIG. 2A shows a mass spectrometry spectrum of cationic lipid analog material I2R2C18A1.
Figure 2B:
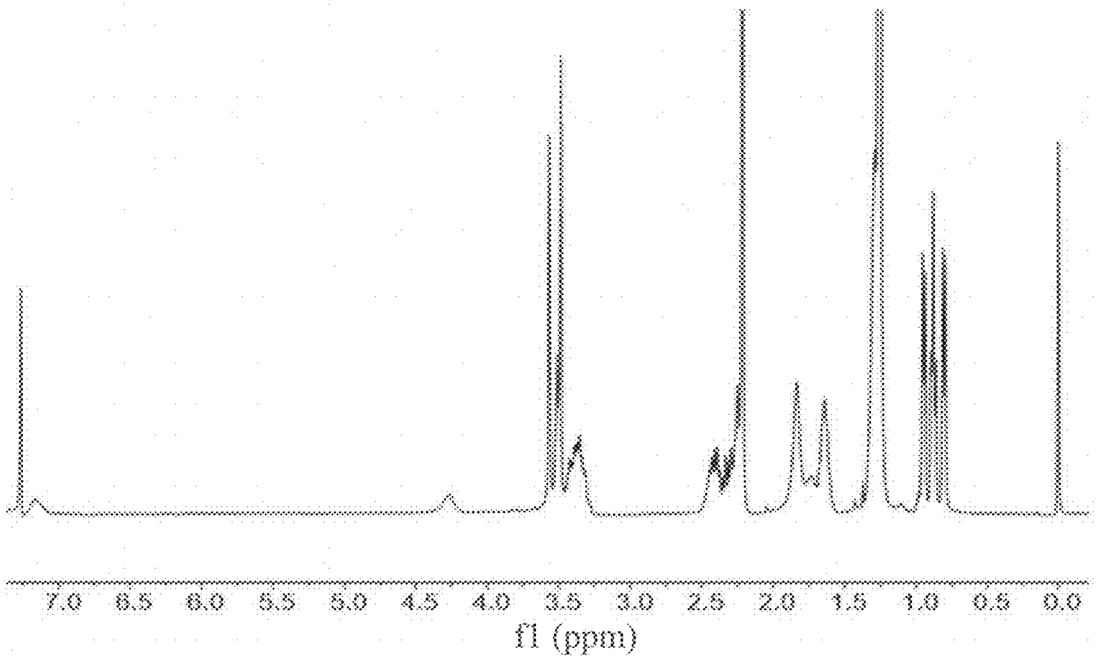
FIG. 2B shows a proton nuclear magnetic resonance spectrum of cationic lipid analog material I2R2C18A1.
Figure 3A:
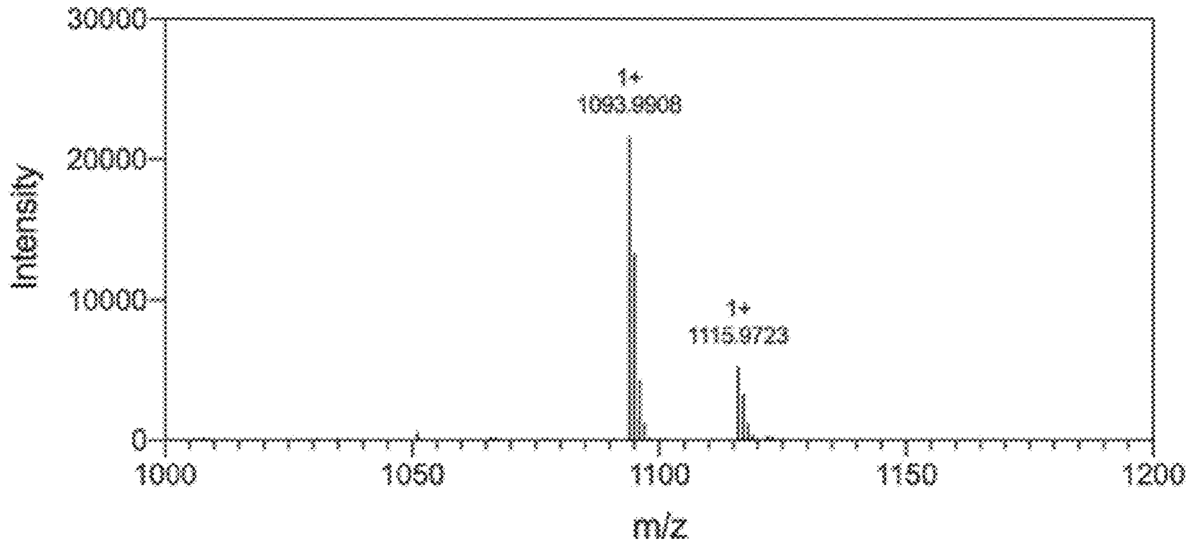
FIG. 3A shows a mass spectrometry spectrum of cationic lipid analog material 12-3R2C18A1.
Figure 3B:
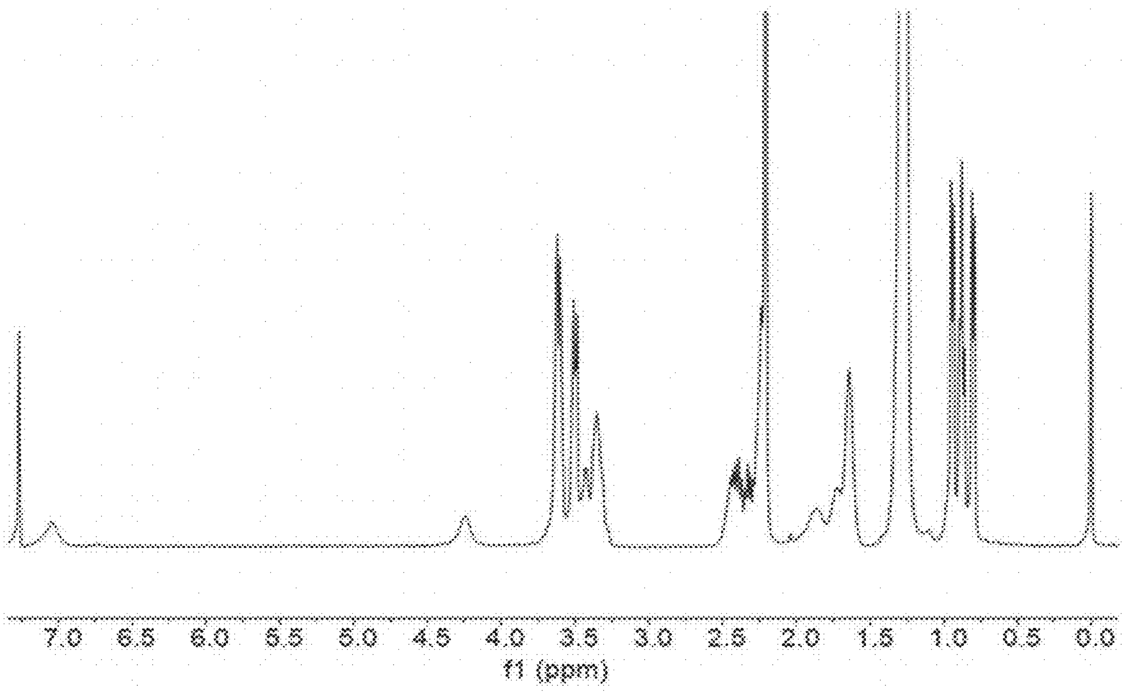
FIG. 3B shows a proton nuclear magnetic resonance spectrum of cationic lipid analog material I2-3R2C18A1.

Cationic lipid analog materials I2-1R2C18A1, I2R2C18A1, and I2-3R2C18A1 were selected as representative materials, and structures of these materials were characterized, where mass spectrometry and proton nuclear magnetic resonance spectra of I2-1R2C18A1 were shown in FIG. 1A and FIG. 1B; mass spectrometry and proton nuclear magnetic resonance spectra of I2R2C18A1 were shown in FIG. 2A and FIG. 2B; and mass spectrometry and proton nuclear magnetic resonance spectra of I2-3R2C18A1 were shown in FIG. 3A and FIG. 3B. Results of proton nuclear magnetic resonance and mass spectrometry were consistent with the expected structures of the cationic lipid analog materials.

Example 2 Transfection Experiment of GFP-Expressing Plasmid DNA

In this experiment, with GFP-expressing plasmid DNA as a reporter gene, a gene transfection efficiency of a cationic lipid analog material in Hela cells was detected. A specific method was as follows:

Hela cells were inoculated in a 24-well plate and cultured in an incubator for 12 h; each of different cationic lipid analog materials (0.25 μg/well to 8 μg/well) was mixed with GFP-expressing plasmid DNA (0.5 μg/well) in 40 μL of a sodium acetate buffer (25 mM, pH 5.2), and resulting mixtures each were allowed to stand for 10 min and then diluted with 460 μL of an Opti-MEM medium to obtain plasmid DNA-loaded cationic lipid analog complex particle solutions; a medium for the Hela cells in the plate was removed, then the HeLa cells were washed once with PBS, and the complex particle solutions were added; and the cells were cultured for 24 h, and then a plasmid DNA transfection efficiency in cells was analyzed by a flow cytometer. A commercial gene transfection reagent Lipofectamine 2000 was adopted as a positive control.

Figure 4:
FIG. 4 shows positive rates of GFP-expressing plasmid DNA after transfection by different cationic lipid analog materials, where a dosage of I2R11C14A1 and I2R11C18-2A1 is 0.5 μg/well; a dosage of I1R2C14A1, I2R1C16A1, I2R1C18A1, I2R1C18-1A1, I2R1C18-2A1, I2R2C18-2A1, I2R3C14A1, I2R3C16A1, and I2R3C18-2A1 is 1 μg/well; a dosage of I1R2C16A1, I1R2C18-1A1, 11R2C18-2A1, 11R3C14A1, I1R3C16A1, 11R3C18-2A1, I1R11C14A1, I1R11C16A1, 11R11C18A1, 11R11C18-1A1, 11R11C18-2A1, I2R1C14A1, I2R2C14A1, I2R2C16A1, I2R2C18-1A1, I2R3C18A1, I2R3C18-1A1, and I2R11C16A1 is 2 μg/well; a dosage of I1R1C16A1, 11R2C18A1, 11R3C12A1, 11R3C18A1, I1R3C18-1A1, I1R11C12A1, I2R2C18A1, I2R11C12A1, I2R11C18A1, and I2R11C18-1A1 is 4 μg/well; and a dosage of I1R1C12A1, 11R1C14A1, 11R1C18A1, 11R1C18-1A1, 11R1C18-2A1, 11R2C12A1, I1R5C12A1, 11R5C14A1, 11R5C16A1, 11R5C18A1, 11R5C18-1A1, 11R5C18-2A1, I2R1C12A1, I2R2C12A1, I2R3C12A1, I2R5C12A1, I2R5C14A1, I2R5C16A1, I2R5C18A1, I2R5C18-1A1, and I2R5C18-2A1 is 8 μg/well.

It can be seen from the results in FIG. 4 that the cationic lipid analog material of the present application can transfect GFP-expressing plasmid DNA into Hela cells, and in particular, a transfection efficiency of 11R2C14A1, 11R2C18-2A1, 11R11C14A1, I2R1C14A1, I2R1C16A1, I2R1C18-1A1, I2R1C18-2A1, I2R2C14A1, I2R2C16A1, I2R2C18-1A1, I2R2C18-2A1, I2R3C16A1, I2R3C18A1, I2R3C18-1A1, I2R3C18-2A1, I2R11C14A1, I2R11C16A1, I2R11C18A1, I2R11C18-1A1, and I2R11C18-2A1 can be equivalent to or higher than a transfection efficiency of the commercial transfection reagent Lipofectamine 2000.

Example 3 Transfection Experiment of Luciferase (Luminescence)-Expressing Plasmid DNA In this example, with luciferase-expressing plasmid DNA as a reporter gene, a gene transfection efficiency of a cationic lipid analog material in HeLa cells was detected. A specific operation method was as follows: Hela cells were inoculated in a 96-well plate and cultured in an incubator for 12 h; each of different cationic lipid analog materials was mixed with luciferase-expressing plasmid DNA (0.5 μg) in 40 μL of a sodium acetate buffer (25 mM, pH 5.2), and resulting mixtures each were allowed to stand for 10 min and then diluted with 460 μL of an Opti-MEM medium to obtain plasmid DNA-loaded cationic lipid analog complex particle solutions; a medium for the Hela cells in the plate was removed, then the Hela cells were washed once with PBS, and the complex particle solutions were added in a volume of 125 μL; the cells were cultured for 24 h, then a resulting culture supernatant was discarded, and the cells were fully lysed; and a substrate was added at 50 μl/well, and an expression level of luciferase was detected by a multi-mode microplate reader.

Figure 5:
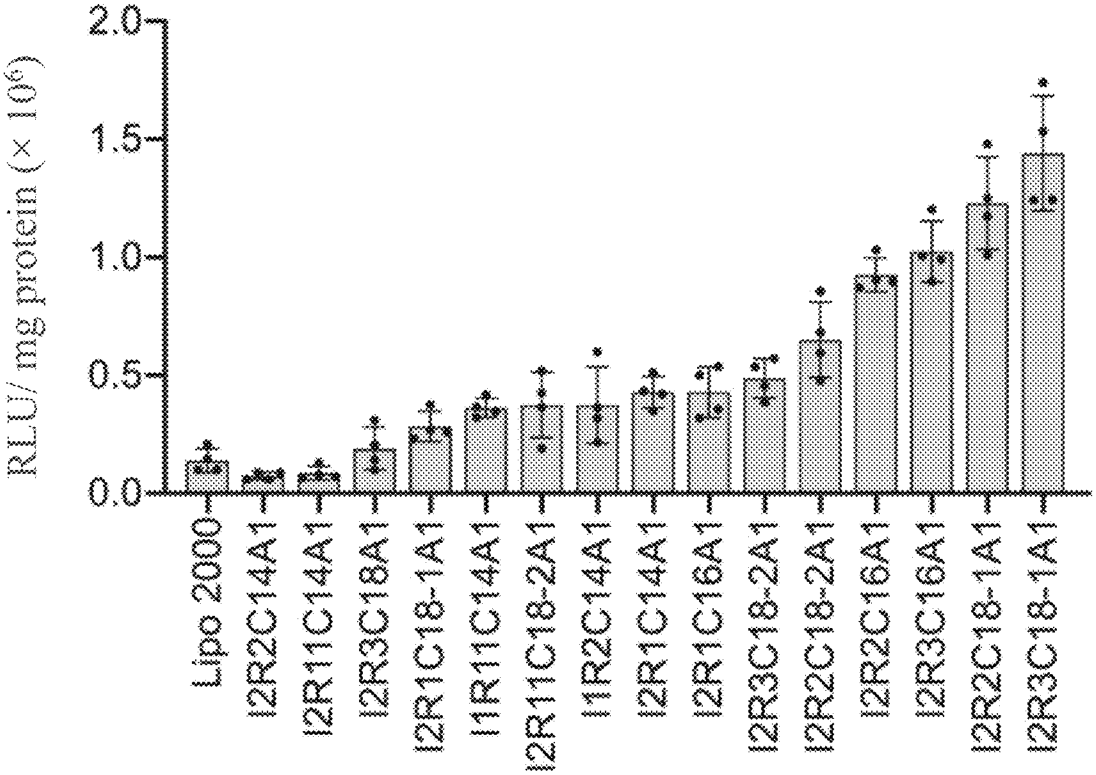
FIG. 5 shows detection results of luciferase expression in Hela cells transfected with luciferase-expressing plasmid DNA by different cationic lipid analog materials.

It can be seen from the results in FIG. 5 that a transfection efficiency of I2R3C18A1. I2R1C18-1A1, I1R11C14A1, I2R11C18-2A1, 11R2C14A1, I2R1C14A1, I2R1C16A1, I2R3C18-2A1, I2R2C18-2A1, I2R2C16A1, I2R3C16A1, I2R2C18-1A1, and I2R3C18-1A1 can be equivalent to or higher than a transfection efficiency of the commercial transfection reagent Lipofectamine 2000.

Example 4 Transfection Effects of I2R3C18-1A1 for GFP-Expressing Plasmid DNA in Different Types of Cells In this experiment, with I2R3C18-1A1 as a representative cationic lipid analog material and GFP-expressing plasmid DNA as a reporter gene, transfection effects of the cationic lipid analog material at different dosages (0.5 μg/well to 3 μg/well) for plasmid DNA (0.5 μg/well) in different types of cells were investigated. A commercial gene transfection reagent Lipofectamine 2000 was adopted as a positive control. In this experiment, a GFP-expressing plasmid DNA-loaded I2R3C18-1A1 particle complex solution was prepared with reference to the method in Example 2 and added to DC2.4, RAW 264.7, A549, BxPC3, and HeLa cells respectively, these cells were cultured for 24 h, and then a transfection efficiency of plasmid DNA in cells was observed by LSCM.

Figure 6:
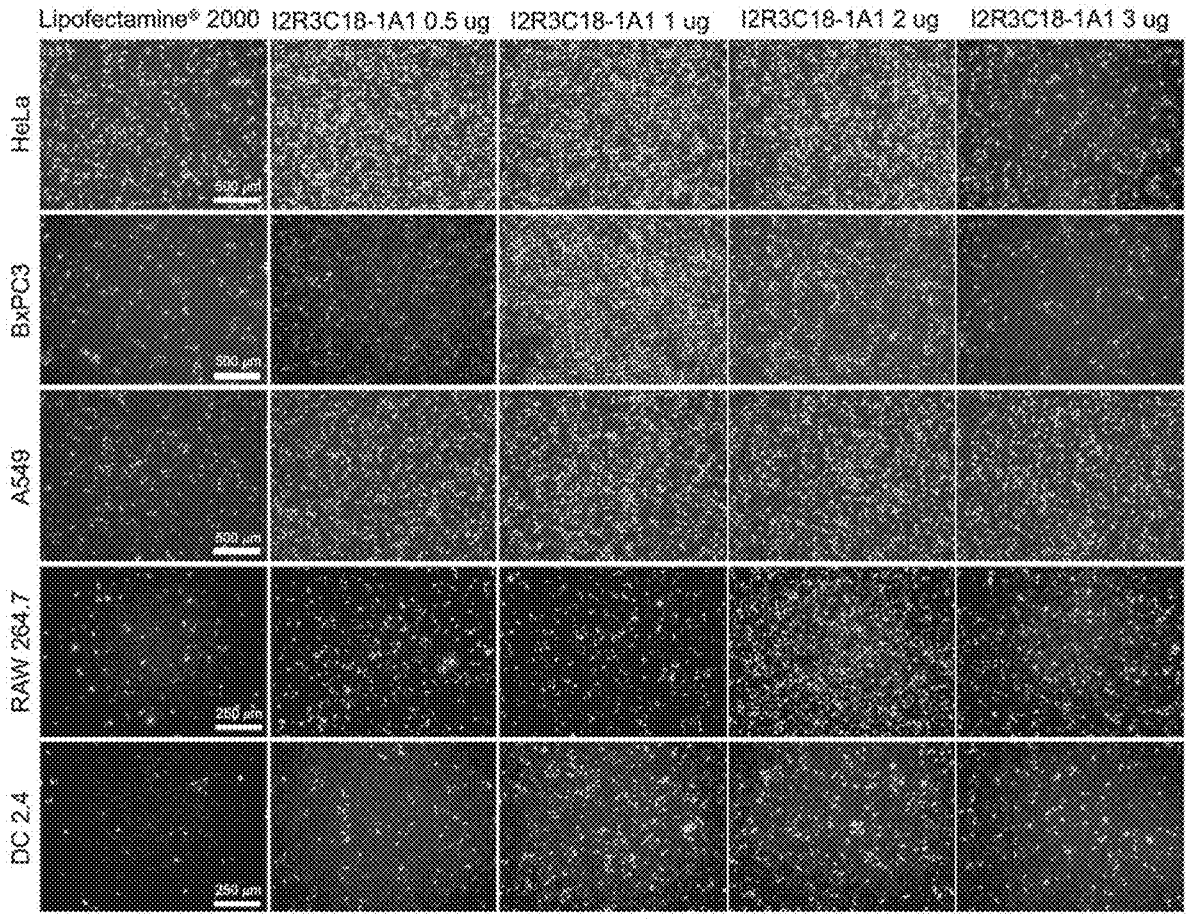
FIG. 6 shows LSCM results of different types of cells transfected with GFP-expressing plasmid DNA by I2R3C18-1A1 with different doses.

The results in FIG. 6 show that the I2R3C18-1A1 material can transfect GFP-expressing plasmid DNA into tumor cells and immune cells.

Example 5 Transfection Experiment of Enhanced Green Fluorescent Protein (cGFP)-Expressing mRNA In this experiment, with eGFP-mRNA as model mRNA, an mRNA transfection efficiency of a cationic lipid analog material in DC 2.4 cells was detected. A specific operation method was as follows:

DC 2.4 cells were inoculated in a 48-well plate and cultured in an incubator for 12 h; each of different cationic lipid analog materials (0.25 μg/well to 2 μg/well) was mixed with eGFP-expressing mRNA (0.2 μg/well) in 20 μL of a sodium acetate buffer (25 mM, pH 5.2), and resulting mixtures each were allowed to stand for 10 min and then diluted with 230 μL of a Opti-MEM medium to obtain mRNA-loaded complex particle solutions; a medium for the DC 2.4 cells in the plate was removed, then the DC 2.4 cells were washed once with PBS, and the complex particle solutions were added; and the cells were cultured for 24 h, an mRNA transfection efficiency in cells was observed by FCM and LSCM. A commercial gene transfection reagent Lipofectamine 2000 was adopted as a positive control.

The results in FIG. 7, FIG. 8, and FIG. 9 show that the cationic lipid analog material of the present application can transfect eGFP-expressing mRNA into DC 2.4 cells, and in particular, an mRNA transfection efficiency of 11R2C14A1, 11R2C16A1, 11R2C18A1, 11R2C18-1A1, I1R2C18-2A1, I1R11C14A1, I1R11C16A1, 11R11C18A1, I2R1C14A1, I2R1C16A1, I2R1C18-1A1, I2R2C14A1, I2R2C16A1, I2R2C18A1, I2R2C18-1A1, I2R2C18-2A1, I2R3C14A1, I2R3C16A1, I2R3C18A1, I2R3C18-1A1, I2R3C18-2A1, I2R11C14A1, I2R11C16A1, I2R11C18A1, I2R11C18-1A1, and I2R11C18-2A1 can be equivalent to or higher than an mRNA transfection efficiency of the commercial transfection reagent Lipofectamine 2000.

Example 6 Transfection Experiment of Small Interfering Ribonucleic Acid (siRNA)

In this experiment, with I2R2C18-1A1, I2R3C18-1A1, I2R2C18-2A1, and I2R3C18-2A1 as representative cationic lipid analog materials, siRNA transfection and delivery effects of the cationic lipid analog materials were detected in A549 cells (A549-Luc). A specific operation method was as follows:

Luciferase-expressing A549 cells (A549-Luc) were inoculated in a 96-well plate and cultured in an incubator for 12 h; each of different materials (0.5 μg/well to 3 μg/well) was mixed with siRNA in 40 μL of a sodium acetate buffer (25 mM, pH 5.2), and resulting mixtures each were allowed to stand for 10 min and then diluted with 460 μL of an Opti-MEM medium to obtain siRNA-loaded complex particle solutions (final siRNA concentration was 100 nM); a medium for the A549-Luc cells in the plate was removed, then the A549-Luc cells were washed once with PBS, and the complex particle solutions each were added in a volume of 125 μL; the cells were cultured for 48 h, then a resulting culture supernatant was discarded, and the cells were fully lysed; and a substrate was added at 50 μl/well, and an expression level of luciferase was detected by a multi-mode microplate reader.

The results in FIG. 10 show that I2R2C18-1A1, I2R3C18-1A1, I2R2C18-2A1, and I2R3C18-2A1 can transfect siRNA into cells to specifically silence the expression of the luciferase reporter gene, and the gene silencing efficiency increases with the increase of a dosage of the cationic lipid analog material.

Example 7 Cytotoxicity Test of Cationic Lipid Analog Materials

In this experiment, I2R2C16A1, I2R2C17A1, I2R2C18A1, I2R2C19A1, and I2R2C20A1 with high transfection efficiencies were selected as representative cationic lipid analog materials, and the toxicity of cationic lipid analogs for Hela cells was detected by an MTT experiment. A specific experimental method was as follows: HeLa cells were inoculated in a 96-well plate and cultured in an incubator for 12 h, then a medium was removed, and a cationic lipid analog material was added at 1 μg/ml; the cells were cultured for 4 h, then the material was washed away and replaced with DMEM; and the cells were cultured for 20 h, and finally cell viability was detected by MTT.

The results in FIG. 11 show that the cationic lipid analog materials I2R2C16A1, I2R2C17A1, I2R2C18A1, I2R2C19A1, and I2R2C20A1 of the present application have low cytotoxicity and excellent biocompatibility.

In addition, the inventors have found in previous research that, when the isobutyl aldehyde in Example 1 is replaced by

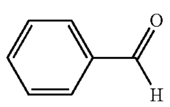 and 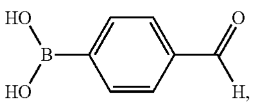, cationic lipid analog materials prepared correspondingly also have low cytotoxicity; GFP-expressing plasmid DNA or luciferase (luminescence)-expressing plasmid DNA is adopted as a reporter gene, gene transfection efficiency of the cationic lipid analog materials was tested in Hela cells, and these materials were also effective. Therefore, it can be speculated that these cationic lipid analog materials can also be used as delivery carriers for nucleic acid drugs.

Finally, it should be noted that the above examples are provided merely to describe the technical solutions of the present application, rather than to limit the protection scope of the present application. Although the present application is described in detail with reference to preferred examples, a person of ordinary skill in the art should understand that modifications or equivalent replacements may be made to the technical solutions of the present application without departing from the spirit and scope of the technical solutions of the present application.

The invention claimed is:

1. A method of delivering nucleic acids into a cell, comprising utilization of a cationic lipid analog material, wherein the cationic lipid analog material is an ionizable cationic lipid analog material with a structure shown in formula (I):

I

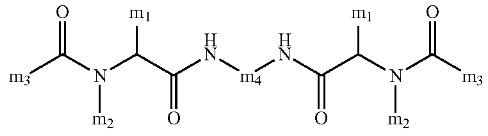

in formula (I), $m_1$ is independently selected from the group consisting of a linear alkyl, a branched alkyl, phenyl, or a heteroatom-containing aryl;

$m_2$ is

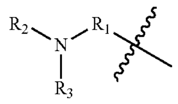, $R_1$ is an alkyl, $R_2$ is an alkyl, $R_3$ is an alkyl or phenyl, or $R_2$ and $R_3$ are connected as a cyclic group or a heterocyclic group;

$m_3$ is independently selected from the group consisting of a linear alkyl, a linear alkenyl, or

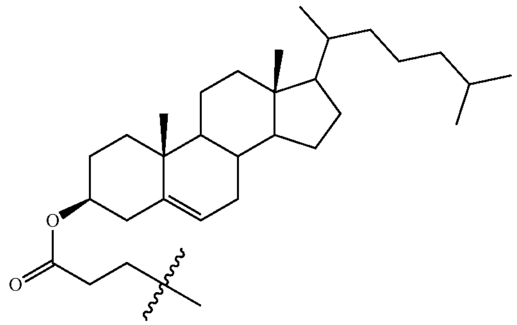;

and $m_4$ is independently selected from the group consisting of a linear alkyl, an ether bond-containing linear alkyl, or a N-heterocycle-containing alkyl.

2. The method according to claim 1, wherein $m_1$ is selected from the group consisting of an alkyl, phenyl, or a heteroatom-containing aryl substituted by a substituent α, and the substituent comprises methyl.

3. The method according to claim 2, wherein $m_1$ is selected from the group consisting of

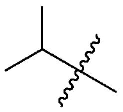,
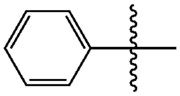, or

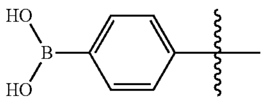.

4. The method according to claim 1, wherein $m_2$ is selected from the group consisting of

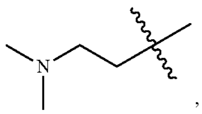,
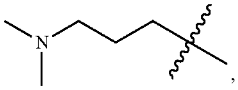,
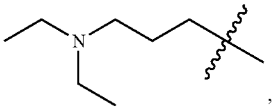,
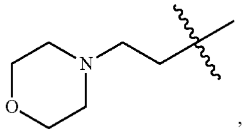,
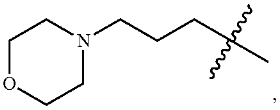,
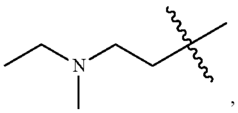,
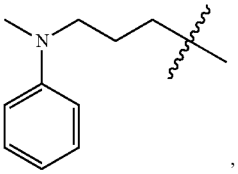,
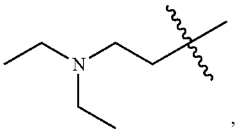,
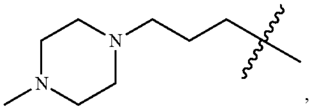,
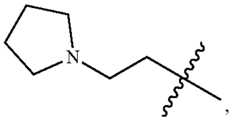, or

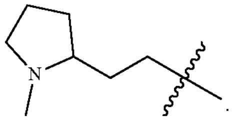.

5. The method according to claim 1, wherein $m_3$ is selected from the group consisting of a linear alkyl with 7 to 19 carbon atoms, a linear alkenyl with 17 carbon atoms, or

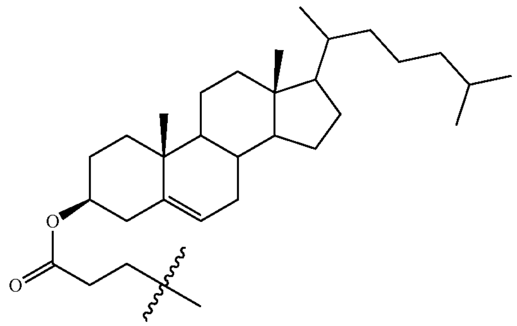.

6. The method according to claim 5, wherein $m_3$ is selected from the group consisting of

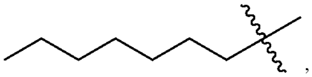,
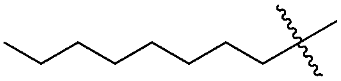,
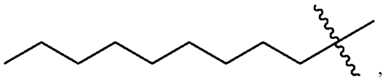,
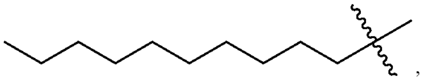,
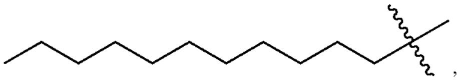,
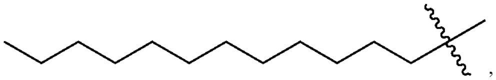,
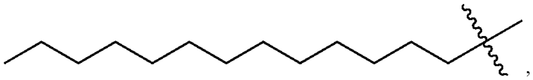,
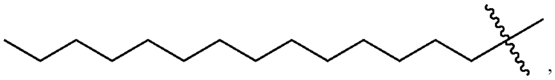,
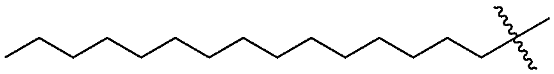,
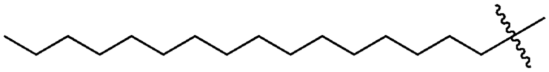,
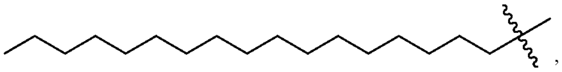,
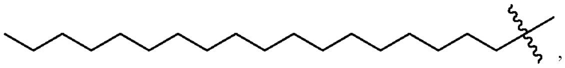,
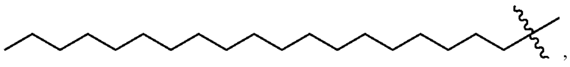,
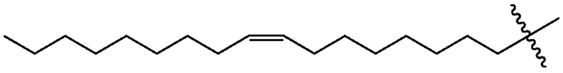,
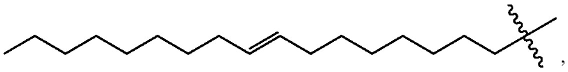,
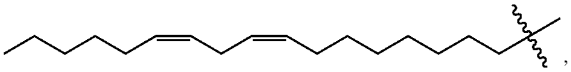, -continued

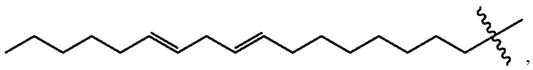

, or

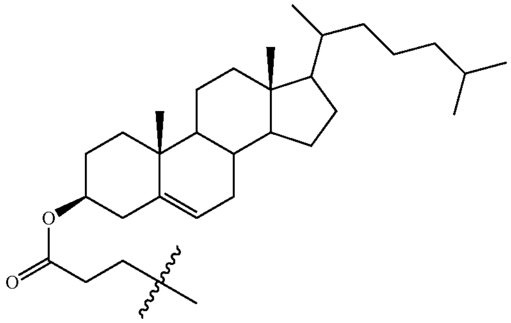

.

7. The method according to claim 1, wherein ma is selected from the group consisting of a linear alkyl with 6 carbon atoms, an ether bond-containing linear alkyl with 4 to 8 carbon atoms, or a N-heterocycle-containing alkyl.

8. The method according to claim 7, wherein ma is selected from the group consisting of

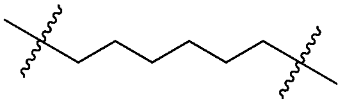

,

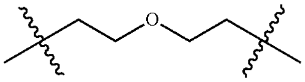

,

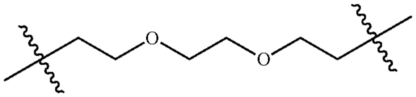

,

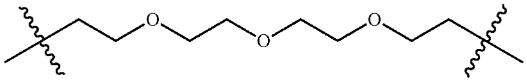

, or

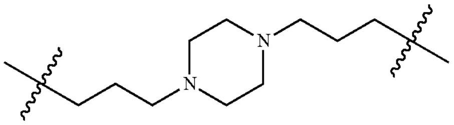

.

9. The method according to claim 1, wherein the ionizable cationic lipid analog material has a structure selected from the group consisting of the following 72 structures:

I1R1C12A1

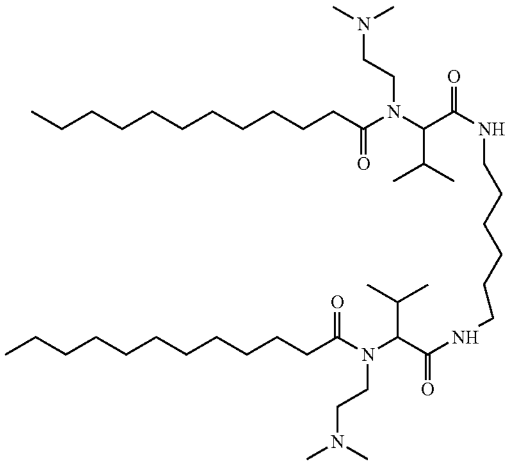

I1R1C14A1

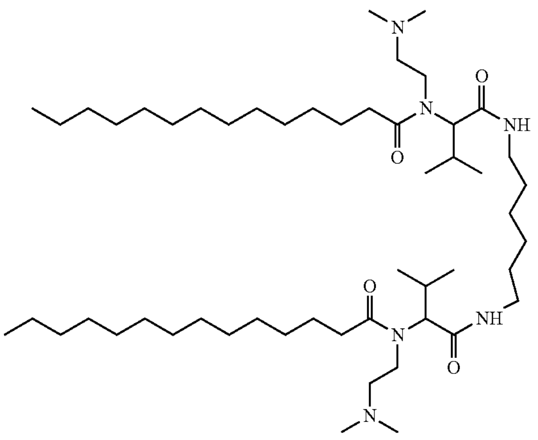

-continued
I1R1C16A1
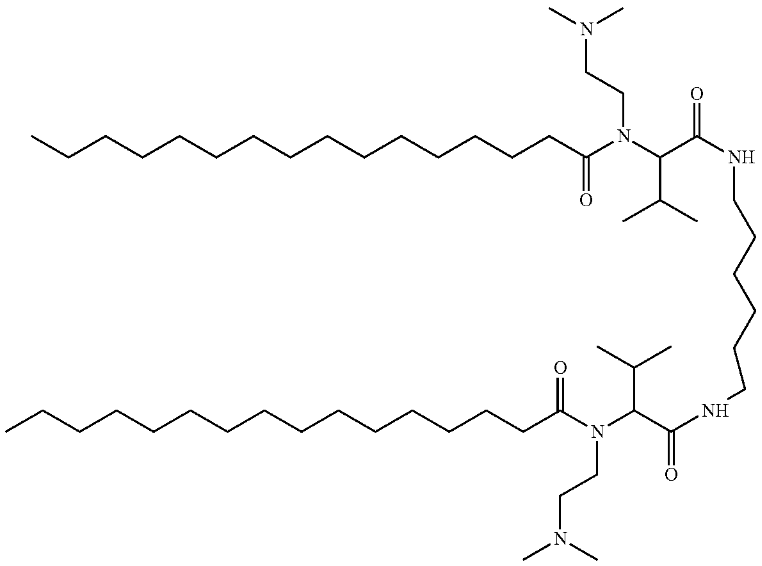
I1R1C18A1
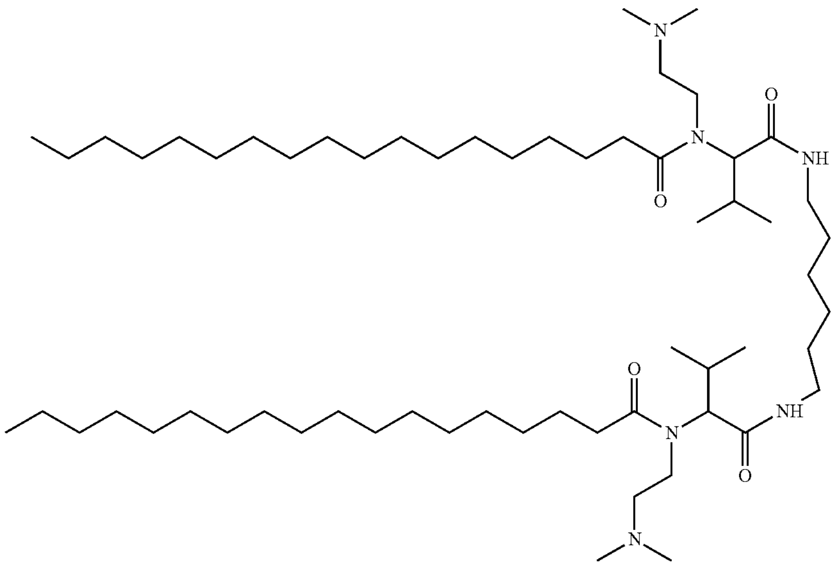

-continued
I1R1C20A1
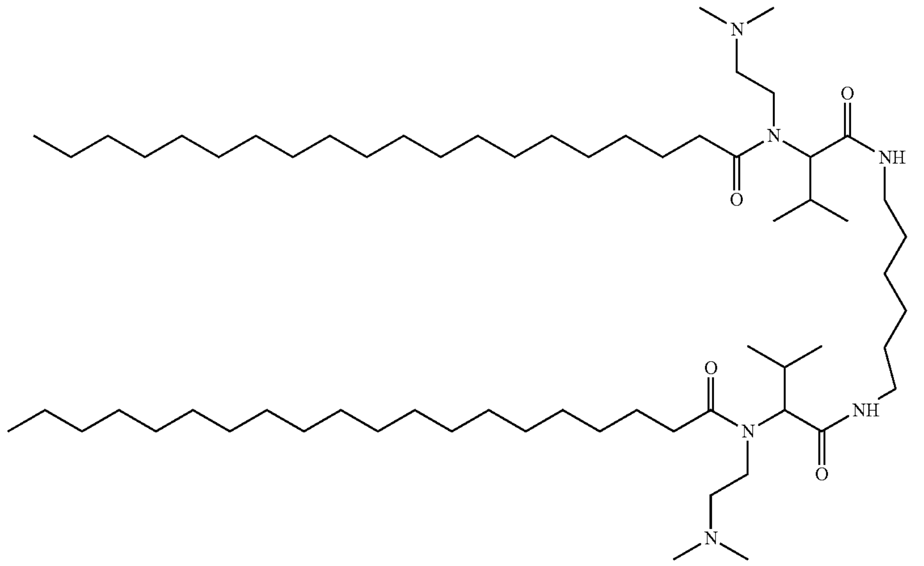
I1R1C18-1A1
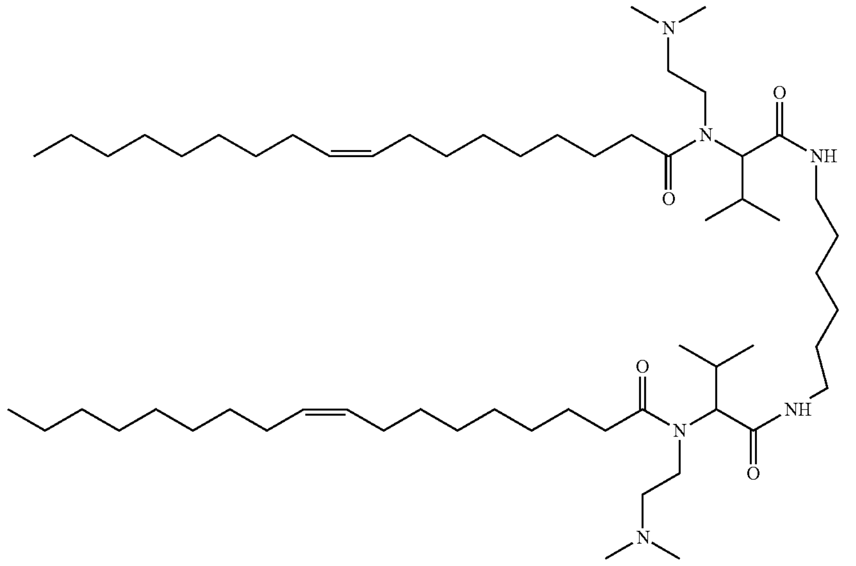
I1R3C14A1
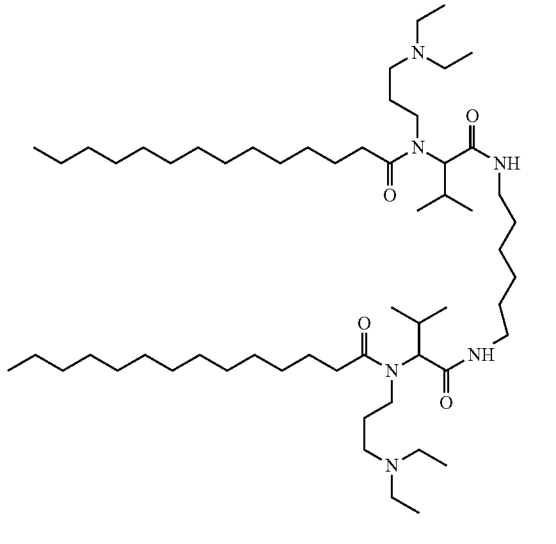

-continued
I1R1C18-2A1
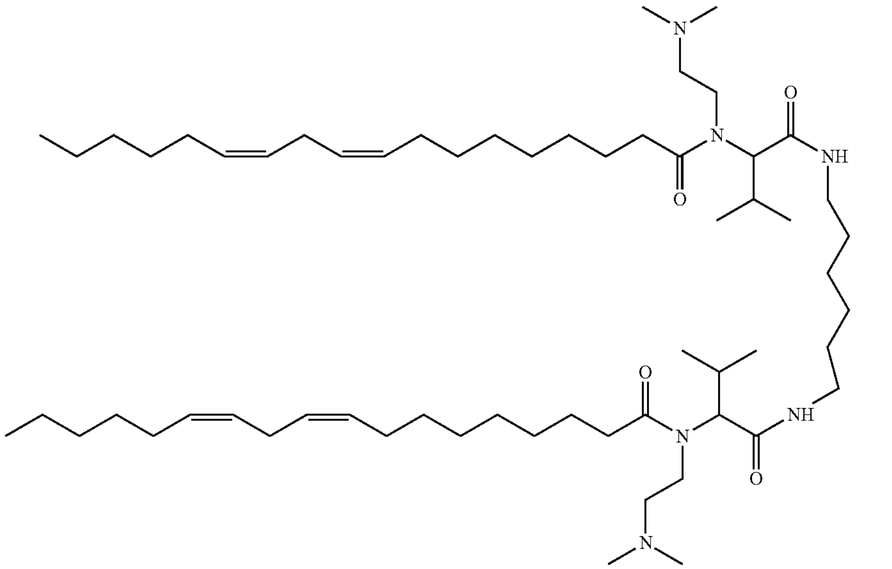
I1R2C12A1
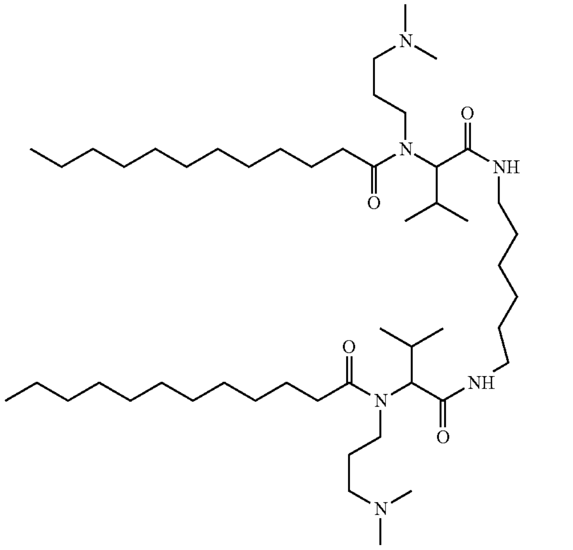
I1R2C14A1
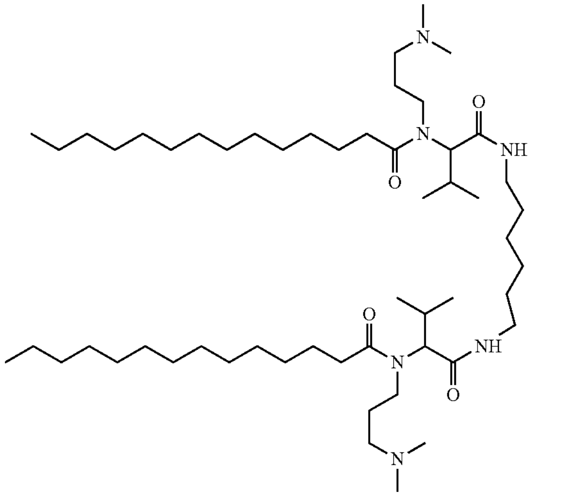

-continued
I1R2C16A1
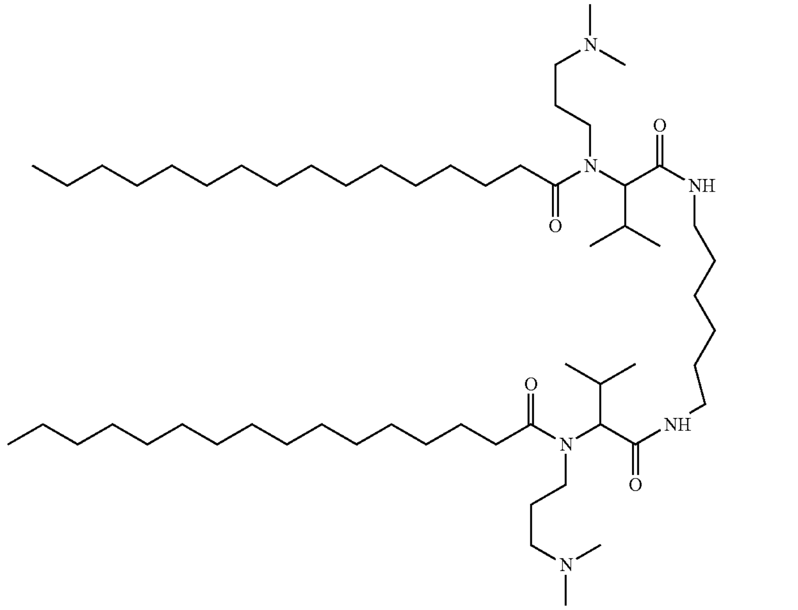
I1R2C18A1
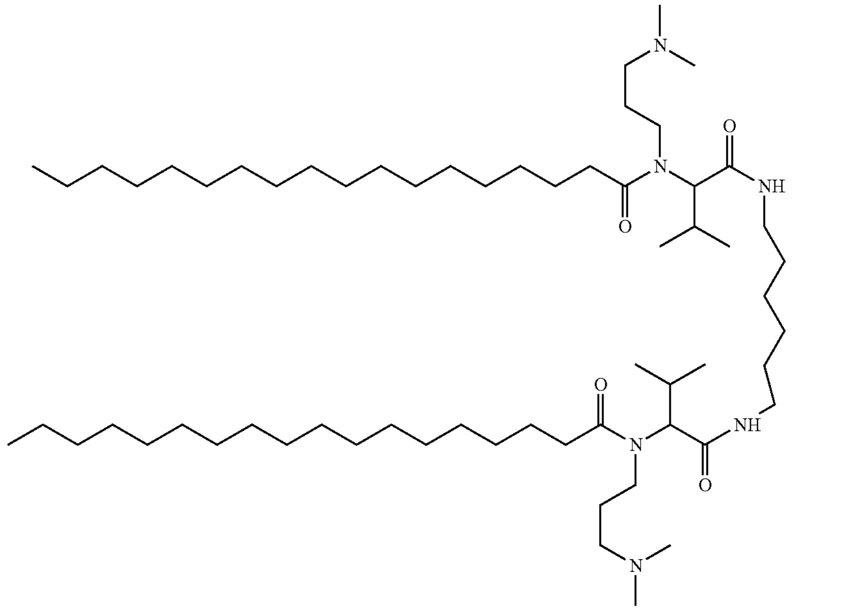

-continued
I1R2C20A1
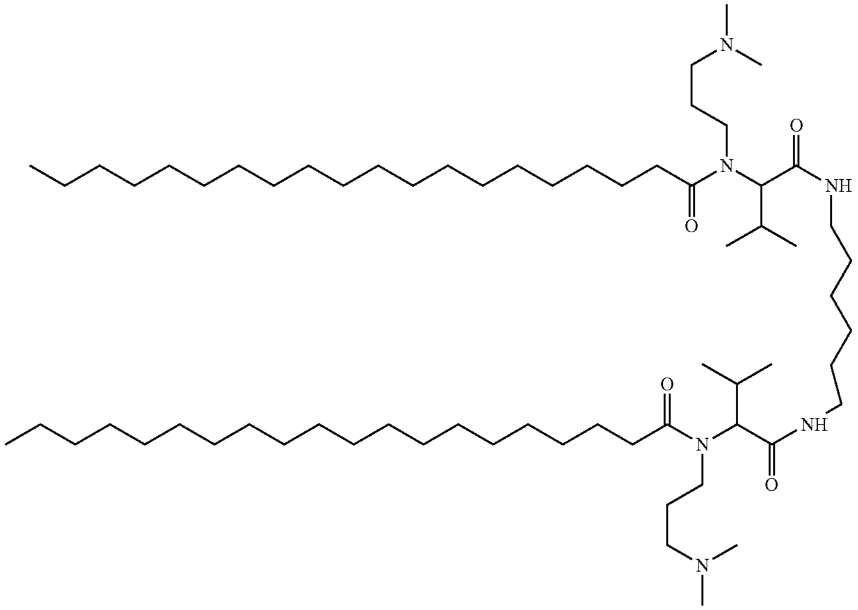
I1R2C18-1A1
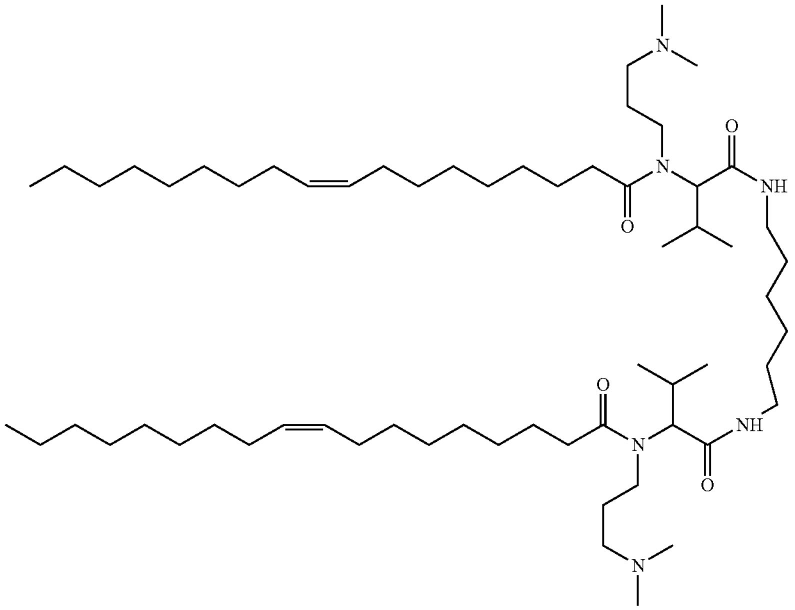

-continued
I1R2C18-2A1
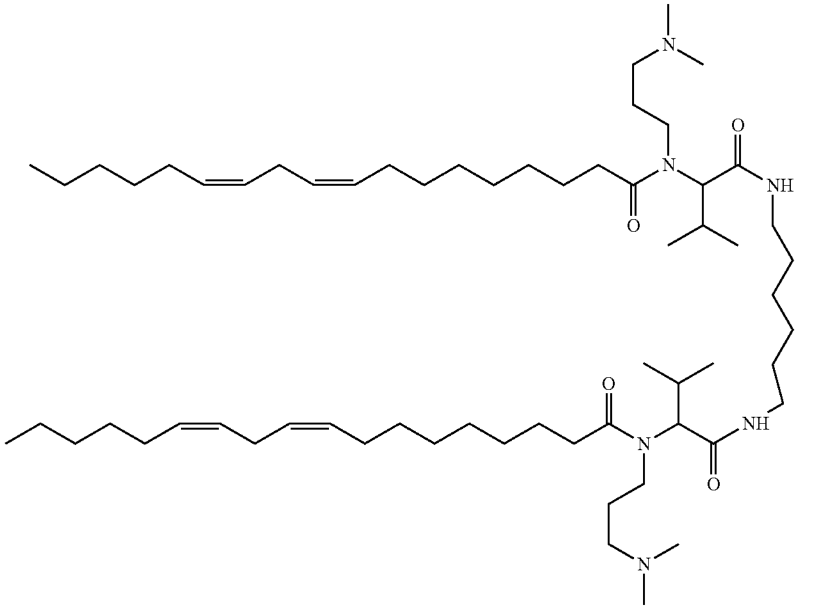
I1R3C12A1
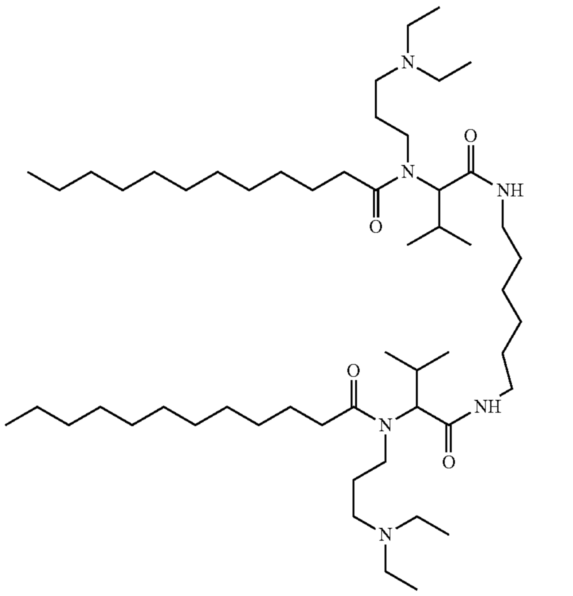
I1R3C16A1
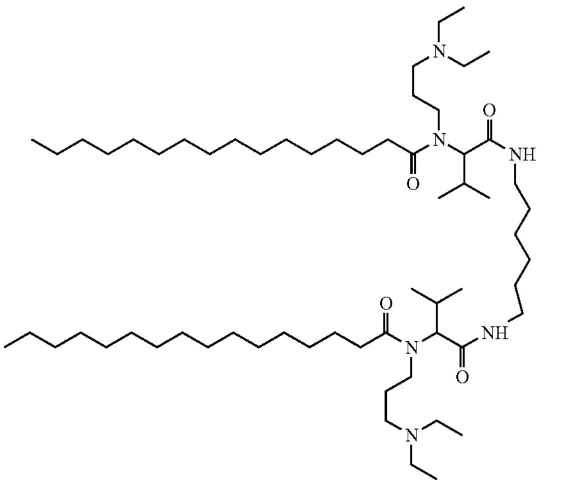

-continued
I1R3C18A1
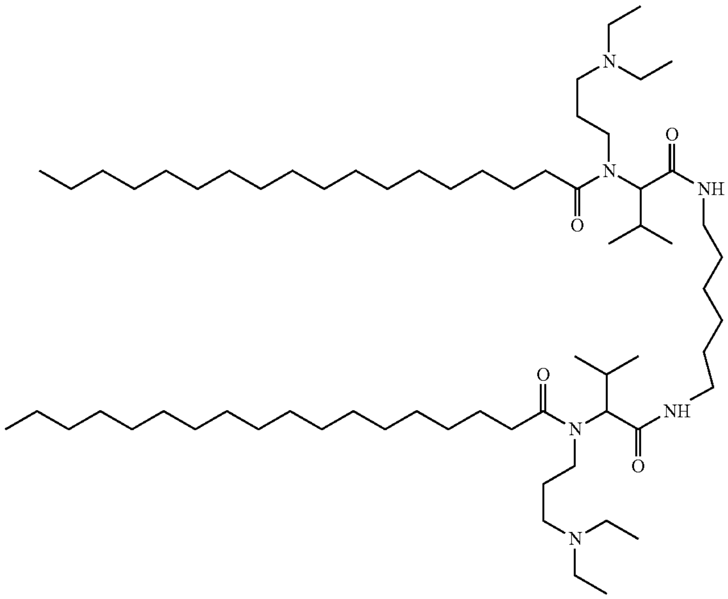
I1R3C20A1
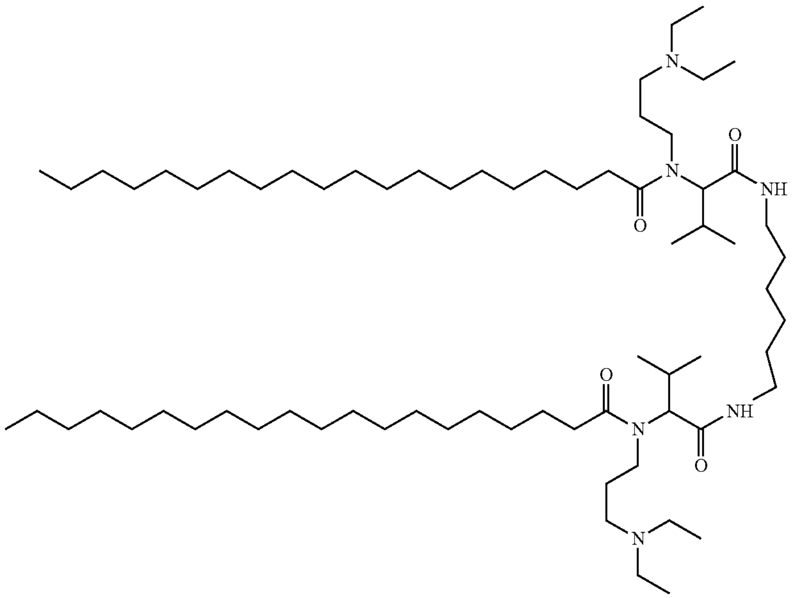

-continued
I1R3C18-1A1
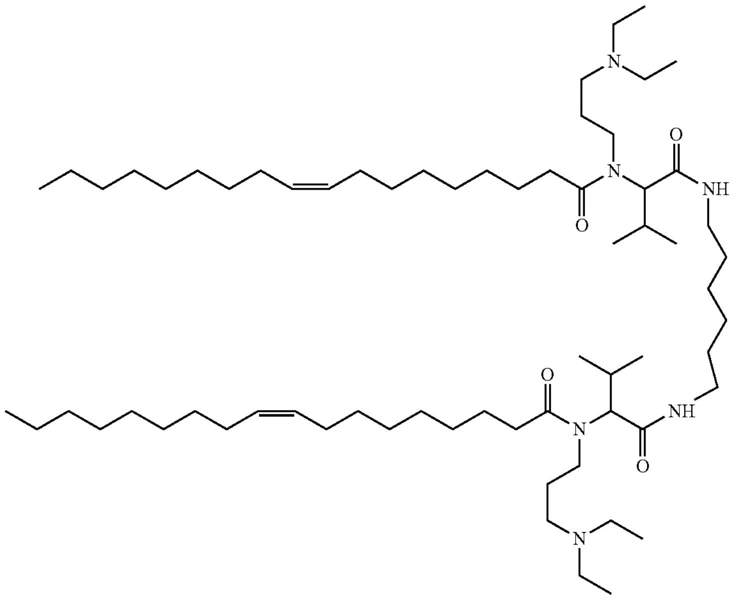
I1R3C18-2A1
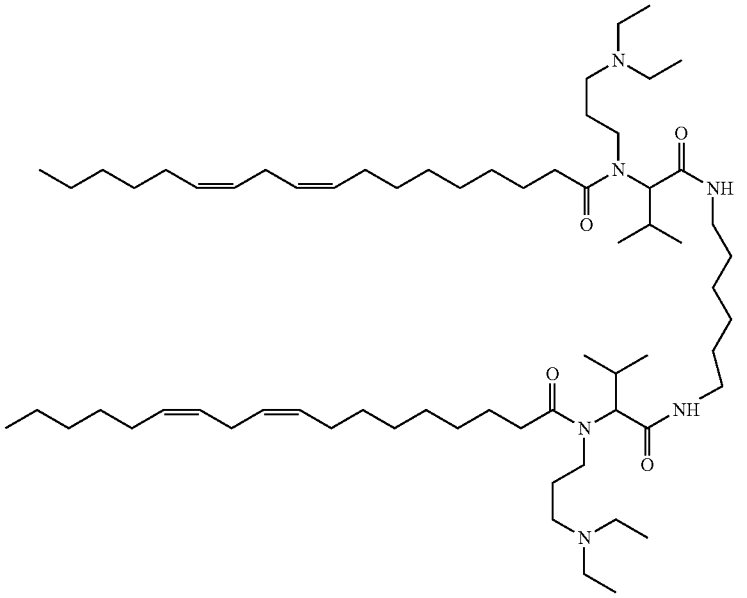

-continued
I1R5C12A1
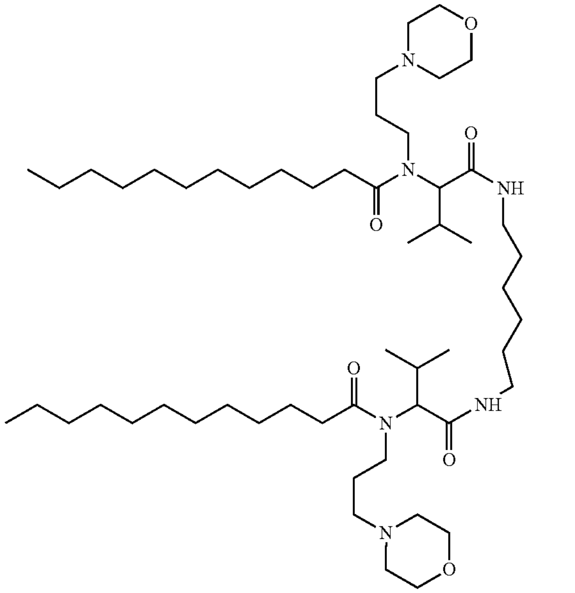
I1R5C14A1
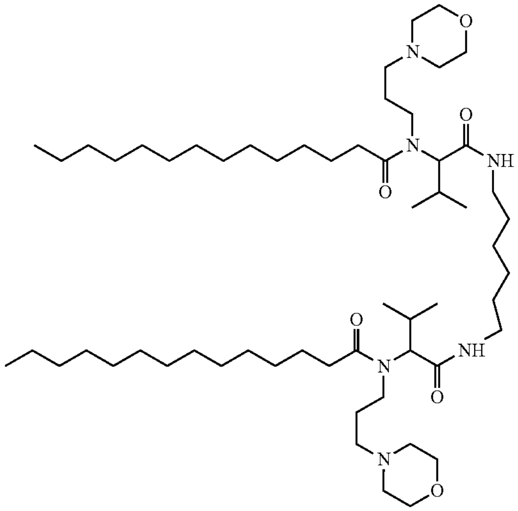
I1R5C16A1
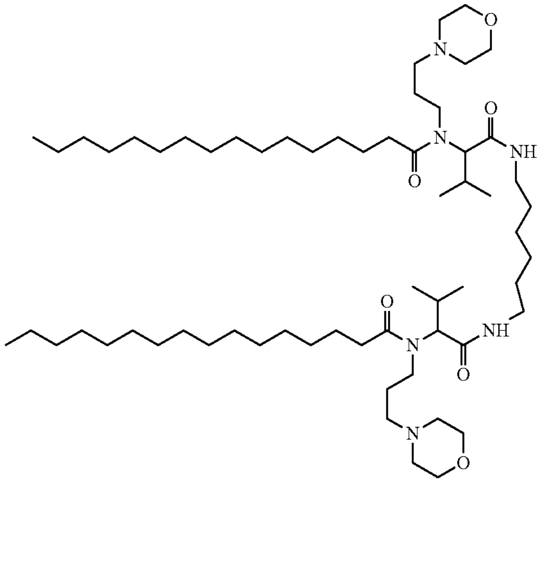

-continued
I1R5C18A1
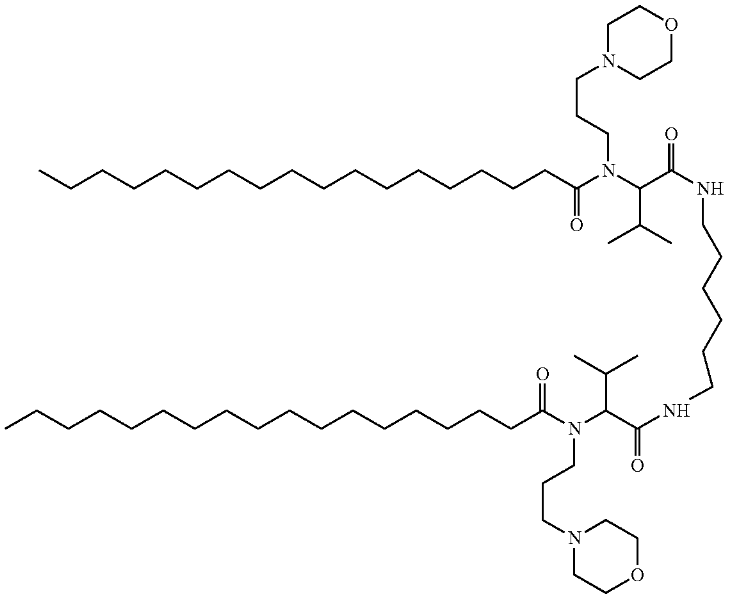
I1R5C20A1
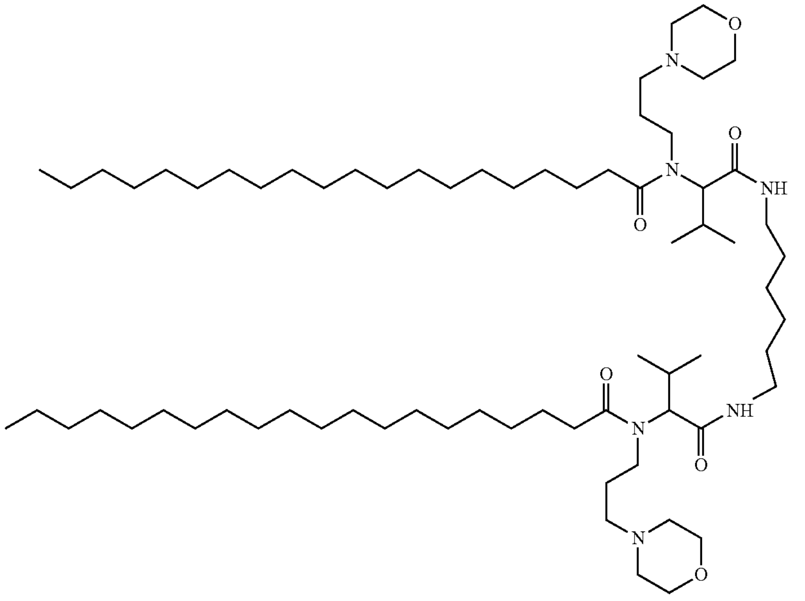

-continued
I1R5C18-1A1
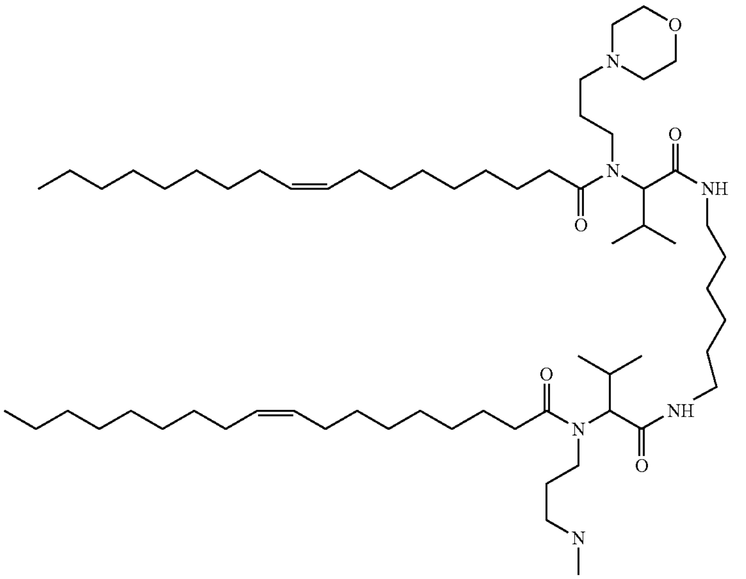
I1R5C18-2A1
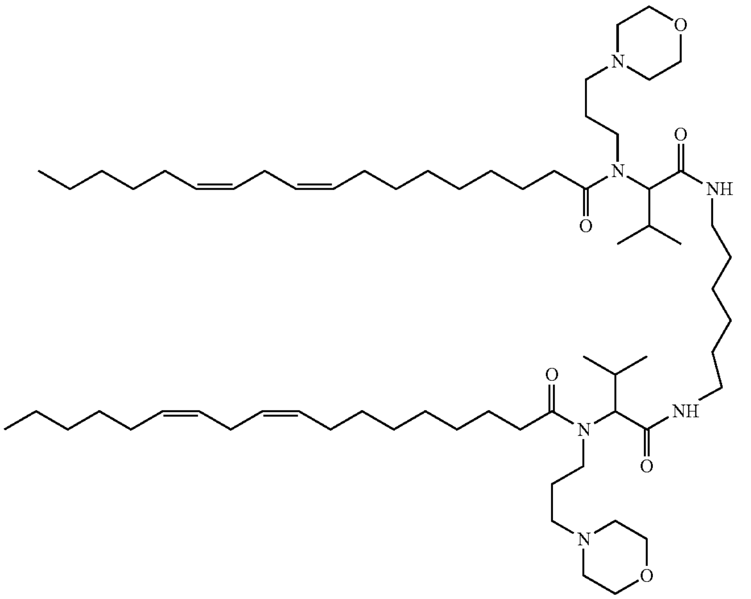

-continued
I1R11C12A1
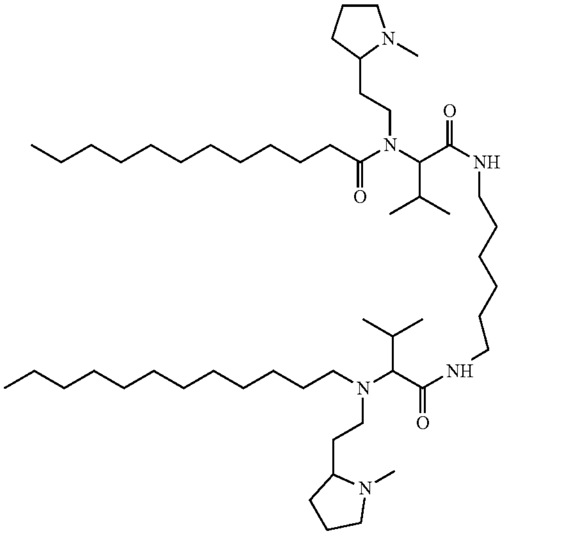
I1R11C14A1
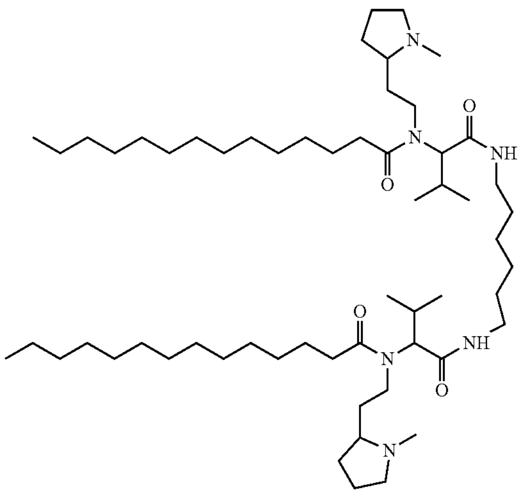
I1R11C16A1
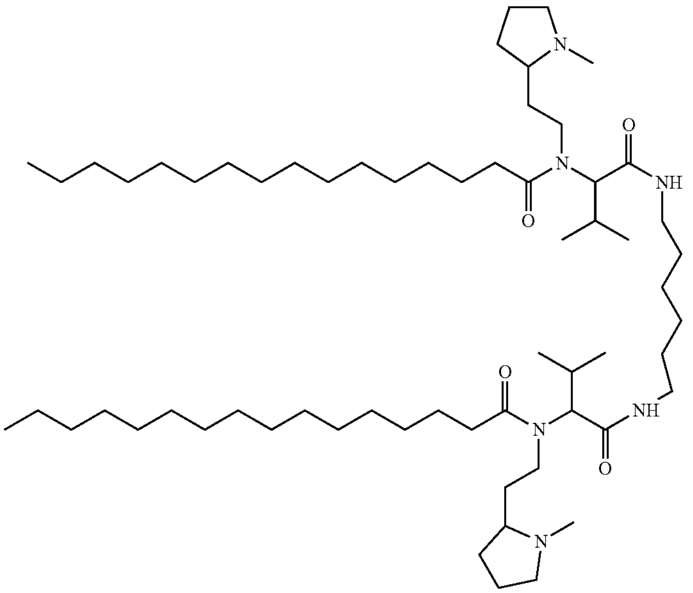

-continued
I1R11C18A1
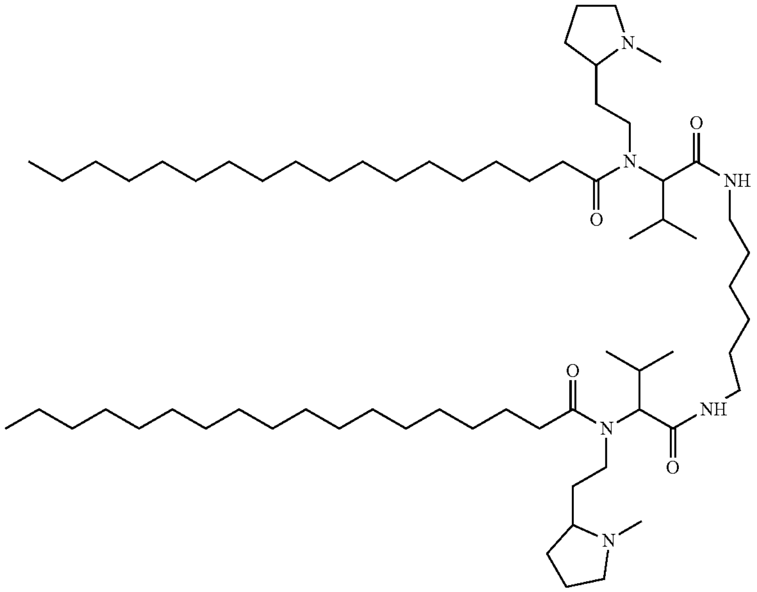
I1R11C20A1
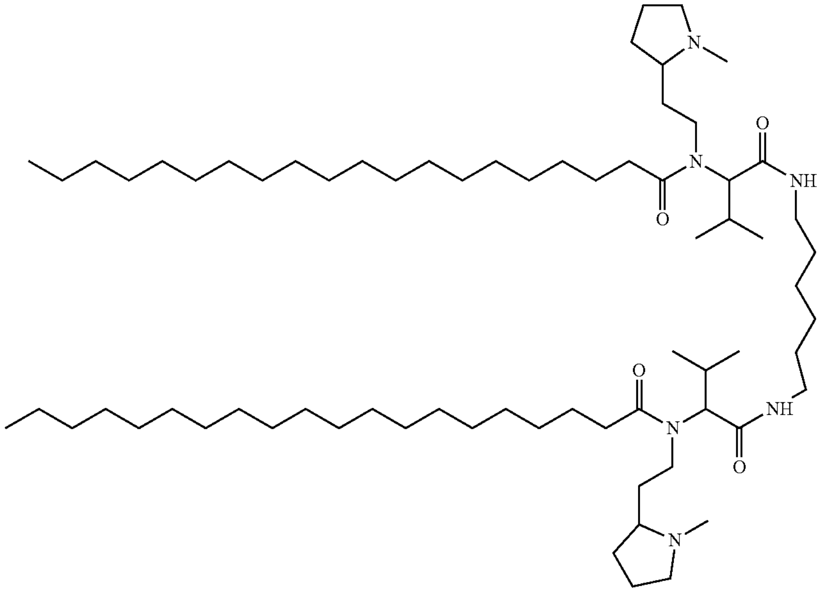

-continued
I1R11C18-1A1
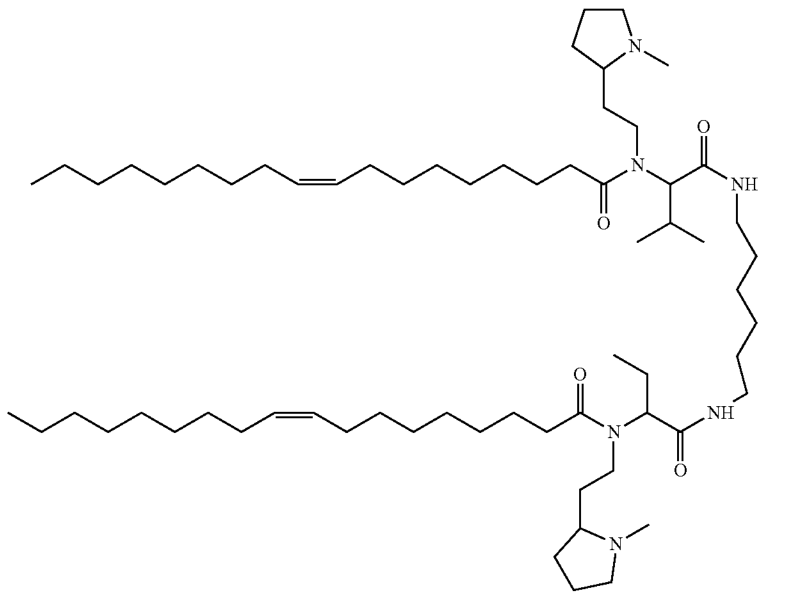
I1R11C18-2A1
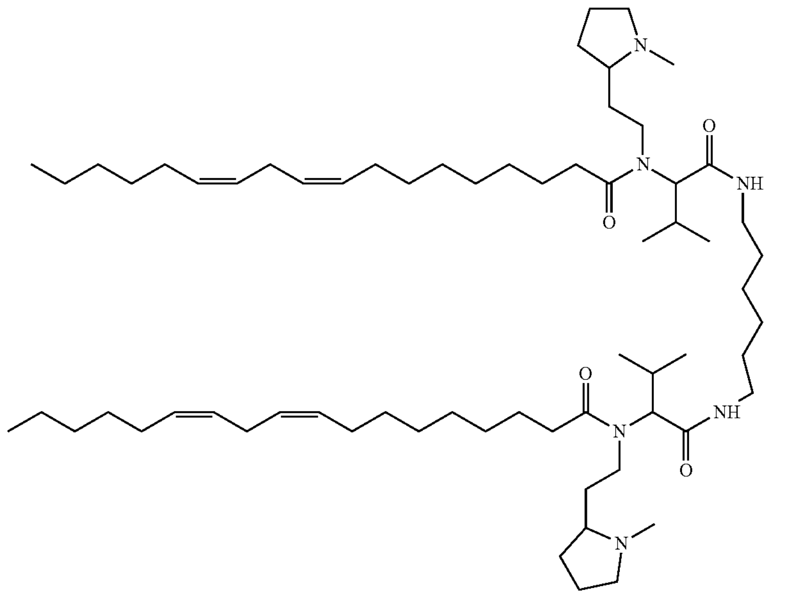

-continued
I2R1C12A1
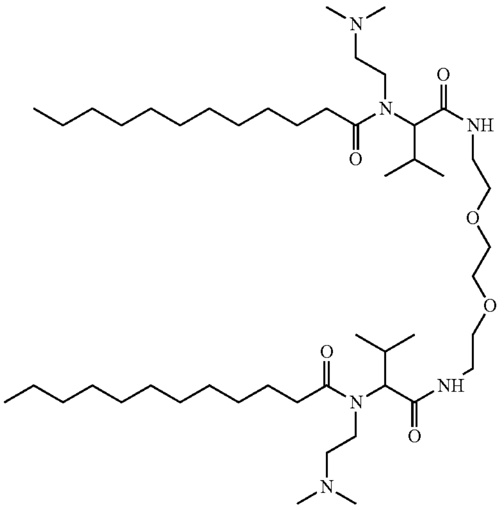
I2R1C14A1
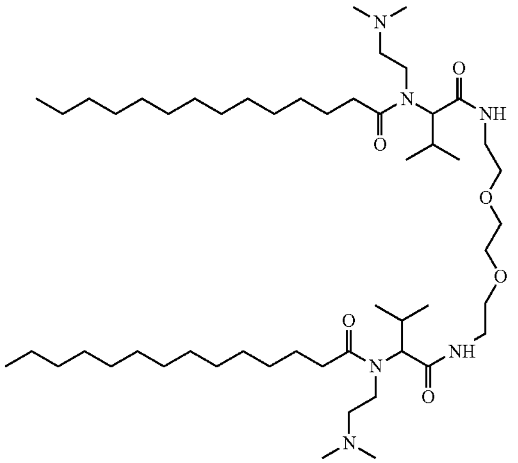
I2R1C16A1
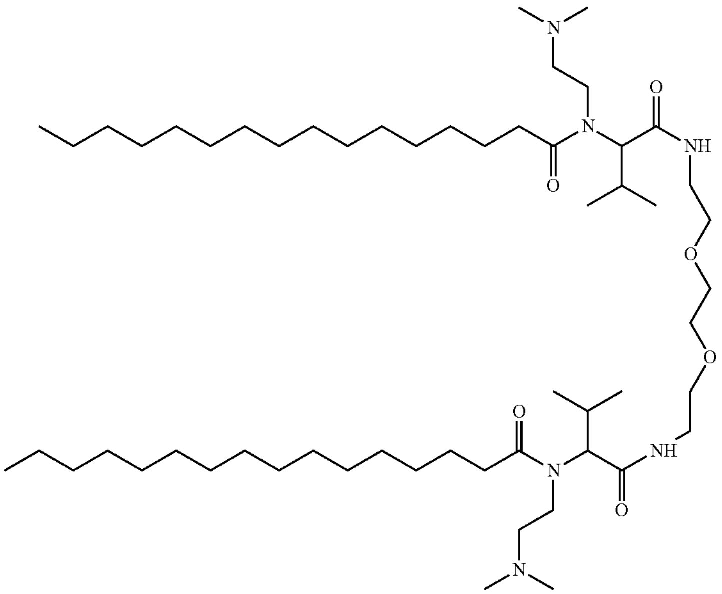

-continued
I2R1C18A1
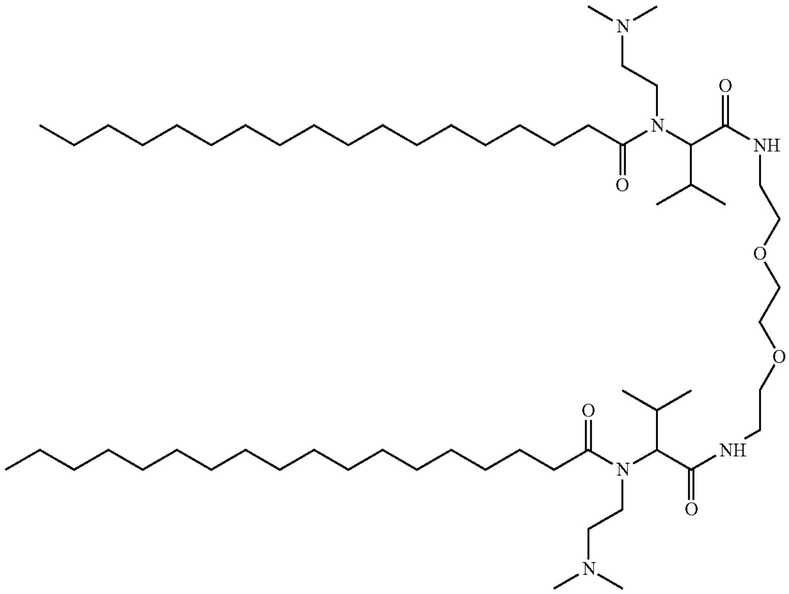
I2R1C20A1
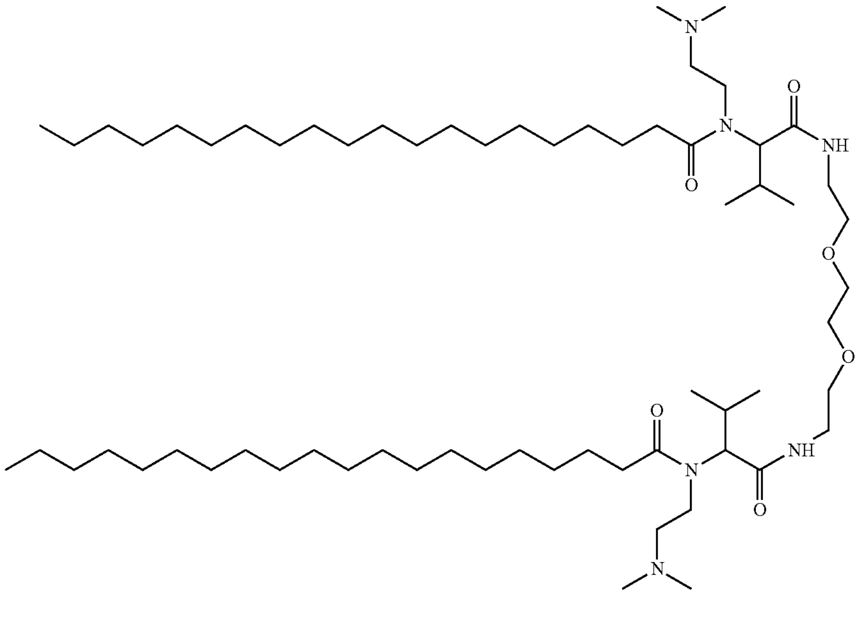

-continued
I2R1C18-1A1
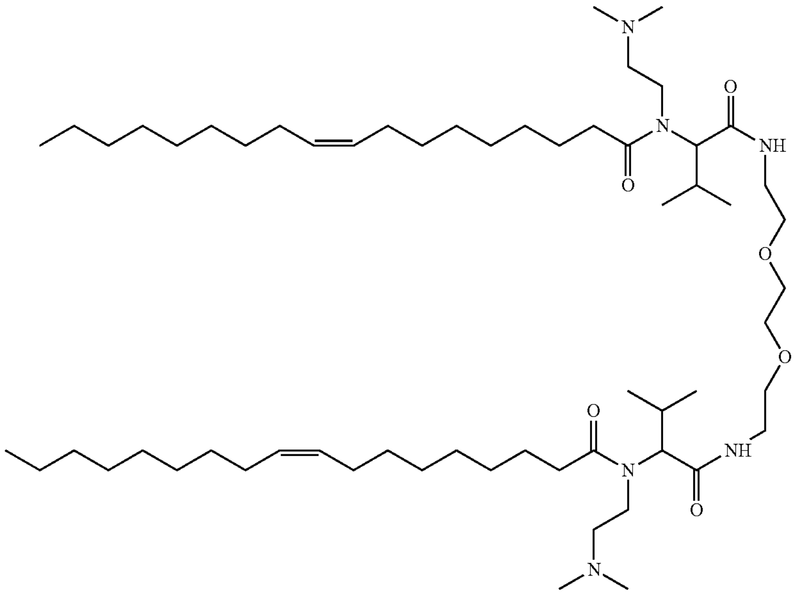
I2R1C18-2A1
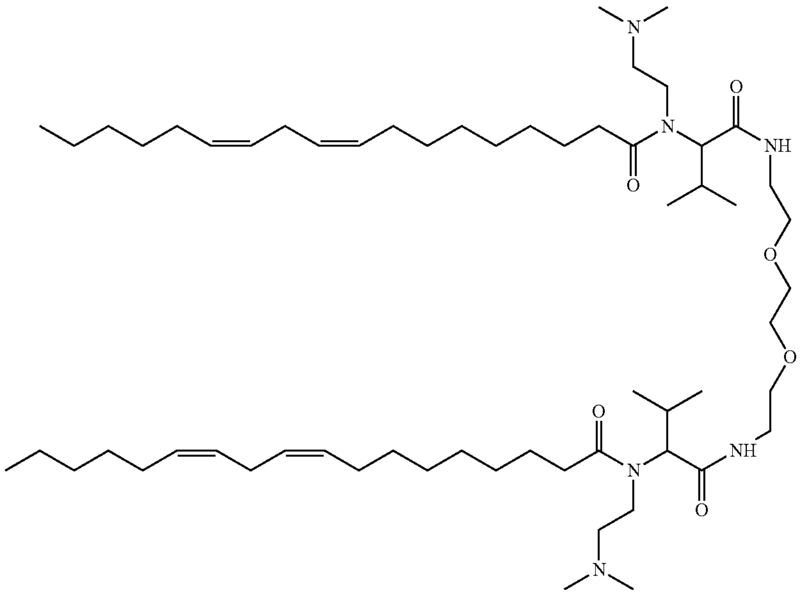

-continued
I2R2C12A1
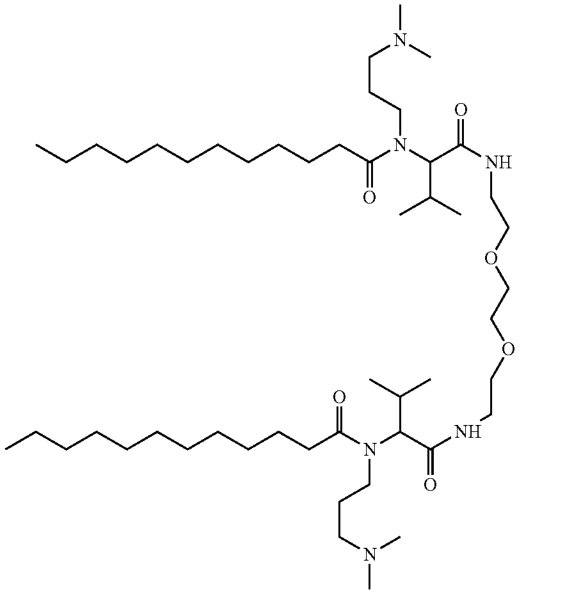
I2R2C14A1
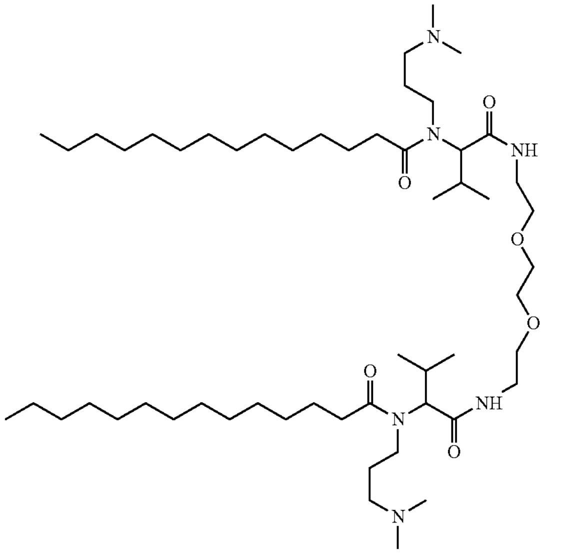
I2R2C16A1
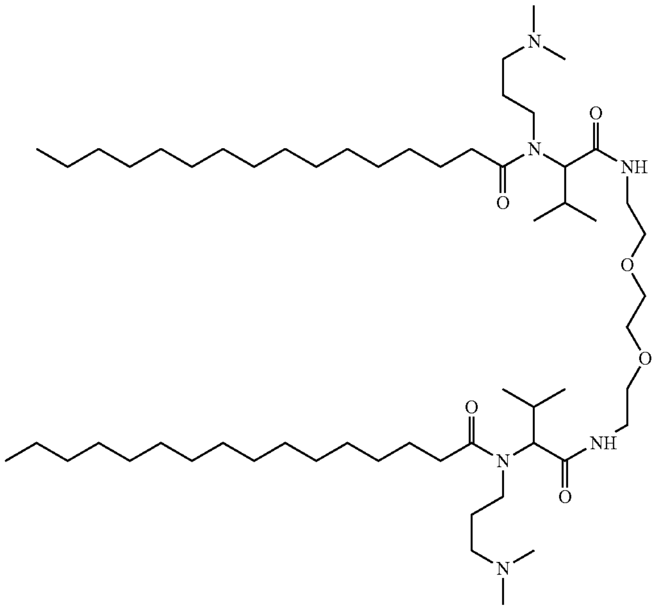

-continued
I2R2C18A1
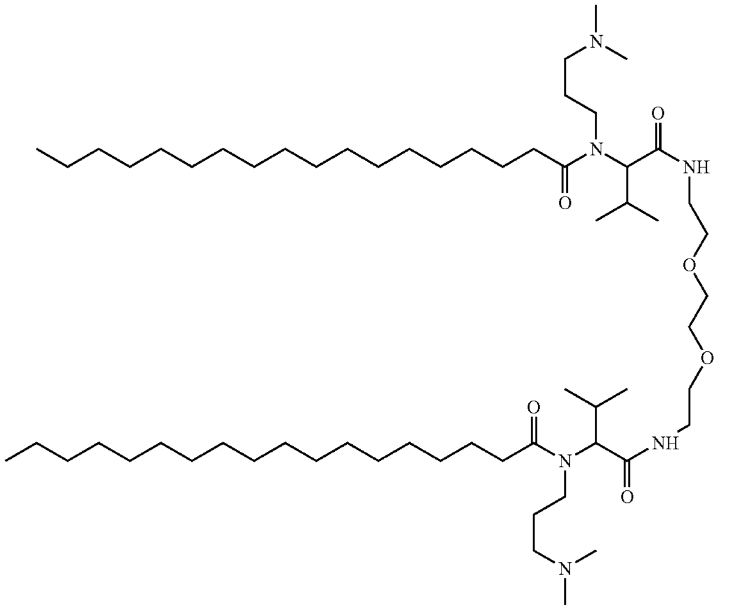
I2R2C20A1
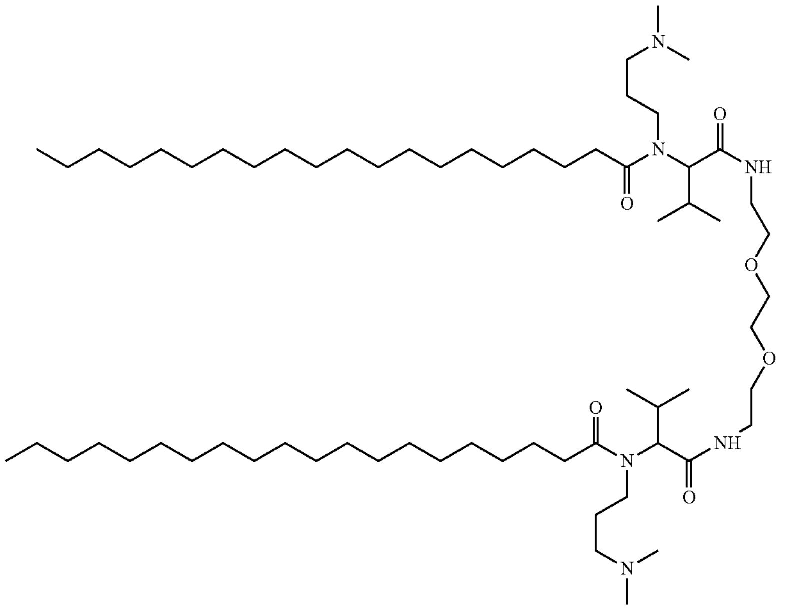

-continued
I2R2C18-1A1
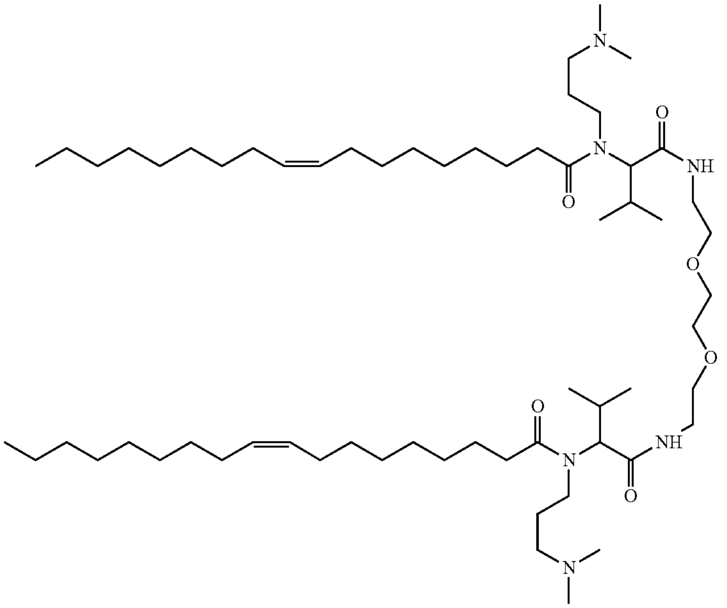
I2R2C18-2A1
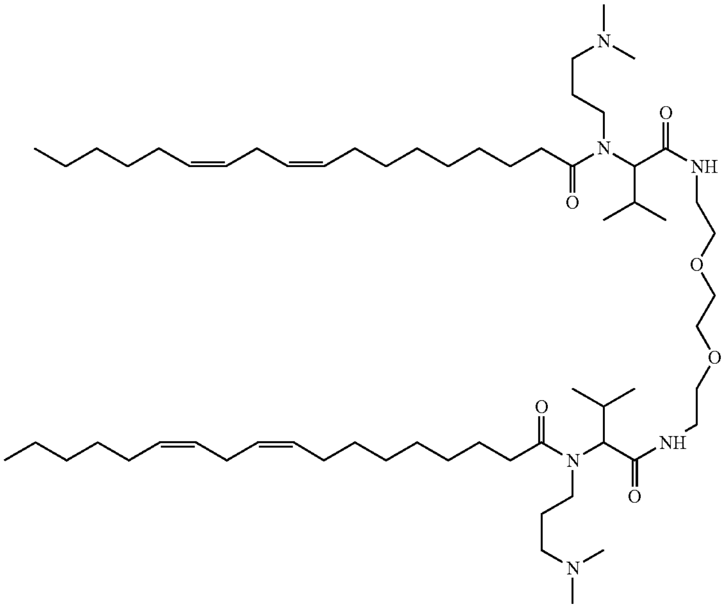

-continued
I2R3C12A1
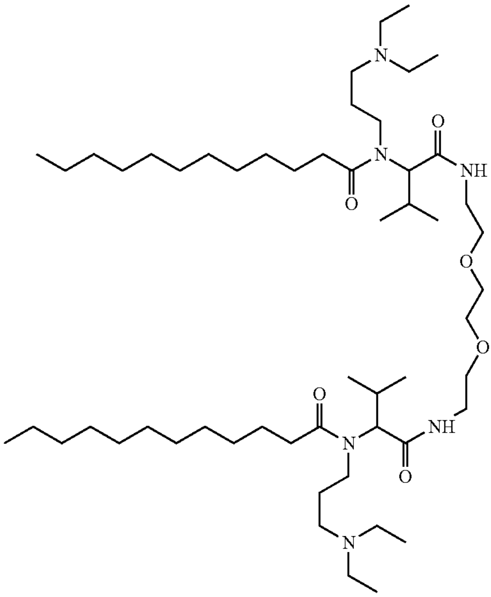
I2R3C14A1
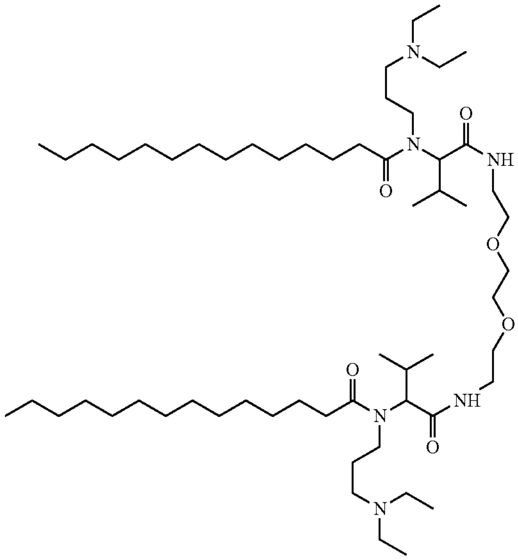
I2R3C16A1
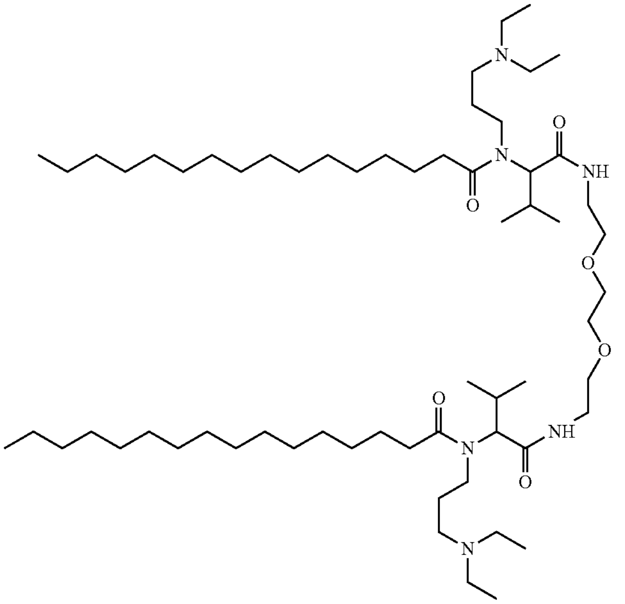

-continued
I2R3C18A1
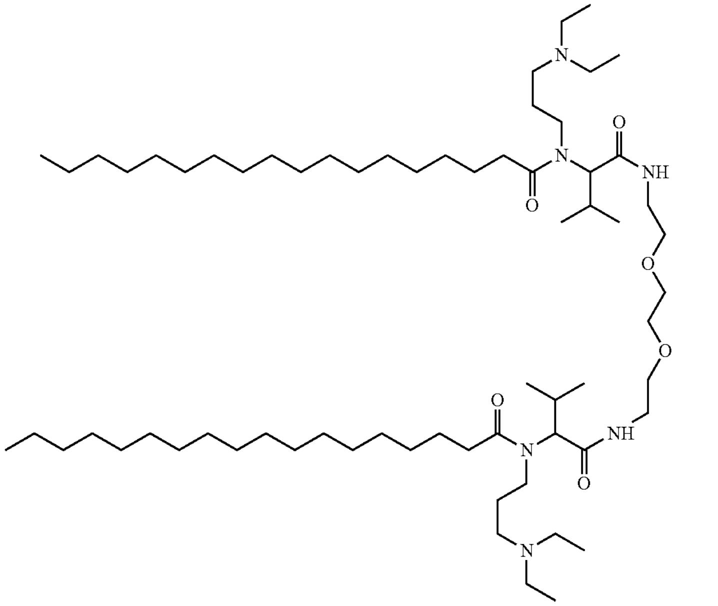
I2R3C20A1
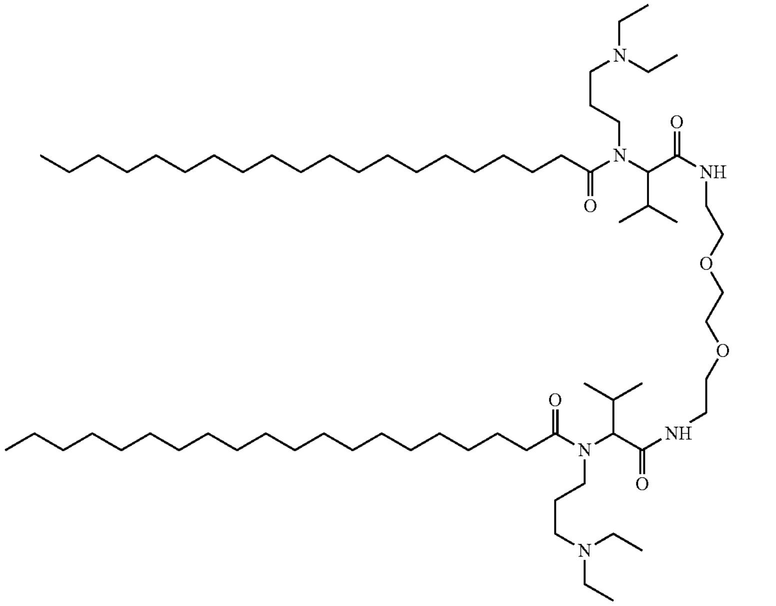

-continued
I2R3C18-1A1
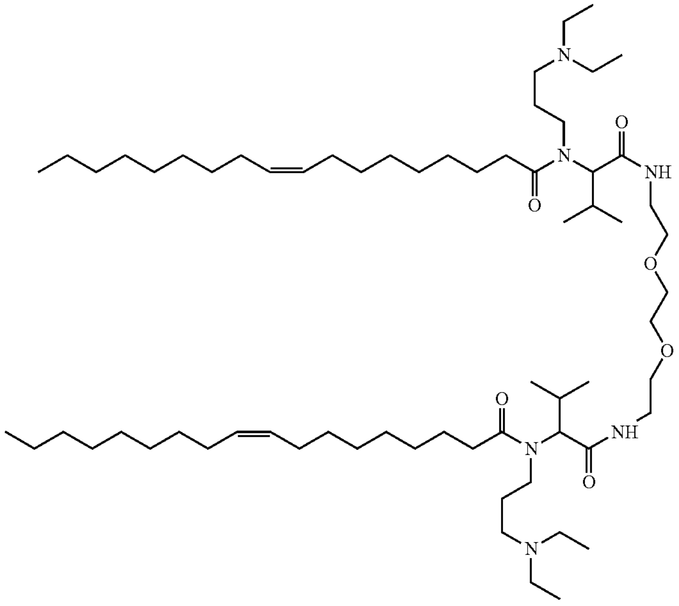
I2R3C18-2A1
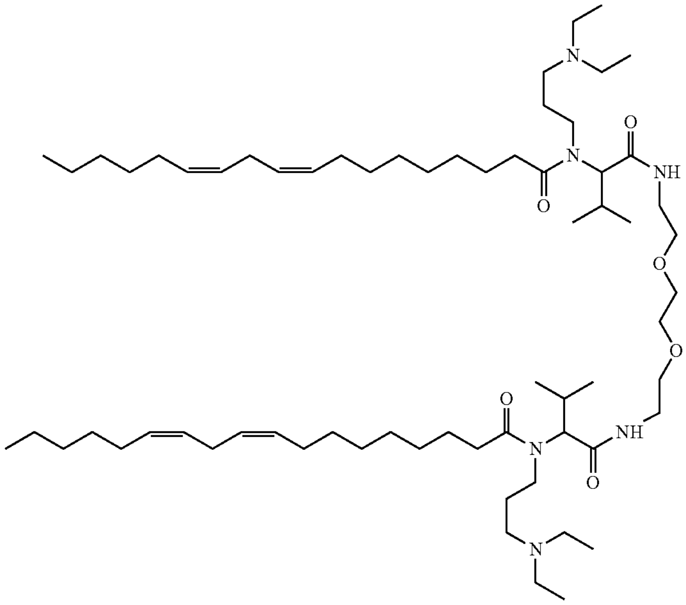

-continued
I2R5C12A1
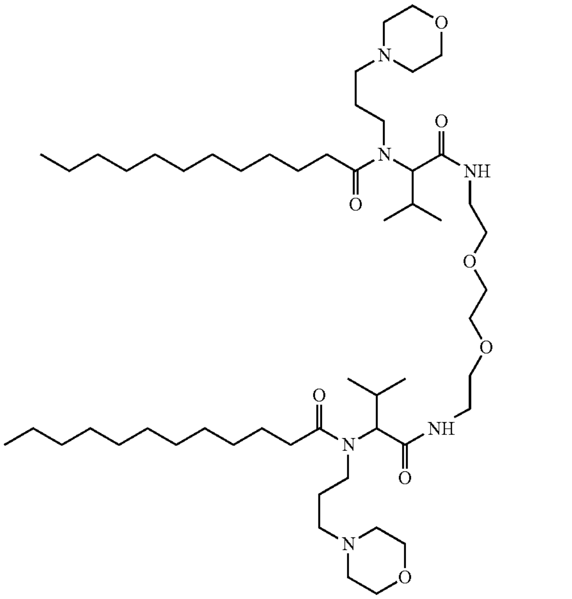
I2R5C14A1
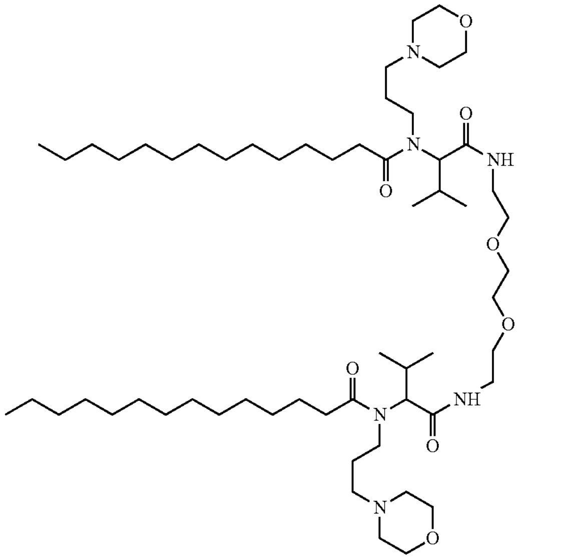
I2R5C16A1
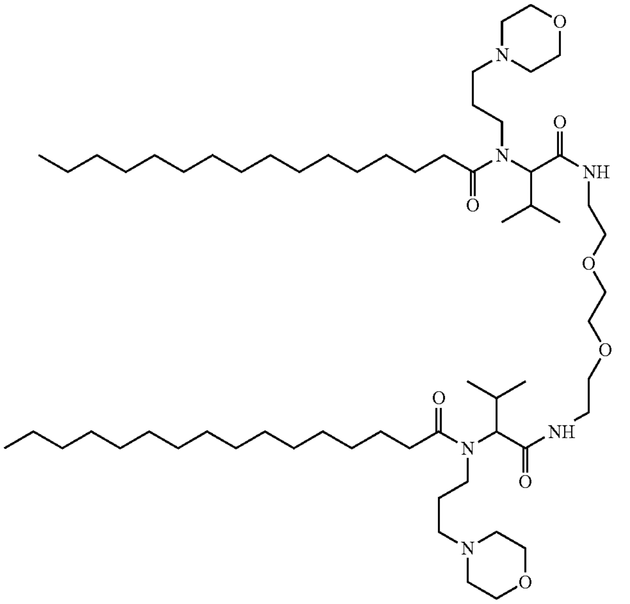

-continued
I2R5C18A1
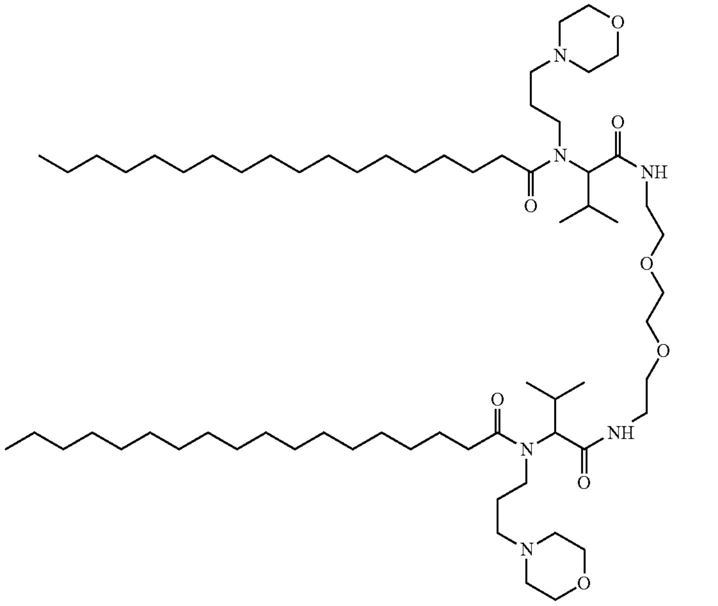
I2R5C20A1
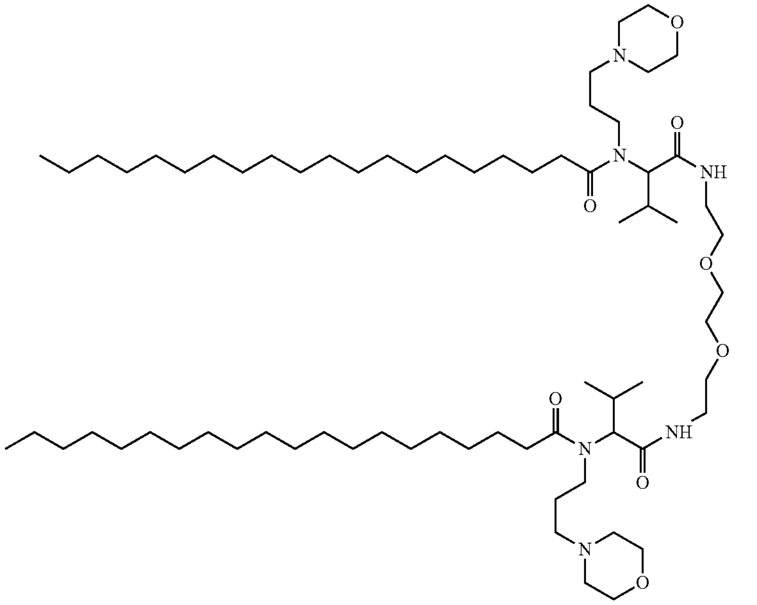

-continued
I2R5C18-1A1
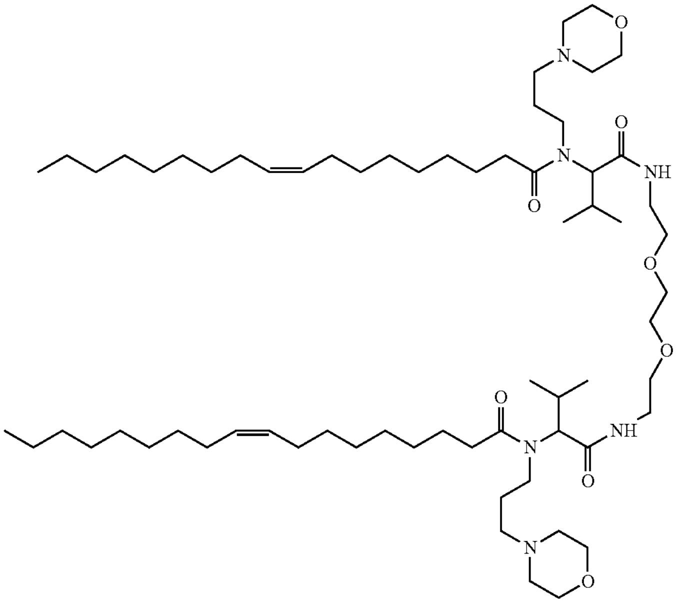
I2R5C18-2A1
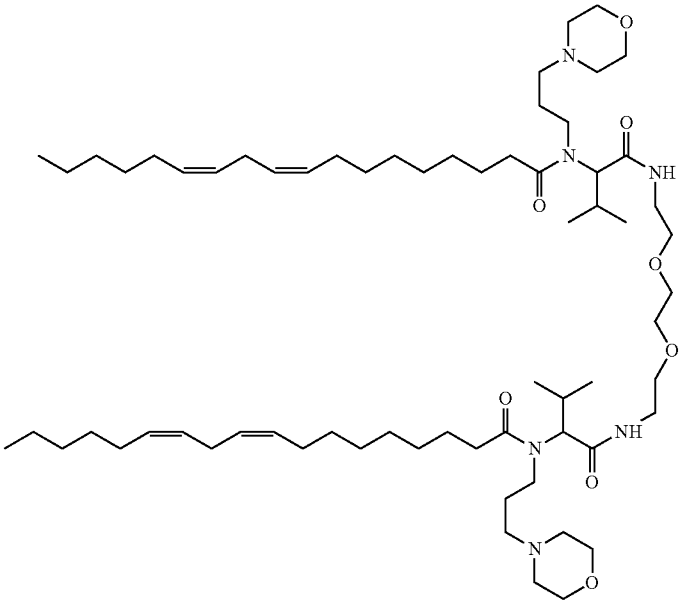

-continued
I2R11C12A1
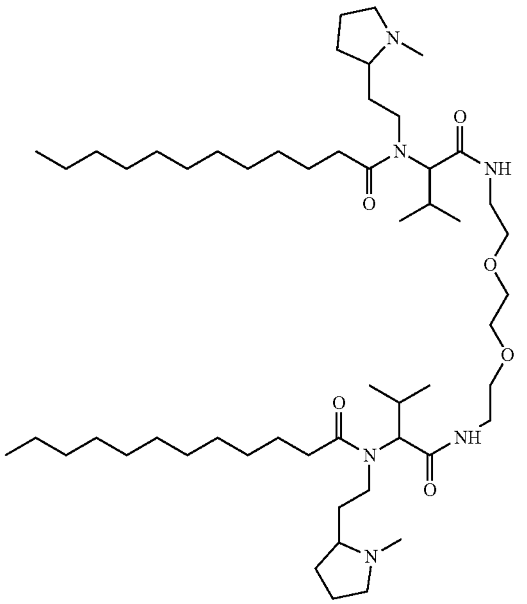
I2R11C14A1
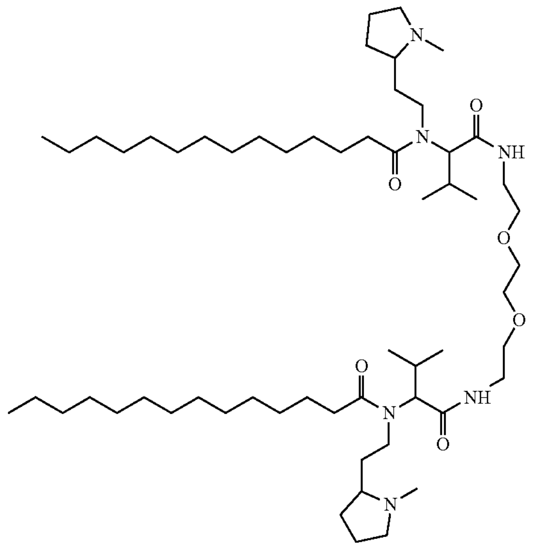
I2R11C16A1
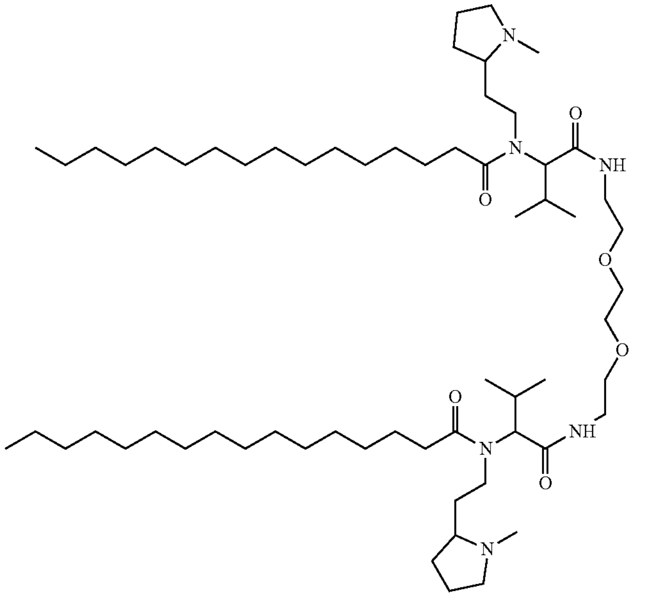

-continued
I2R11C18A1
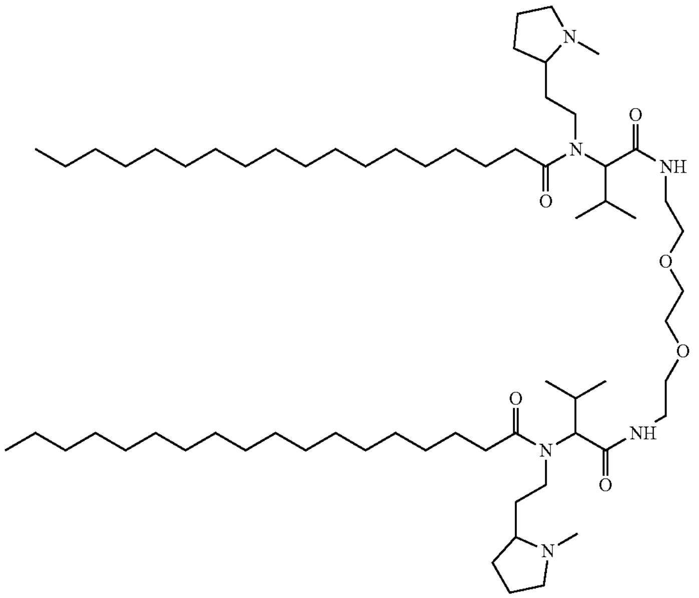
I2R11C20A1
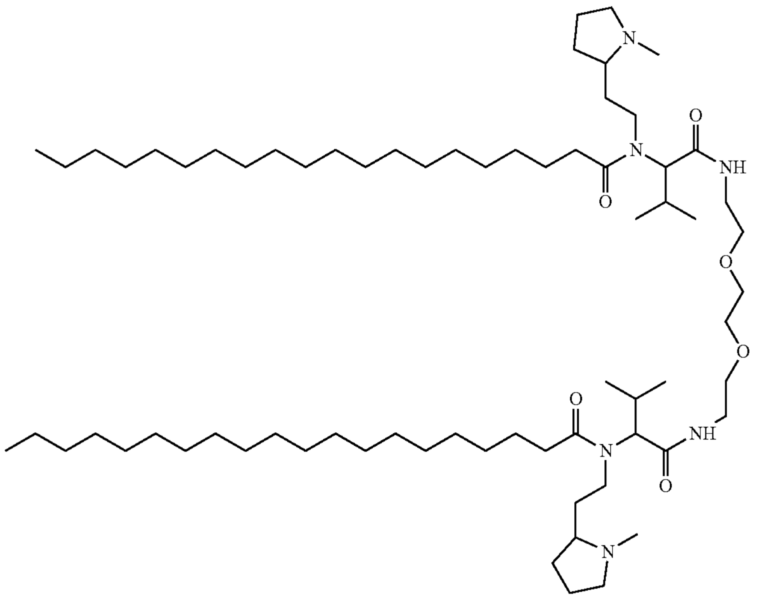

-continued
I2R11C18-1A1
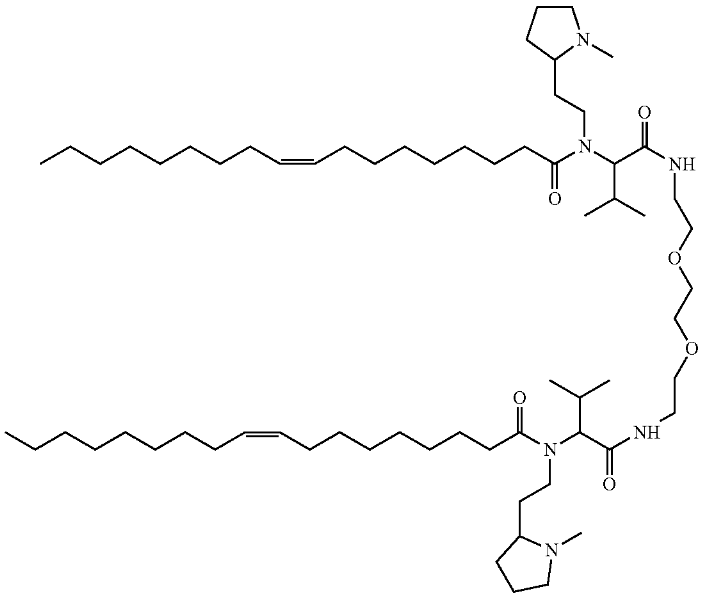
I2R11C18-2A1
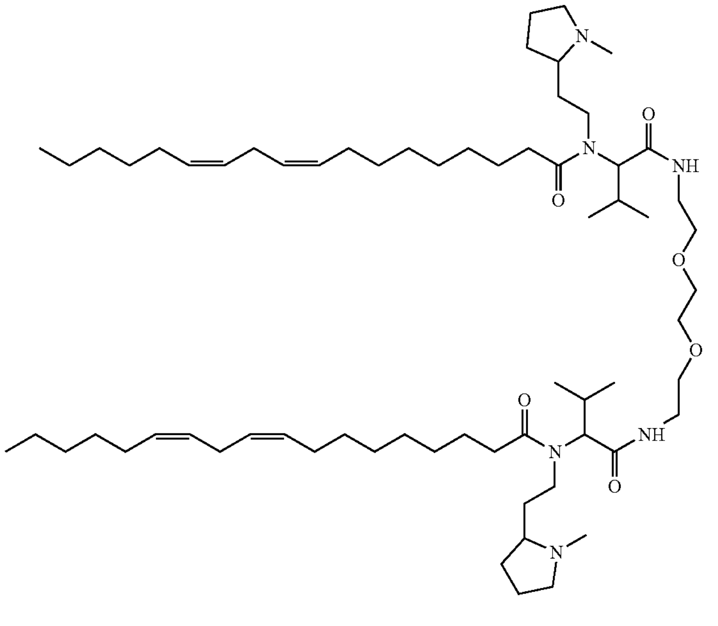

-continued

I2-1R2C18A1

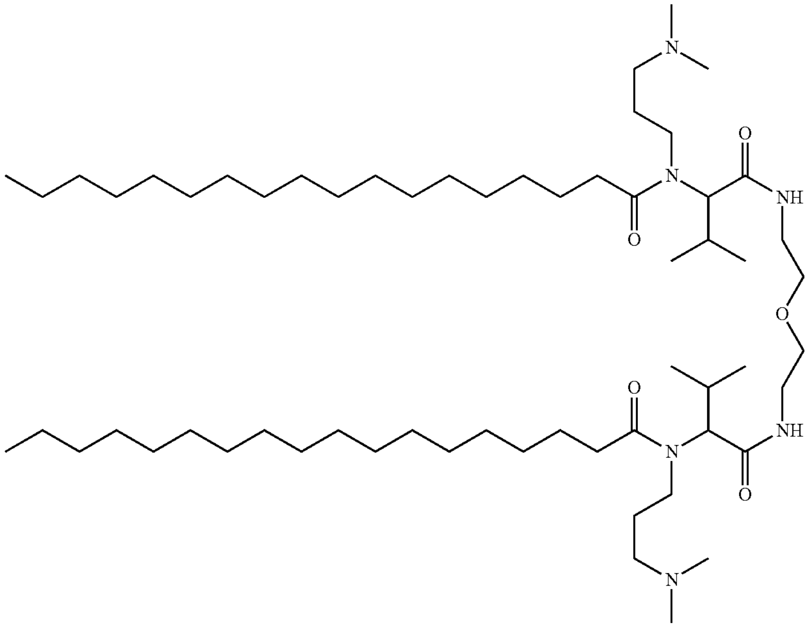

I2-3R2C18A1

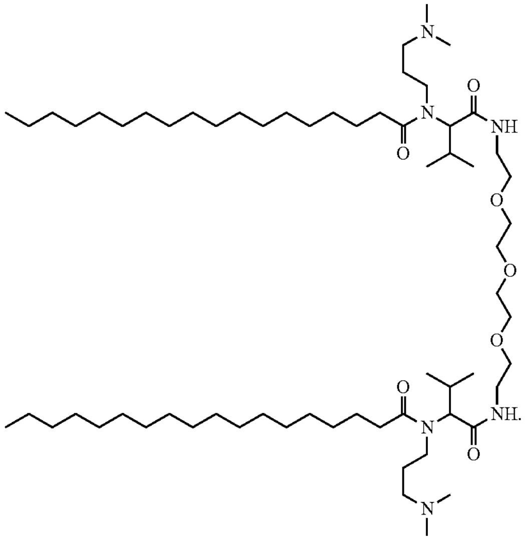

10. The method according to claim 9, wherein the cationic lipid analog material is at least one selected from the group consisting of I1R2C14A1, I1R2C18-2A1, I1R11C14A1, I2R1C14A1, I2R1C16A1, I2R1C18-1A1, I2R1C18-2A1, I2R2C14A1, I2R2C16A1, I2R2C18-1A1, I2R2C18-2A1, I2R3C16A1, I2R3C18A1, I2R3C18-1A1, I2R3C18-2A1, I2R11C14A1, I2R11C16A1, I2R11C18A1, I2R11C18-1A1, I2R11C18-2A1.

11. The method according to claim 9, wherein the cationic lipid analog material is at least one selected from the group consisting of I1R2C14A1, I1R2C16A1, I1R2C18A1, I1R2C18-1A1, I1R2C18-2A1, I1R11C14A1, I1R11C16A1, I1R11C18A1, I2R1C14A1, I2R1C16A1, I2R1C18-1A1, I2R2C14A1, I2R2C16A1, I2R2C18A1, I2R2C18-1A1, I2R2C18-2A1, I2R3C14A1, I2R3C16A1, I2R3C18A1, I2R3C18-1A1, I2R3C18-2A1, I2R11C14A1, I2R11C16A1, I2R11C18A1, I2R11C18-1A1, I2R11C18-2A1.

12. The method according to claim 9, wherein the cationic lipid analog material is at least one selected from the group consisting of I2R2C18-1A1, I2R2C18-2A1, I2R3C18-1A1, I2R3C18-2A1.

13. The method according to claim 1, wherein the nucleic acids are at least one selected from the group consisting of mRNA, small interference RNA, short hairpin RNA, microRNA, guide RNA, CRISPR RNA, tracrRNA, plasmid DNA, minicircle DNA, genomic DNA.

14. The method according to claim 1, wherein the cell is from a human or a mouse.

15. The method according to claim 14, wherein the cell is a mouse dendritic cell (DC 2.4), a mouse macrophage (RAW 264.7), an adenocarcinoma human alveolar basal epithelial cell (A549), a human pancreatic cancer cell (BxPC3), or a HeLa cell.

16. The method according to claim 1, wherein the cell is an A549 cell (A549-Luc).

* * * * *